(12) United States Patent
Schymkowitz et al.

(10) Patent No.: US 11,872,262 B2
(45) Date of Patent: Jan. 16, 2024

(54) MEANS AND METHODS FOR TREATING BACTERIAL INFECTIONS

(71) Applicants: VIB VZW, Ghent (BE); Katholieke Universiteit Leuven, K.U. Leuven R&D, Leuven (BE)

(72) Inventors: Joost Schymkowitz, Meensel-Kiezegem (BE); Frederic Rousseau, Sint-Martens-Bodegem (BE)

(73) Assignees: VIB VZW, Ghent (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 32 days.

(21) Appl. No.: 16/612,121

(22) PCT Filed: May 9, 2018

(86) PCT No.: PCT/EP2018/062152
§ 371 (c)(1),
(2) Date: Nov. 8, 2019

(87) PCT Pub. No.: WO2018/206732
PCT Pub. Date: Nov. 15, 2018

(65) Prior Publication Data
US 2021/0077563 A1    Mar. 18, 2021

(30) Foreign Application Priority Data

May 9, 2017 (EP) .................................. 17170233
May 9, 2017 (EP) .................................. 17170252

(51) Int. Cl.
*A61K 38/16* (2006.01)
*A61K 38/08* (2019.01)
*A61P 31/04* (2006.01)

(52) U.S. Cl.
CPC .............. *A61K 38/08* (2013.01); *A61P 31/04* (2018.01)

(58) Field of Classification Search
None
See application file for complete search history.

(56) References Cited

U.S. PATENT DOCUMENTS

| 4,186,183 | A | 1/1980 | Steck et al. |
|---|---|---|---|
| 4,217,344 | A | 8/1980 | Vanlerberghe et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |
| 4,501,728 | A | 2/1985 | Geho et al. |
| 4,550,017 | A | 10/1985 | Liu et al. |
| 4,774,085 | A | 9/1988 | Fidler |
| 4,797,368 | A | 1/1989 | Carter et al. |
| 4,837,028 | A | 6/1989 | Allen |
| 4,897,355 | A | 1/1990 | Eppstein et al. |
| 4,946,787 | A | 8/1990 | Eppstein et al. |
| 5,049,386 | A | 9/1991 | Eppstein et al. |
| 5,173,414 | A | 12/1992 | Lebkowski et al. |
| 6,159,748 | A | 12/2000 | Hechinger |
| 6,372,967 | B1 | 4/2002 | Mariani et al. |
| 6,399,317 | B1 | 6/2002 | Weimer |
| 6,489,092 | B1 | 12/2002 | Benjamin et al. |
| 6,627,616 | B2 | 9/2003 | Monahan et al. |
| 6,682,940 | B2 | 1/2004 | Pankowsky |
| 8,669,418 | B2 | 3/2014 | Schymkowitz et al. |
| 9,095,556 | B2 | 8/2015 | Schymkowitz et al. |
| 2002/0098173 | A1 | 7/2002 | Findeis et al. |
| 2005/0026165 | A1 | 2/2005 | Orser et al. |
| 2005/0203010 | A1 | 9/2005 | Kim |
| 2006/0122122 | A1 | 6/2006 | Kobayashi et al. |
| 2006/0193774 | A1 | 8/2006 | Summerton |
| 2009/0012275 | A1 | 1/2009 | Schymkowitz et al. |
| 2010/0184681 | A1 | 7/2010 | Eckert et al. |
| 2011/0035155 | A1 | 2/2011 | Vendruscolo et al. |

FOREIGN PATENT DOCUMENTS

| WO | WO 91/16024 A1 | 10/1991 |
|---|---|---|
| WO | WO 91/17424 A1 | 11/1991 |
| WO | WO 93/24641 A2 | 12/1993 |
| WO | WO 03/083441 A2 | 10/2003 |
| WO | WO 2003/102187 A1 | 12/2003 |
| WO | WO 2007/014391 A2 | 2/2007 |
| WO | WO 2007/071789 A1 | 6/2007 |
| WO | WO 2008/036293 A1 | 3/2008 |
| WO | WO 2008/116468 A2 | 10/2008 |
| WO | WO 2008/148751 A1 | 12/2008 |
| WO | WO 2009/041633 A1 | 4/2009 |
| WO | WO 2010/076642 A1 | 7/2010 |
| WO | WO 2010/080538 A1 | 7/2010 |
| WO | WO 2012/123419 A1 | 9/2012 |

(Continued)

OTHER PUBLICATIONS

Registry entry for 2043602-86-2, entered Dec. 7, 2016, 4 pages (Year: 2016).*
Seq ID No. 16158 from WO 2014/200910 (retrieved from https://patentscope.wipo.int/search/en/detail.jsf?docId=WO2014200910&tab=PCTDOCUMENTS on May 26, 2021, 1 page) (Year: 2014).*
Altmann, et al., "Inhibition of Vaccinia virus entry by a broad spectrum antiviral peptide," Virology, vol. 388, No. 2, pp. 248-259, 2009.
Amer, et al., "Antimicrobial and antibiofilm activity of cathelicidins and short, synthetic peptides against *Francisella*," Biochemical and Biophysical Research Communications, vol. 396, pp. 246-251, 2010.

(Continued)

*Primary Examiner* — Ronald T Niebauer
(74) *Attorney, Agent, or Firm* — Morgan, Lewis & Bockius LLP

(57) ABSTRACT

The present invention relates to non-naturally occurring anti-bacterial peptides. More specifically the peptides can be used to treat multi-drug resistant bacterial infections. In addition, the present invention provides methods for producing anti-bacterial peptides.

Figure 1:
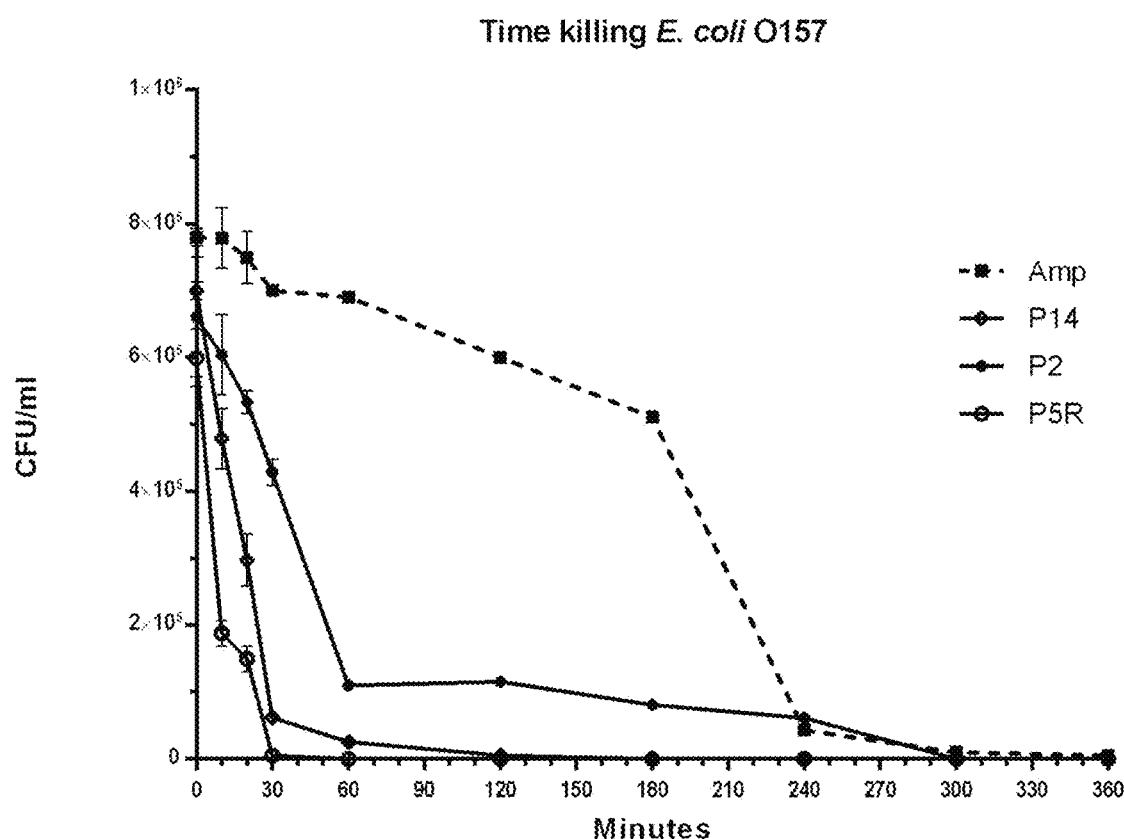
Figure 1:
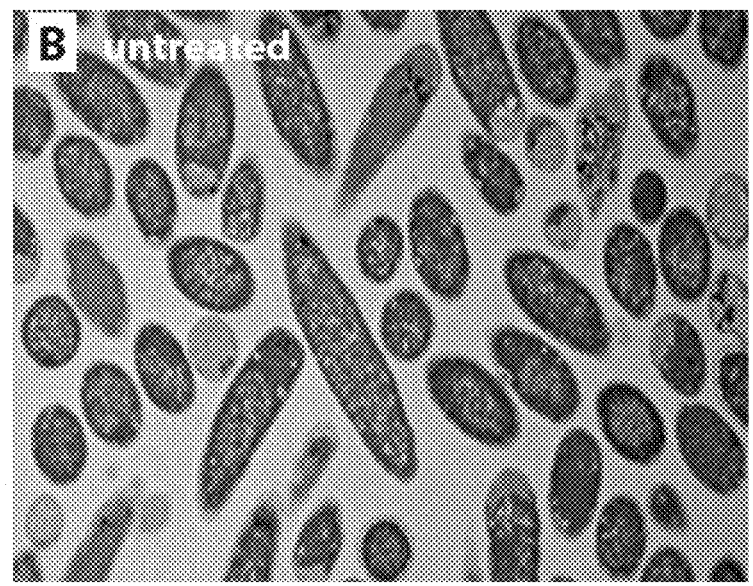
Figure 1:
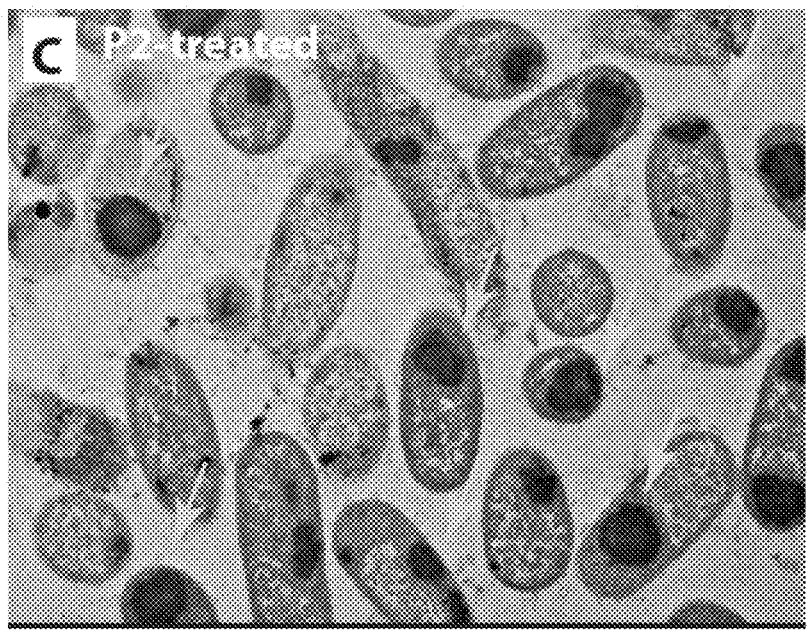
Figure 1:
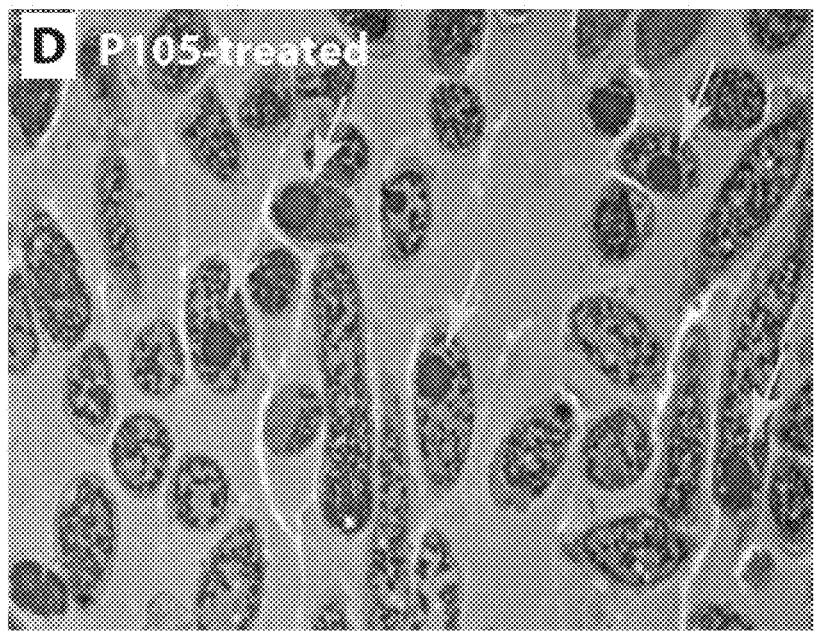
Figure 1:
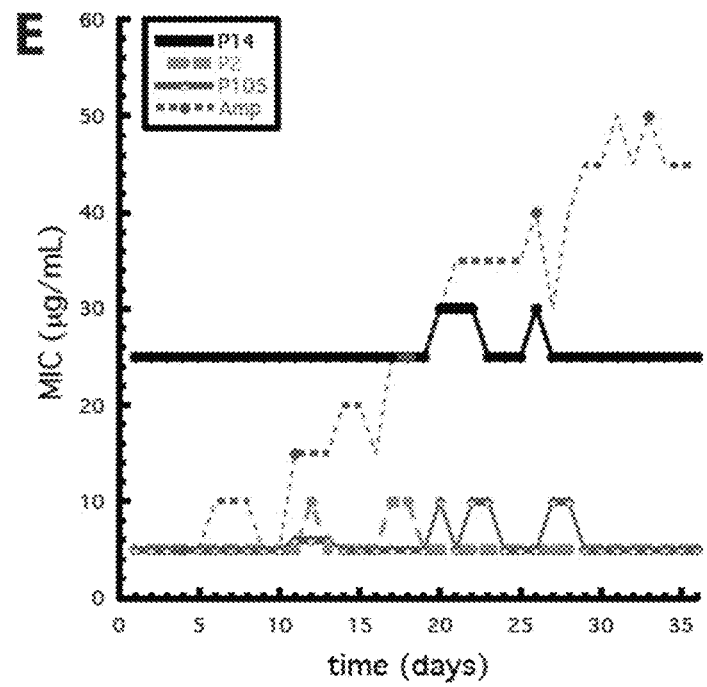
Figure 1:
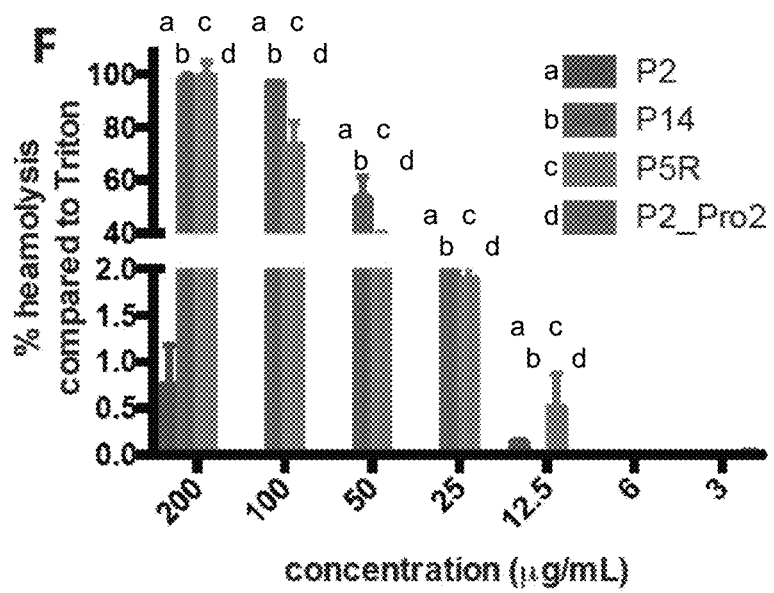
Figure 1:
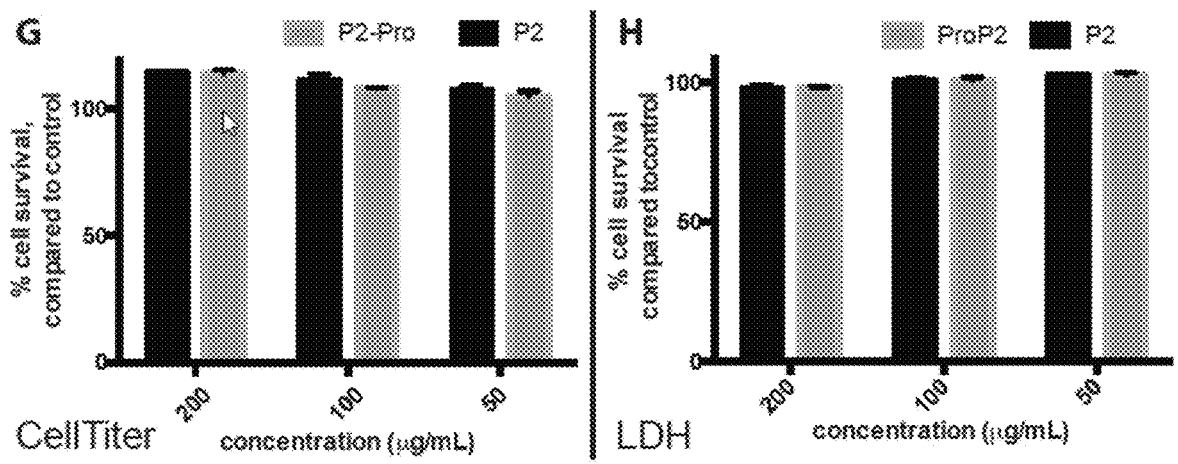
Figure 1:
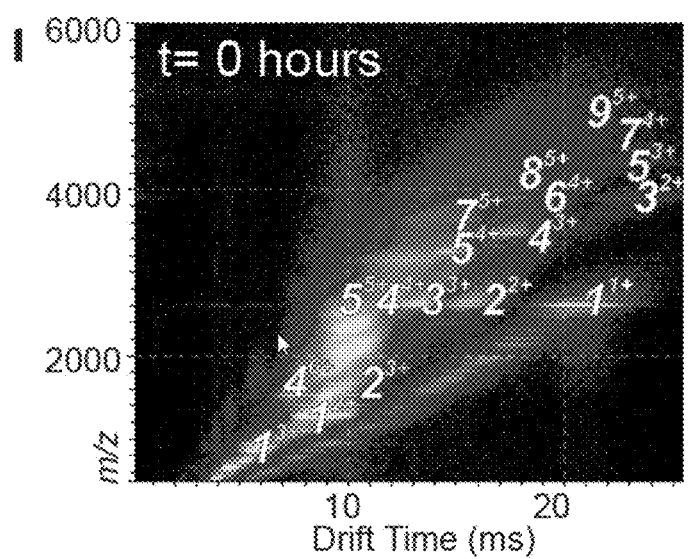
Figure 1:
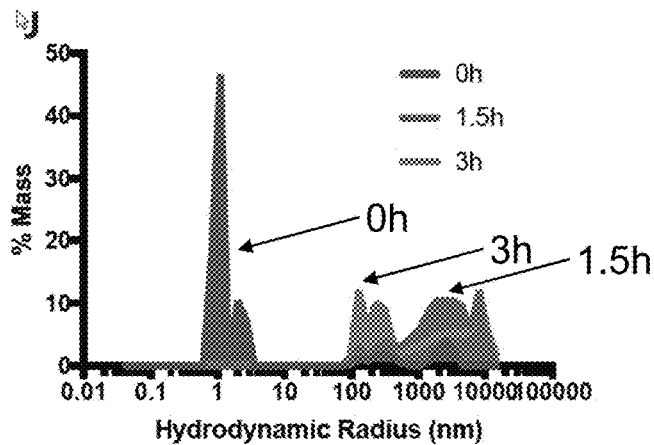
Figure 1:
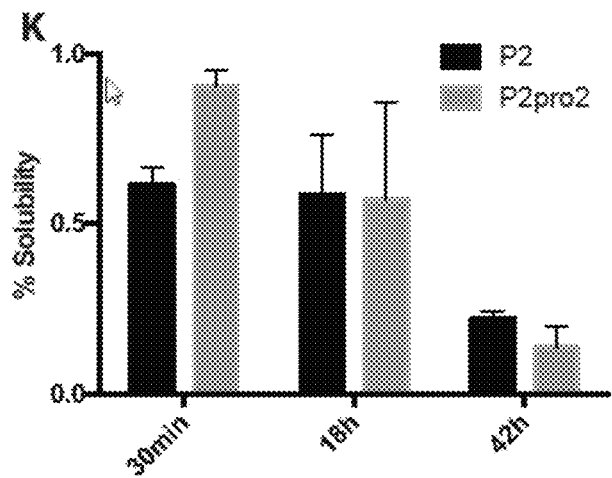
Figure 1:
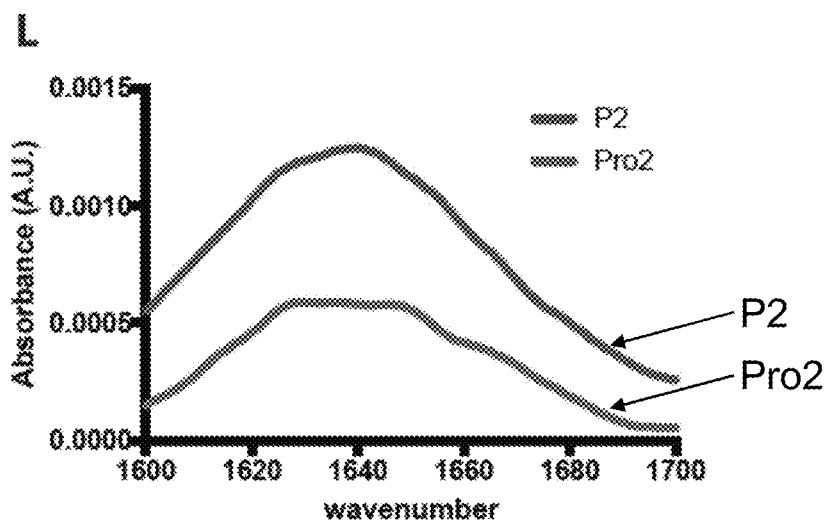
Figure 1:
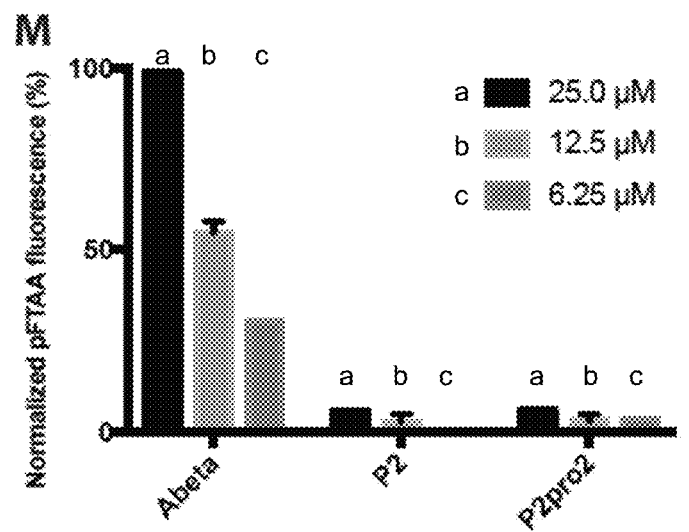
Figure 1:
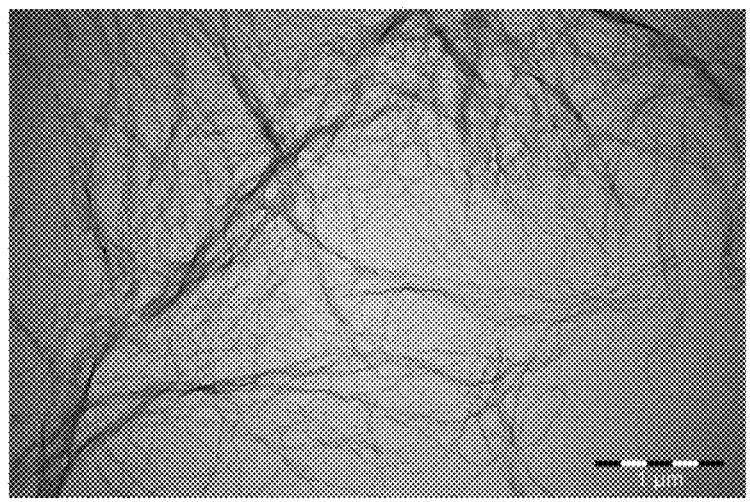
Figure 1:
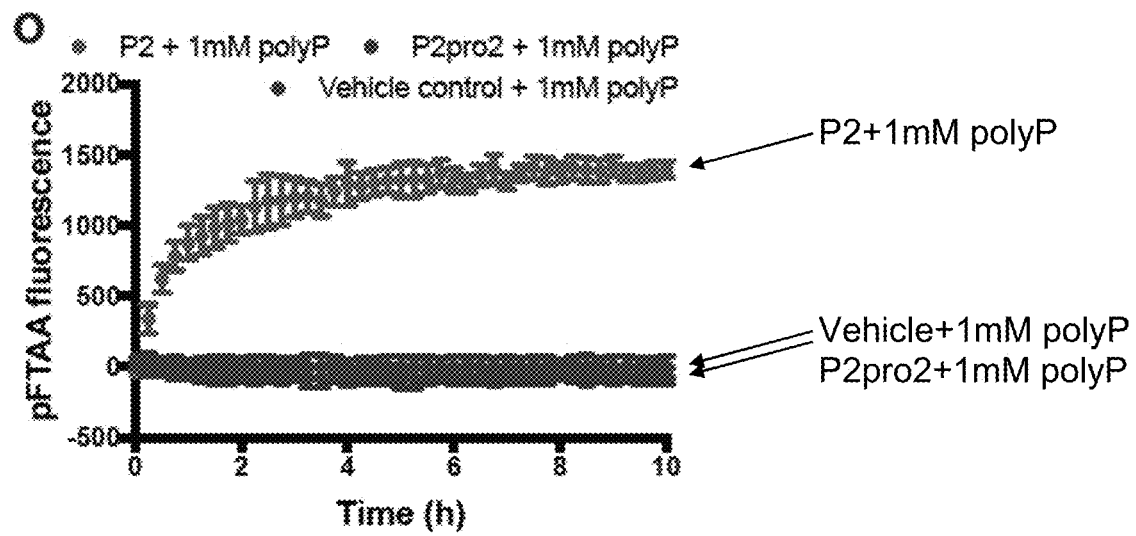

9 Claims, 19 Drawing Sheets
Specification includes a Sequence Listing.

(56) References Cited

FOREIGN PATENT DOCUMENTS

| WO | WO 2014/200910 | * | 12/2014 |
|---|---|---|---|
| WO | 2016/172722 A1 | | 10/2016 |

OTHER PUBLICATIONS

Artemova, et al., "Acceleration of Protein Aggregation by Amphiphilic Peptides: Transformation of Supramolecular Structure of the Aggregates," Biotechnology Press, vol. 27, No. 3, pp. 846-854, 2011.
Auer, et al., "Self-Templated Nucleation in Peptide and Protein Aggregation," Physical Review Letters, vol. 101, No. 25, pp. 258101-1-285101-3, 2008.
Bairoch, et al., "The Universal Protein Resource (UniProt)," Nucleic Acids Research, vol. 33, pp. D154-D159, 2005.
Barelle, et al., "GFP as a quantitative reporter of gene regulation in *Candida albicans*," Yeast, vol. 21, pp. 333-340, 2004.
Barral, et al., "Roles of molecular chaperones in protein misfolding diseases," Seminars in Cell & Developmental Biology, vol. 15, pp. 17-29, 2004.
Batrakov, et al., "A novel lipopeptide, an inhibitor of bacterial adhesion, from the thermophilic and halotolerant subsurface *Bacillus licheniformis* strain 603," Biochimica et Biophysica Acta, vol. 1634, No. 3, pp. 107-115, 2003.
Batoni, et al., "Use of Antimicrobial Peptides Against Microbial Biofilms: Advantages and Limits," Current Medicinal Chemistry, vol. 18, pp. 256-279, 2011.
Beerten, et al., "Aggregation Prone Regions and Gatekeeping Residues in Protein Sequences," Current Topics in Medicinal Chemistry, vol. 12, pp. 2470-2478, 2012.
Cao, et al., "Whole-genome sequencing of multiple *Arabidopsis thaliana* populations," Nature Genetics, vol. 43, No. 10, pp. 956-963, 2011.
Chi, et al., "Physical Stability of Proteins in Aqueous Solution: Mechanism and Driving Forces in Nonnative Protein Aggregation," Pharmaceutical Research, vol. 20, No. 9, 12 pages, 2003.
Chiti, et al., "Rationalization of the effects of mutations on peptide and protein aggregation rates," Nature, vol. 424, pp. 805-808, Aug. 14, 2003.
Clark, "Protein aggregation determinants from a simplified model: Cooperative folders resist aggregation," Protein Science, vol. 14, pp. 653-662, 2005.
Demarco, et al., "The solubility and stability of recombinant proteins are increased by their fusion to NusA," Biochemical and Biophysical Research Communications, vol. 322, pp. 766-771, 2004.
Dirr, et al., "Refined Crystal Structure of Porcine Class Pi Gluthathione S-Transferase (pGST P1-1) as 2-1 Å Resolution," J. Mol. Biol., vol. 243, pp. 72-92, 1994.
Dobson, "Getting out of shape," Nature, vol. 418, pp. 729-730, 2002.
Dobson, "Principles of protein folding, misfolding and aggregation," Seminars in Cell & Developmental Biology, vol. 15, pp. 3-16, 2004.
Dragani, et al., "Conformational properties of five peptides corresponding to the entire sequence of glutathione transferase domain II," Arch Biochem Biophys., vol. 389, vol. 1, abstract, 2001.
Esteras-Chopo, et al., "The amyloid stretch hypothesis: Recruiting proteins toward the dark side," PNAS, vol. 102, No. 46, pp. 16672-16677, Nov. 15, 2005.
Editorial, "Microbiology by numbers," Nature, 9:628, 2011.
European Search Report, application No. EP18171179.7 dated Jun. 29, 2018, 25 pages.
Fernandez-Escamilla, et al., "Prediction of sequence-dependent and mutational effects on the aggregation of peptides and proteins," Nature Biotechnology, vol. 22, No. 10, pp. 1302-1306, 2004.
Fernandez-Escamilla, et al., "Supplementary Table 1," https://media.nature.com/original/nature-assets/nbt/journal/22/n10/extref/nbt1012-S2.pdf, 2004.
Fletcher, et al., "Plant Pathogen Forensics: Capabilities, Needs, and Recommendations," Microbiology and Molecular Biology Reviews, vol. 70, No. 2, pp. 450-471, 2006.
Fonzi, et al., "Isogenic Strain Construction and Gene Mapping in *Candida albicans*," Genetics, vol. 135, pp. 717-728, Jul. 1993.
Frank, et al., "Structure and Function of Glycosylated Tandem Repeats from *Candida albicans* Als Adhesins," Eukaryotic Cell, vol. 9, No. 3, pp. 405-414, 2010.
Frenkel, et al., "High affinity binding of monoclonal antibodies to the sequential epitope EFRH of β-amyloid peptide is essential for modulation of fibrillar aggregation," Journal of Immunology, vol. 95, pp. 136-142, 1999.
Garcia, et al., "A Role for Amyloid in Cell Aggregation and Biofilm Formation," PLoS One, vol. 6, No. 3, 13 pages, Mar. 2011.
Guex, et al., "SWISS-MODEL and the Swiss-Pdb Viewer: An environment for comparative protein modeling," Electrophoresis, vol. 18, pp. 2714-2723, 1997.
Hamada, et al., "Engineering amyloidogenicity towards the development of nanofibrilar materials," TRENDS in Biotechnology, vol. 22, No. 2, pp. 93-97, 2004.
Houry, et al., "Identification of in vivo substrates of the chaperonin GroEL," Nature, vol. 402, pp. 147-154, 1999.
Karlsson, et al., "Effect of Sequence and Structural Properties on 14-Helical β-Peptide Activity against *Candida albicans* Planktonic Cells and Biofilms," ASC Chemical Biology, vol. 4, No. 7, pp. 567-579, 2009.
Karlsson, et al., "Polyelectrolyte Multilayers Fabricated from Antifungal β-Peptides: Design of Surfaces that Exhibit Antifungal Activity Against *Candida albicans*," Biomacromolecules, vol. 11, No. 9, pp. 2321-2328, 2010.
Kizana, et al., "Therapeutic Prospects of Cardiac Gene Transfer," Heart, Lung and Circulation, vol. 16, pp. 180-184, 2007.
Kopp, et al., "The SWISS-MODEL Respository of annotated three-dimensional protein structure homology models," Nucleic Acids Research, vol. 32, pp. D230-D234, 2004.
Kuhn, et al., "Candida biofilms: Antifungal resistance and emerging therapeutic options," Current Opinion in Investigational Drugs, vol. 5, No. 2, pp. 186-197, 2004.
Kundu, et al., "Manipulation of Unfolding-Induced Protein Aggregation by Peptides Selected for Aggregate-Binding Ability through Phage Display Library Screening," Biochemical and Biophysical Research Communications, vol. 291, pp. 903-907, 2002.
Lam, et al., "Role of SH3 Domain-Containing Proteins in Clathrin-Mediated Vesicle Trafficking in Arabidopsis," The Plant Cell, vol. 13, pp. 2499-2512, Nov. 2001.
Lee, et al., "Production of recombinant amyloid-β peptide 42 as an ubiquitin extension," Protein Expression and Purification, vol. 40, pp. 183-189, 2005.
Leuker, et al., "Sequence and promoter regulation of the PCK1 gene encoding phosphoenolpyruvate carboxykinase of the fungal pathogen *Candida albicans*," Gene, vol. 192, pp. 235-240, 1997.
Linding, et al., "A Comparative Study of the Relationship Between Protein Structure and β-Aggregation in Globular and Intrinsically Disordered Proteins," J. Mol. Biol., vol. 342, pp. 345-353, 2004.
Liu, et al., "*Candida albicans* Als3, a Multifunctional Adhesin and Invasin," Eukaryotic Cell, vol. 10, No. 2, pp. 168-173, 2011.
Liu, et al., "Enhanced overall resistance to Fusarium seedling blight and Fusarium head blight in transgenic wheat by co-expression of anti-fungal peptides," Eur J. Plant Pathol, vol. 134, pp. 721-732, 2012.
López De La Paz, et al., "De novo designed peptide-based amyloid fibrils," PNAS, vol. 99, No. 25, pp. 16052-16057, 2002.
López De La Paz, et al., "Sequence determinants of amyloid fibril formation," PNAS, vol. 101, No. 1, pp. 87-92, 2004.
Makin, et al., "Molecular basis for amyloid fibril formation and stability," PNAS, vol. 102, No. 2, pp. 315-320, 2005.
Massodi, et al., "Application of Thermally Responsive Elastin-like Polypeptide Fused to a Lactoferrin-derived Peptide for Treatment of Pancreatic Cancer," Molecules, vol. 14, pp. 1999-2015, 2009.
McCarty, et al., "Regulatory Region C of the *E. coli* Heat Shock Transcription Factor, $\sigma^{32}$, Constitutes a Dnak Binding Site and is Conserved Among Eubacteria," J. Mol. Biol., vol. 256, pp. 829-837, 1996.

(56) References Cited

OTHER PUBLICATIONS

Monsellier, et. al., "Aggregation Propensity of the Human Proteome," PLoS Computational Biology, vol. 4, No. 10, 9 pages, Oct. 2008.
Nagel-Wolfrum, et al., "The Interaction of Specific Peptide Aptamers with the DNA Binding Domain and the Dimerization Domain of the Transcription Factor Stat3 Inhibits Transactivation and Induces Apoptosis in Tumor Cells," Molecular Cancer Research, vol. 2, pp. 170-182, Mar. 2004.
Nelson, et al., "Structure of the cross-β spine of amyloid-like fibrils," Nature, vol. 435, pp. 773-778, 2005.
Otoo, et al., "*Candida albicans* Als Adhesins Have Conserved Amyloid-Forming Sequences," Eukaryotic Cell, vol. 7, No. 5, pp. 776-782, 2008.
Ouberai, et al., "Synthesis and Biological Evaluation of Clicked Curcumin and Clicked KLVFFA Conjugates as Inhibitors of Beta-Amyloid Fibril Formation," Bioconjugate Chem., vol. 20, pp. 2123-2132, 2009.
Paleologou, et al., "α-Synclein aggregation in neurodegenerative diseases and its inhibition as a potential therapeutic strategy," Biochemical Society Transactions, vol. 33, No. 5, pp. 1106-1110, 2005.
Pawar, et al., "Prediction of "Aggregation-prone" and "Aggregation-susceptible" Regions in Proteins Associated with Neurodegenerative Diseases," J. Mol. Biol., vol. 350, pp. 379-392, 2005.
PCT International Search Report, PCT Application No. PCT/EP2006/070184, dated Mar. 16, 2007, 1 page.
Pike, et al., "Structure-Activity Analyses of β-Amyloid Peptides: Contributions of the β25-335 Region to Aggregation and Neurotoxicity," Journal of Neurochemistry, vol. 64, No. 1, pp. 253-262, 1995.
Poduslo, et al., "β-Sheet Breaker Peptide Inhibitor of Alzheimer's Amyloidogenesis with Increased Blood-Brain Barrier Permeability and Resistance to Proteolytic Degradation in Plasma," J. Neurobiology, vol. 39, No. 3, pp. 371-382, 1999.
Prasanna, et al., "Synthetic Interface Peptides as Inactivators of Multimeric Enzymes: Inhibitory and Conformational Properties of Three Fragments from *Lactobacillus casei* Thymidylate Synthase," Biochemistry, vol. 37, pp. 6883-6893, 1998.
Ramsook, et al., "Yeast Cell Adhesion Molecules Have Functional Amyloid-Forming Sequences," Eukaryotic Cell, vol. 9, No. 3, pp. 393-404, 2010.
Rathinakumar, et al., "Broad-Spectrum Antimicrobial Peptides by Rational Combinatorial Design and High-Throughput Screening: The Importance of Interfacial Activity," J. Am. Chem. Soc., vol. 131, pp. 7609-7617, 2009.
Reumers, et al., "Protein Sequences Encode Safeguards Against Aggregation," Human Mutation, vol. 30, No. 3, pp. 431-437, 2009.
Rousseau, et al., "How Evolutionary Pressure Against Protein Aggregation Shaped Chaperone Specificity," J. Mol. Biol., vol. 355, pp. 1037-1047, 2006.
Rousseau, et al., "Protein aggregration and amyloidosis: confusion of the kinds?" Current Opinion in Structural Biology, vol. 16, pp. 118-126, 2006.
Sánchez De Groot, et al., "Prediction of "hot spots" of aggregation in disease-linked polypeptides," BMC Structural Biology, vol. 5, No. 18, 15 pages, 2005.
Soto, et al., "Beta-sheet breaker peptides inhibit fibrillogenesis in a rat brain model of amyloidosis: implications for Alzheimer's therapy," Nat. Med., vol. 4, No. 7, Abstract, 1998.
Soto, et al., "Reversion of prion protein conformational changes by synthetic b-sheet breaker peptides," Lancet, vol. 355, pp. 192-197, 2000.
Sung, et al., "The importance of valency in enhancing the import and cell routing potential transduction domain-containing molecules," Biochimica et Biophysica Acta, vol. 1758, No. 3, pp. 355-363, 2006.
Tanaka, et al., "Induction of Antigen-Specific CTL by Recombinant HIV Trans-Activating Fusion Protein-Pulsed Human Monocyte-Derived Dedritic Cells," The Journal of Immunology, vol. 170, No. 3, pp. 1291-1298, 2003.
Tartaglia, et al., "Prediction of aggregation rate and aggregation-prone segments in polypeptide sequences," Protein Science, vol. 14, No. 10, pp. 2723-2734, Oct. 2005.
Van Oss, et al., "Nature of the antigen-antibody interaction. Primary and secondary bonds: optimal conditions for association and dissociation," J. Chromatogr., vol. 376, pp. 111-119, 1986.
Ventura, et al., "Short amino acid stretches can mediate amyloid formation in globular proteins: The Src homology 3 (SH3) case," PNAS, vol. 101, No. 19, pp. 7258-7263, 2004.
Yoon, et al., "Detecting hidden sequence propensity for amyloid fibril formation," Protein Science, vol. 13, No. 2, pp. 2149-2160, 2004.
Yudt, et al., "Preventing estrogen receptor action with dimer-interface peptides," Steroids, vol. 66, pp. 549-558, 2001.
International Search Report issued in corresponding International Patent Application No. PCT/EP2018/062152 dated Aug. 22, 2018.
Written Opinion issued in corresponding International Patent Application No. PCT/EP2018/062152 dated Aug. 22, 2018.
Bednarska et al., "Protein aggregation as an antibiotic design strategy," Molecular Microbiology, 99 (5): 849-865 (2016).
De Baets et al., "Predicting aggregation-prone sequences in proteins," Essays in Biochemistry, 56: 41-52 (2014).
Khodaparast et al., "Aggregating sequences that occur in many proteins constitute weak spots of bacterial proteostasis," Nature Communications, 9: 866 (2018).
Karlsson, et al., "Effect of Sequence and Structural Properties on 14-Helical β-Peptide Activity against *Candida albicans* Planktonic Cells and Biofilms," ASC Chemical Biology, vol. 4, No. 7, pp. 567-579, Jun. 11, 2009.
Klotz, et al., "Inhibition of Adherence and Killing of *Candida albicans* with a 23-Mer Peptide (Fn/23) with Dual Antifungal Properties," Antimicrobial Agents and Chemotherapy, vol. 48, No. 11, pp. 4337-4341, Jun. 30, 2004.
Sasaki, et al., "Effects of amino acid mismatch in the UNOS dataset," Clin Transpl., Chapter 27, 2 pages, 2011.

\* cited by examiner

A

N

A

Figure 8

| Peptides | MIC (ug/ml) | | | | Hemolytic activity |
|---|---|---|---|---|---|
| | E.cali BL2 | Acinetoba | Klebsiella pneumoni | Pseudomo | |
| P1 | >100 | >100 | >100 | | |
| P3 | >100 | >100 | >100 | | |
| P4 | >100 | >100 | >100 | | |
| P11 | 100 | 50 | >100 | >100 | |
| P12 | 25 | 12 | >100 | >100 | |
| P13 | 25 | 25 | >100 | >100 | |
| P14 | 6 | 6 | >100 | 50 | |
| P1 | >100 | >100 | >100 | >100 | >100 |
| P3 | >100 | >100 | >100 | >100 | >50 |
| P4 | >100 | >100 | >100 | >100 | >100 |
| P11 | 50 | 50 | >100 | >100 | >200 |
| P12 | 25 | 12 | >100 | >100 | >200 |
| P13 | 25 | 25 | >100 | >100 | >200 |
| P14 | 6 | 6 | >100 | 50 | >200 |
| P15 | 12 | 25 | >100 | >100 | |
| P16 | 25 | 6 | >100 | >100 | |
| P18 | 12 | 12 | >100 | >100 | |
| P23 | >100 | >100 | >100 | >100 | |
| P24 | 12 | 12 | 100 | 100 | |
| P26 | 100 | 100 | >100 | >100 | |
| P33 | 12 | 12 | 25 | 25 | |
| P25 | >100 | 100 | >100 | >100 | |
| P39 | 25 | 12 | >100 | >100 | |
| P40 | >100 | 100 | >100 | >100 | |
| P50 | 25 | 25 | >100 | >100 | |
| P58 | 25 | 25 | 50 | 100 | |
| P40 | 50 | 6 | 100 | 100 | |
| P72 | >100 | 100 | >100 | >100 | |

Figure 9

| Organism | Strain | Genotype | Genotype | P2 | P2 means | Amoxy/cbv | Pipe/tazo | Cefotaxime | Ceftazid | Impenem | Mero penem | Gentamicin | Ciproflox | Tigecycline | Nitrofurantoin | Colistin | Timet/sulpha oxa |
|---|---|---|---|---|---|---|---|---|---|---|---|---|---|---|---|---|---|
| | | Tem-1 | | 16 | >32 | S | S | S | S | S | S | S | S | S | S | | S |
| | | VIM | | 8 | >32 | S | S | S | S | S | S | S | S | S | S | | |
| | | NDM-1 | | >32 | >32 | S | S | S | S | S | S | S | S | S | R | | S |
| | | Imp4212 | | 8 | >32 | S | S | S | S | S | S | S | S | S | S | | S |
| | | SHV-12 | | 2 | >32 | S | R | S | S | S | S | S | S | S | S | | S |
| | | Tem-1 | CTX-M-15 | 32 | >32 | S | S | R | R | S | S | S | S | S | S | | S |
| | | SHV-12 | | 16 | >32 | R | S | R | R | R | R | R | R | S | S | | R |
| | | NDM-1 | | 32 | >32 | R | S | R | R | S | S | S | S | S | S | | S |
| | | GAC | | 16 | >32 | R | S | R | R | S | S | S | S | S | S | | R |
| | | KPC | | 8 | >32 | R | R | R | R | R | R | S | S | S | S | | R |
| | | NDM-5 | | 8 | >32 | R | R | R | R | R | R | R | R | S | S | | R |
| | | VIM-1 | CMY-2 | 8 | >32 | R | R | R | R | R | R | S | S | S | S | | R |
| | | IMP-1 | | 16 | >32 | R | R | R | R | R | R | S | S | S | S | | R |
| | | OXA-48 | | 16 | >32 | R | R | R | R | R | R | R | R | S | S | | S |
| | | CTX-M | | 16 | >32 | R | R | R | R | R | R | R | R | S | S | | S |
| | | NDM-1 | CTX-M-15 | 16 | >32 | R | R | R | R | R | R | R | R | S | S | | R |

MEANS AND METHODS FOR TREATING BACTERIAL INFECTIONS

CROSS-REFERENCE TO RELATED APPLICATIONS

This application is a national stage application of International Application No. PCT/EP2018/062152, which claims priority to EP 17170233.5, filed on May 5, 2017, and EP 17170252.5, filed on May 5, 2017. The entire contents of the aforementioned patent applications are incorporated herein by reference in their entireties.

SEQUENCE LISTING SUBMISSION VIA EFS-WEB

The instant application contains a Sequence Listing which has been submitted in ASCII format via EFS-Web and is hereby incorporated by reference in its entirety. Said ASCII copy, filed Dec. 11, 2021 is named "SequenceListing.txt" and is 57,344 bytes in size.

FIELD OF THE INVENTION

The present invention relates to non-naturally occurring anti-bacterial peptides. More specifically the peptides can be used to treat multi-drug resistant bacterial infections. In addition, the present invention provides methods for producing anti-bacterial peptides.

Introduction to the invention Microorganisms resistant to multiple drugs are of major concern and the consequences can be most profound for children, who are especially susceptible to bacterial infections. The most common childhood bacterial diseases in developing countries—pneumonia, other respiratory infections, and dysentery—are no longer curable by many of the older antibiotics. The consequences are devastating: bacterial acute respiratory infections, for example, kill more than three million children every year. Many cases of these illnesses are caused by strains now resistant to common antibiotics. In wealthier countries, hospitals are reeling from an explosion of methicillin-resistant Staphylococcus aureus (MRSA). From 1974 to 2004, MRSA prevalence increased from roughly 2 percent to more than 50 percent of staph infections in many U.S. hospitals, resulting in tens of thousands of deaths. Resistance to antibiotics also has a startling impact on the cost of curing patients. In many poor countries, expenditures for drugs represent a large proportion of overall health-care costs, ranging from 20 to 60 percent of total expenditure on health. When first-line drugs fail, second-line alternative drugs are almost always far more costly and require greater medical oversight. For example, it costs as much to cure one patient of extensively drug-resistant TB as it does to cure 200 patients of susceptible TB. Besides the known pathogens, the relatively recent appearance of opportunistic organisms, intrinsically resistant to many drugs, is also complicating the advances that have been made in medical technologies. With a larger number of immunocompromised patients and longer time periods spent in an immunocompromised state, several organisms have become 'specialized' pathogens—typically attacking only the most vulnerable patients. Among these opportunistic pathogens are the enterococci, the coagulase-negative staphylococci, Pseudomonas aeruginosa and Acinetobacter baumanii.

In the present invention we disclose a novel designer antibiotics paradigm that exploits protein aggregation to kill bacteria by widespread proteostatic collapse. Loss of protein homeostasis or proteostasis[1] is a constant threat for any living cell due to the highly crowded intracellular environment that brings into close proximity a large variety of polypeptides that need to undergo error-prone folding reactions in order to attain their native conformation[2]. To control this threat, cells have evolved a complex network of molecular chaperones, proteases and other specialized molecules[3]. Although the basic components of this machinery are conserved in all kingdoms of life, bacteria have relatively simple proteostatic networks in comparison to the more elaborate versions observed in eukaryotic cells[4]. In spite of these cellular response mechanisms, human protein folding pathologies have made clear that under persistent exposure to aggregating proteins, e.g. as a result of mutation, the proteostasis network eventually breaks down, which ultimately results in cell death[5]. On the other hand, protein aggregation turns out to be a highly ordered and specific process: aggregation is more efficient between similar than between unrelated polypeptides[6-8]. At a mechanistic level protein aggregation is mediated by short aggregation prone sequence segments (called APRs), which on average occur roughly once every 100 amino acids in the primary polypeptide sequence. These APRs are generally (but not always) sequence segments constituting the hydrophobic core of globular proteins or protein-protein interaction interfaces. Unfortunately the physicochemical requirement for providing these tertiary protein interaction modes also favour protein aggregation[9]. Indeed while forming the most stable part of the native proteins, in (partially) unfolded proteins, APRs can also self-assemble with identical APRs from another protein to form even more stable beta-structured aggregates[10]. The risk of aggregation is thus highest during translation, before the protein attains its native conformation[11]. Overall the bacterial proteomes display a higher intrinsic aggregation susceptibility than higher order organisms[14]. In addition, protein turnover in bacteria needs to be faster in order to support their high metabolic and cell division rates, which further increases the potential for protein aggregation in bacteria. Bacterial proteostasis is increasingly being investigated as a drug target for novel antibiotics[15]. For example, the antimicrobial peptide (AMP) oncocin exerts its antibacterial activity by binding to the ribosome exit channel[16]. Interestingly, there is a notable overlap between the amyloid forming propensity of peptides and their antibacterial activity[17, 18] and we observed earlier that peptides derived from aggregating protein fragments of the Gram positive Staphylococcus epidermidis, can be toxic specifically to these bacteria[19].

Protein aggregation is a sequence specific process allowing a protein to template its own aggregation but not that of heterologous sequences. We previously exploited this feature for specific protein detection in Western Blot[8] or to induce specific protein knockdown using short aggregation-prone sequence fragments (APRs) of target proteins. Using a transgenic GFP carrier fused to target APRs we generated specific loss-of-function phenotypes in both Arabidopsis thaliana and Zea mays resulting in increased plant size and increased starch content respectively[21]. We also found that it is possible to use synthetic peptides to the same effect and recently designed a peptide named vascin that is internalized by human cells and specifically induces VEGFR-2 inactivation by aggregation. Moreover vascin displays in vivo activity inhibiting VEGFR-2 dependent tumor growth in a syngenic murine model[47]. Recently we also explored whether synthetic peptides harboring endogenous APRs of Gram-positive Staphylococci can induce aggregation-associated bacterial death in vitro and found several that are active against MRSA in vivo[19].

SUMMARY OF THE INVENTION

Given the rapidly increasing problems of antibacterial resistance, especially in Gram-negative bacteria, we here set out to develop novel antimicrobial peptides against the enterohemorrhagic E. coli strain O157:H7, which produces high levels of toxins, leading to hemorrhagic diarrhea and kidney failure upon infection[20]. Under the assumption that the development of drug resistance is more difficult for drugs that have multiple targets, we searched for peptides that can cause misfolding or aggregation of multiple bacterial proteins. To this end we screened 125 aggregating sequences that had a high degree of redundancy in the E. coli proteome. In this manner one peptide containing this APR could potentially affect the folding of many proteins containing highly similar APRs. Using this strategy we identified several peptides that efficiently induce bactericidal protein aggregation and inclusion body formation in pathogenic E. coli. One representative of these—designated herein further as colpeptin1—showed little or no toxicity towards mammalian cells, and was also active against a number of other bacterial pathogens (see Table 2) and was effective in vivo against E. coli in a mouse bladder infection model. We demonstrate that the internalization of the non-natural peptides, such as colpeptin1, is followed by a rapid aggregation cascade of multiple proteins promoted by the primary colpeptin1 targets resulting in bacterial proteostatic collapse.

FIGURES

FIG. 1: Activity, cytotoxicity and aggregation of antibacterial aggregating peptides. (A) Time-killing curve of selected peptides against E. coli strain O157 treated at MIC concentration (average and s.d. of 3 replicates). (B, C, D) Transmission electron microcopy (TEM) of cross-sections of E. coli O157 embedded in resin. B is mock treated, C is P2- and D is P105-treated E. coli O157 (2 h). (E) Monitoring of spontaneous build-up of resistance by monitoring the MIC value of cultures that are maintained on sublethal doses of peptide or ampicillin (50% of MIC) for 36 days. (F) Concentration-dependent hemolysis of human erythrocytes by selected peptides (average and s.d. of 3 replicates). (G) Cytoxicity of Colpeptin1 to human HeLa cells measured by CellTiter Blue assay (average and s.d. of 3 replicates) and (H) by LDH release assay (average and s.d. of 3 replicates). (1) ESI-IMS-MS Driftscope plot of the colpeptin1 monomer (1) through to the nonamer (9) present two minutes after diluting the monomer to a final peptide concentration of 100 µM in 50 mM MES buffer pH 7. ESI-IMS-MS Driftscope plots show the IMS drift time versus mass/charge (m/z) versus intensity (z, square-root scale). Data are from a single experiment that was replicated 3 times (J) Histogram of the size distribution of particles calculated from the DLS data recorded of freshly dissolved colpeptin1 using a linear polymer as particle model. (K) Solubility of peptide samples after ultracentrifugation at 250.000 g for 2 h (average and s.d. of 4 replicates). (L) FTIR spectrum of the insoluble fractions obtained in the previous panel (average and s.d. of 4 replicates). (M) Fluorescence intensity of the amyloid-specific dye pFTAA added to preparation of colpeptin1, normalised to the intensity observed with amyloid fibrils of the Alzheimer beta-peptide at the same concentration in monomeric units (average and s.d. of 3 replicates). (N) representative transmission Electron Microscopy image of colpeptin1 (negative staining with uranyl acetate). (0) Aggregation kinetics of Colpeptin1 monitored by pFTAA fluorescence in the presence of 1 mM hexaphosphate (average and s.d. of 4 replicates).

Figure 2:
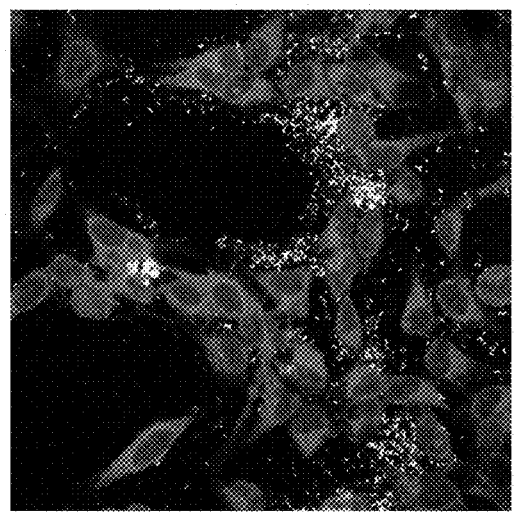
Figure 2:
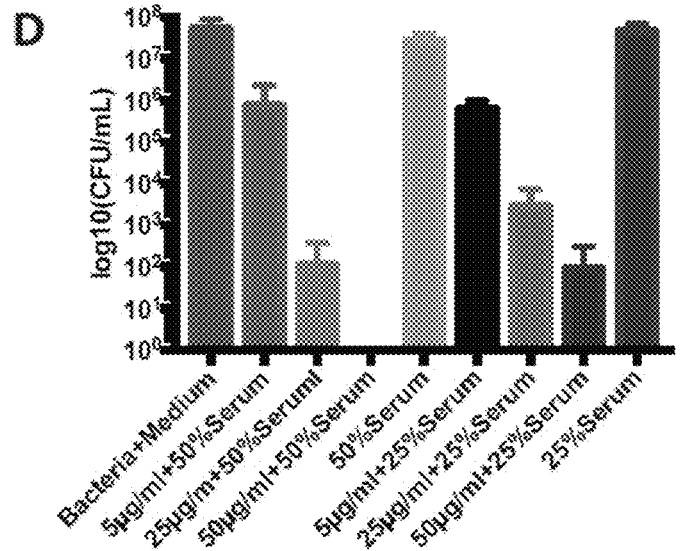
Figure 2:
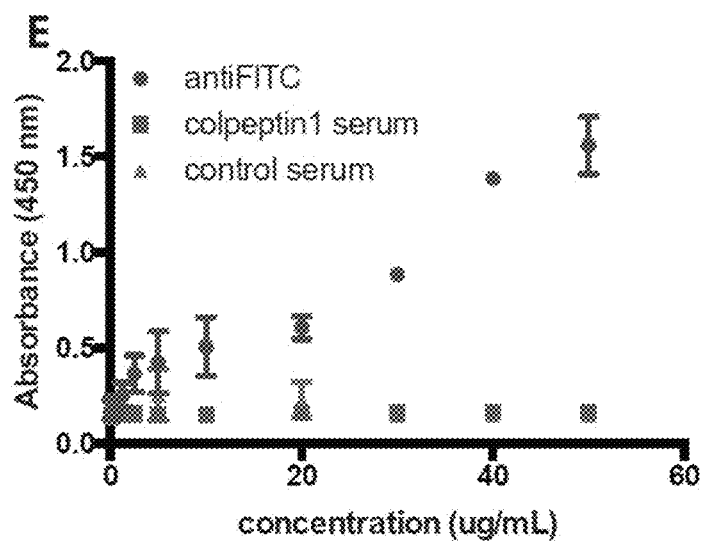
Figure 2:
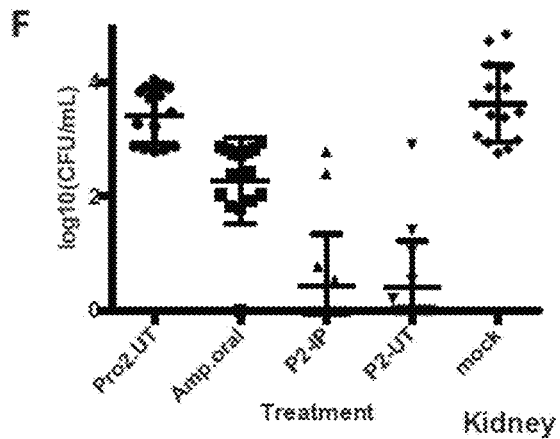
Figure 2:
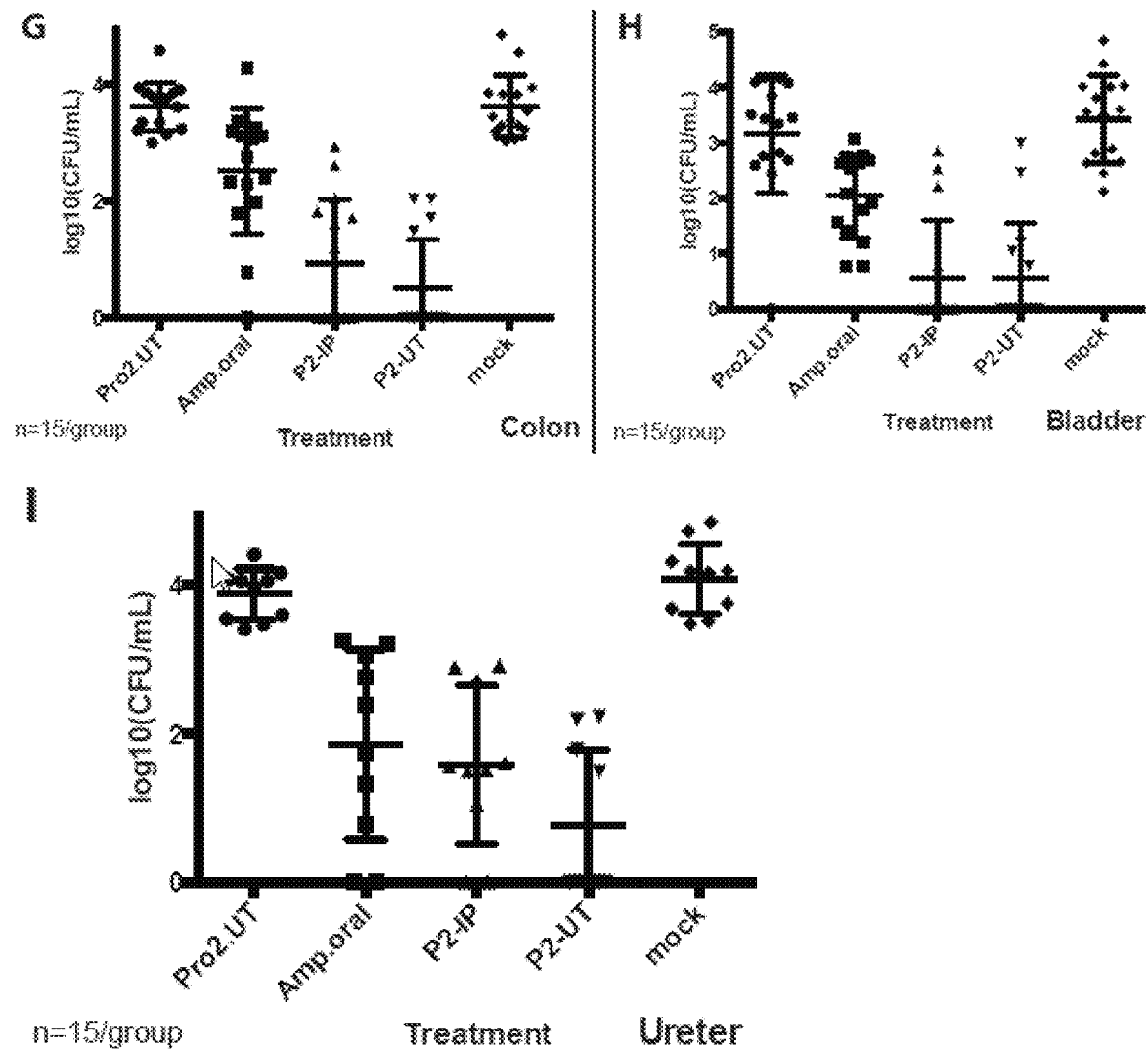

FIG. 2: Cross seeding and in vivo activity. (A) Fluorescence microscopy image of HeLa cells mixed with E. coli O157 and treated with FITC-labelled Colpeptin1 (green channel). Blue channel is DAPI, red is CellMask Deep Red plasma membrane dye. (D) Inhibitor effect of Colpeptin1 on bacterial growth in the presence of human blood serum (average and s.d. of 3 replicates). (E) ELISA on immobilised colpeptin1 using blood serum of animals treated for 18 days with 30 mg/kg colpeptin1 (3 replicates from 3 mice). (F-1) Bacterial load in the organs of mice infected with E. coli O157 transurethrally after treatment with Colpeptin1 (P2) and controls (ampicillin, buffer and P2-Pro, 15 animals per group) in (F) Kidney, (G) Colon, (H) Bladder and (I) Ureter. See materials and methods for details.

Figure 3:
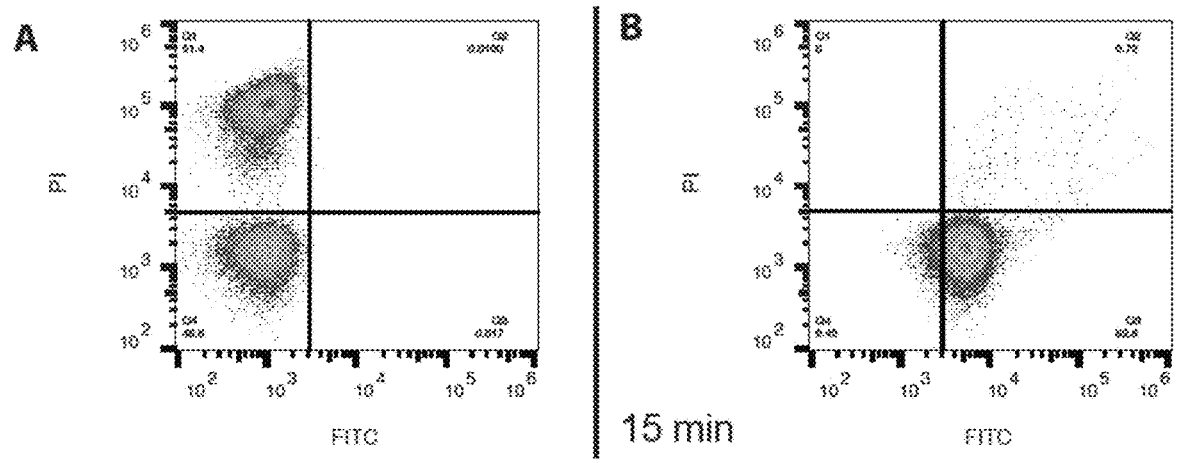
Figure 3:
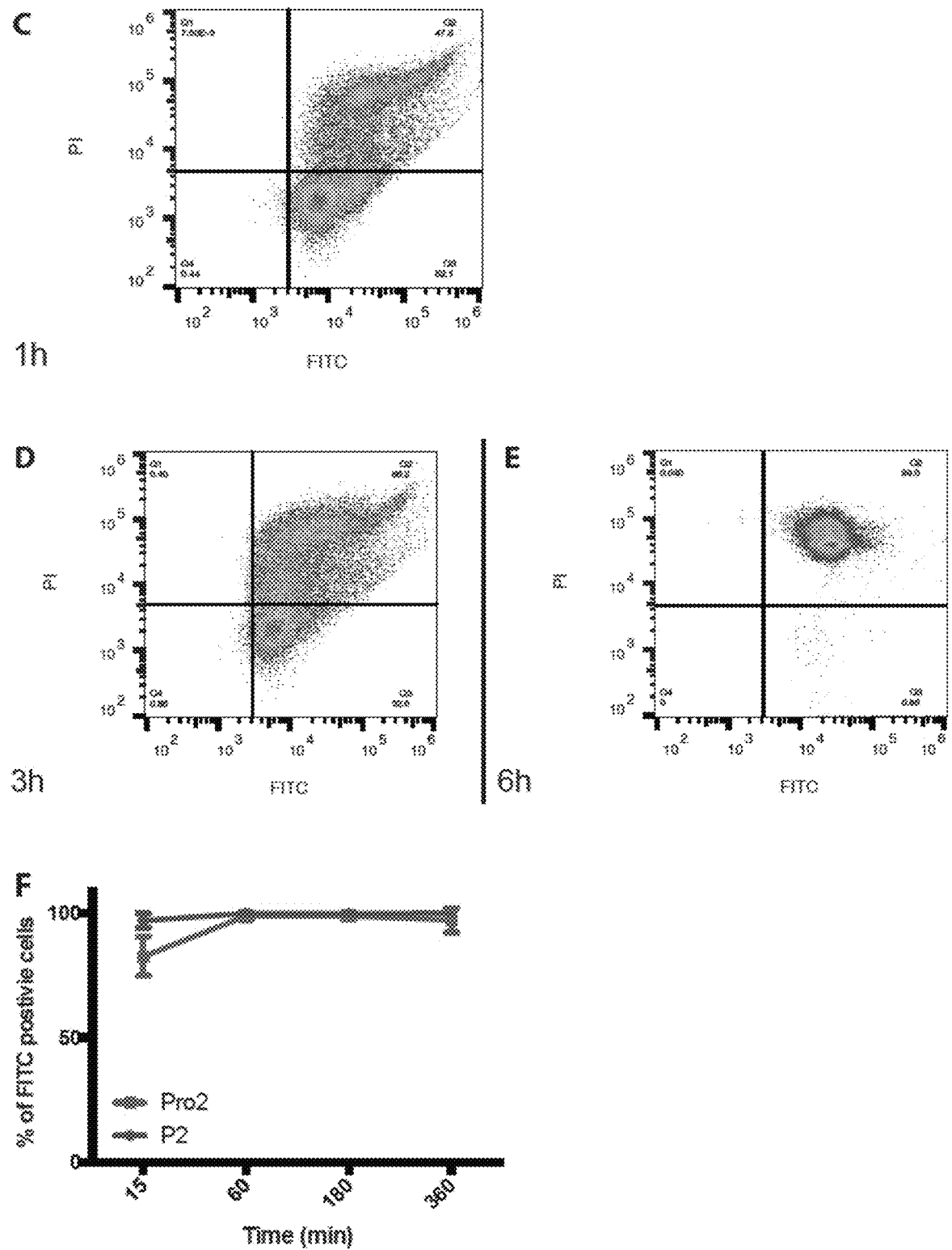
Figure 3:
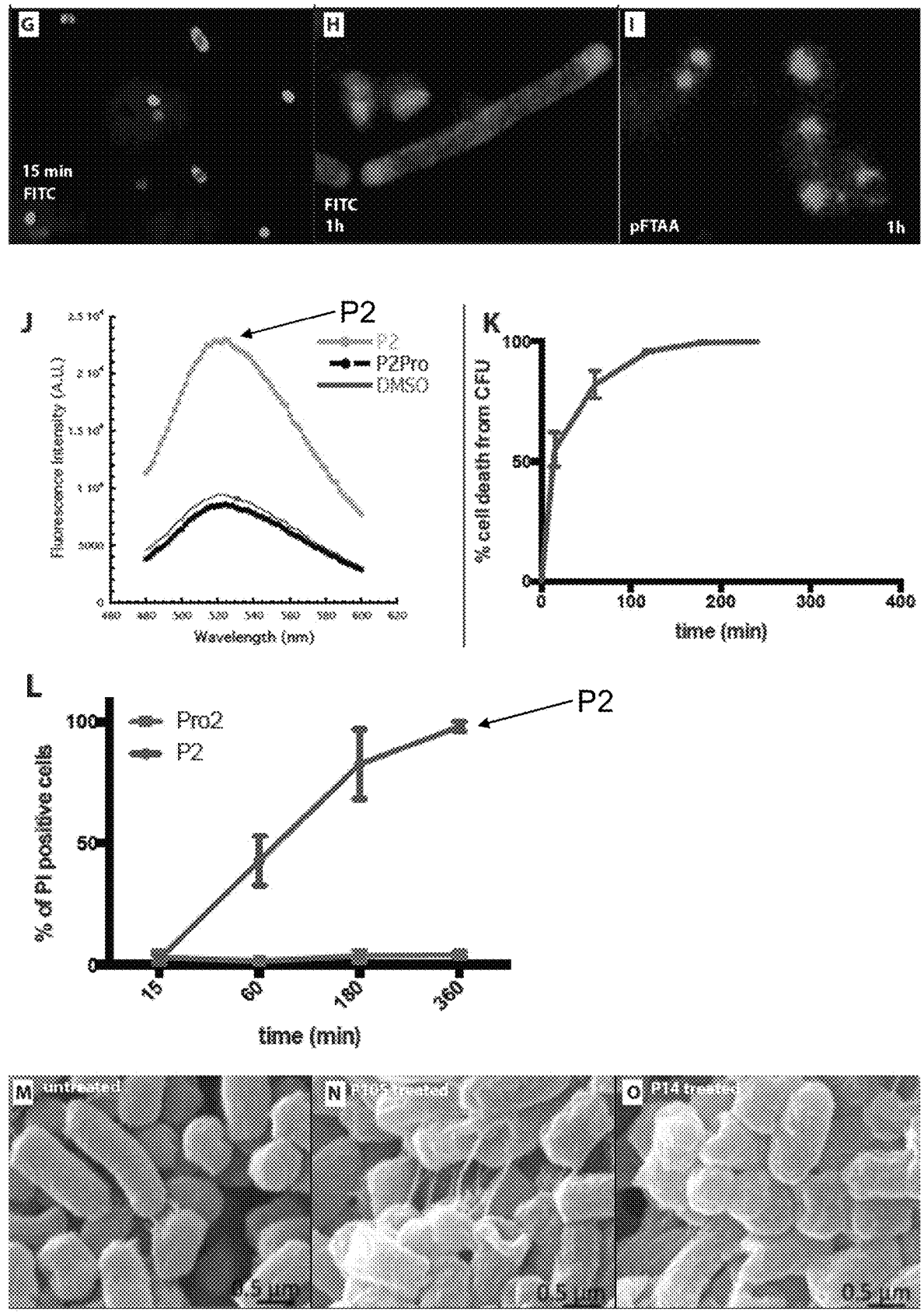

FIG. 3: Uptake and inclusion body formation. (A-E) Fluorescence Activated Cell Sorting (FACS) analysis of 10.000 E. coli O157 cells, measuring FITC fluorescence (x-axis) and Propidium Iodide Fluorescence (y-axis) of: (A) Untreated and heat inactivated bacteria mixed 1:1, (B) of bacteria treated for 15 min with FITC-labelled colpeptin1. (C) Treated for 1 h. (D) Treated for 3 h. (E) Treated for 6 h. (F) Average population sizes of FITC-positive cells from four independent experiments such as shown in A-E. (G) Fluorescence microscopy image of E. coli treated with FITC-Colpeptin1 for 15 min and (H) for 1 hour. (1) Fluorescence microscopy image of E. coli O157 treated with Colpeptin1 and pFTAA. (J) Fluorescence emission spectrum of the amyloid specific dye pFTAA in E. coli O157 treated with buffer, the non-aggregating P2-Pro and Colpeptin1 (P2). (average of 3 repeats) (K) Timing dependent effect of Colpeptin1 on colony formation. (L) Average population sizes of PI-positive cells from four independent FACS experiments such as shown in A-E. (M-O) Scanning electron microscopy (SEM) of E. coli O157. (M) are images of mock treated bacteria, (N) of P105-treated and (O) of P14-treated E. coli O157.

Figure 4:
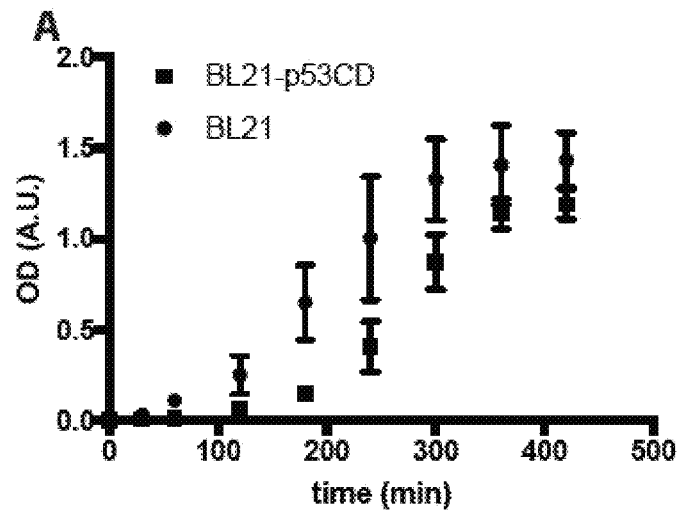
Figure 4:
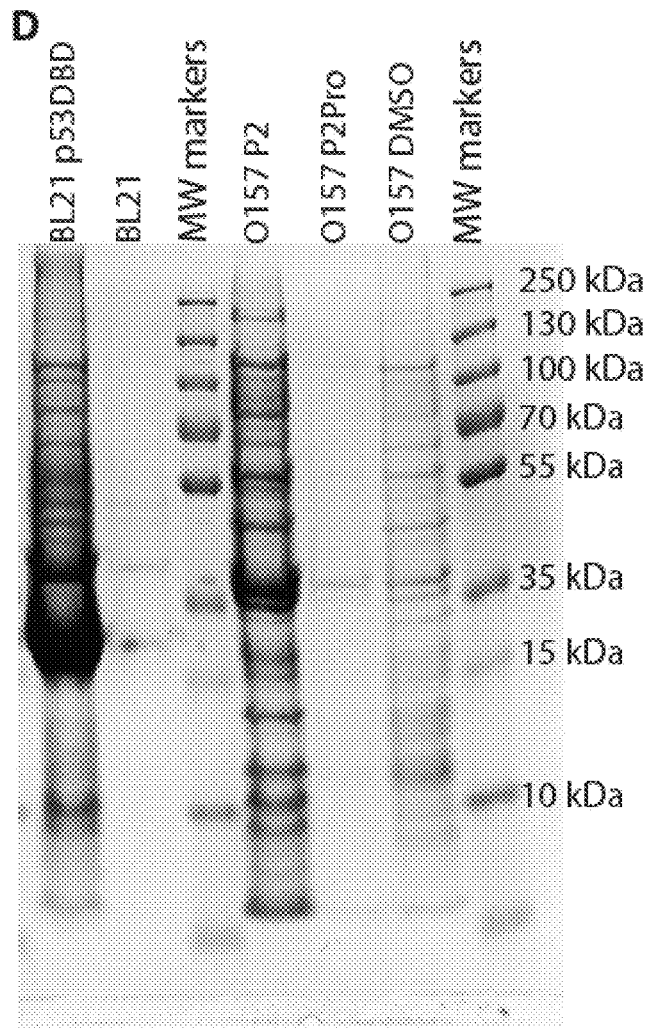
Figure 4:
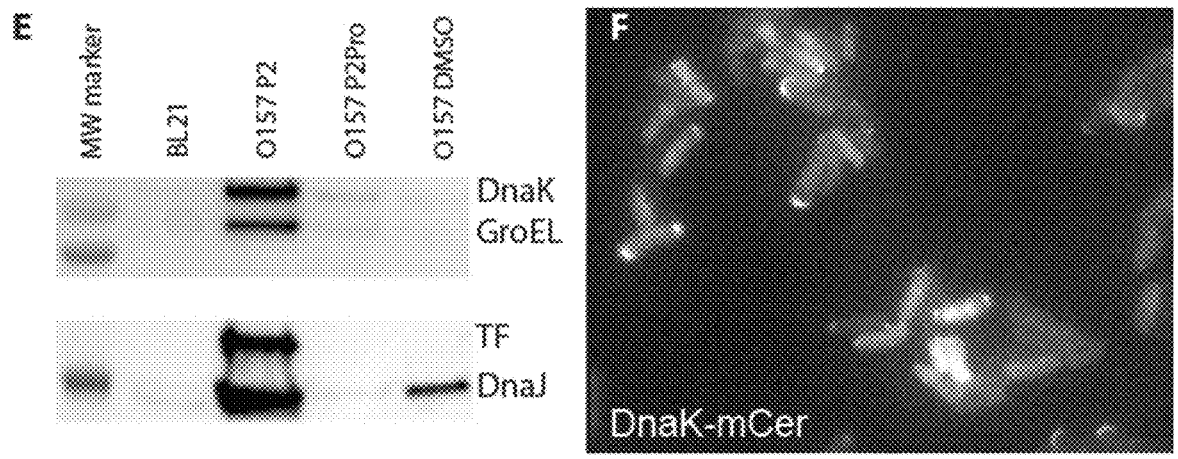
Figure 4:
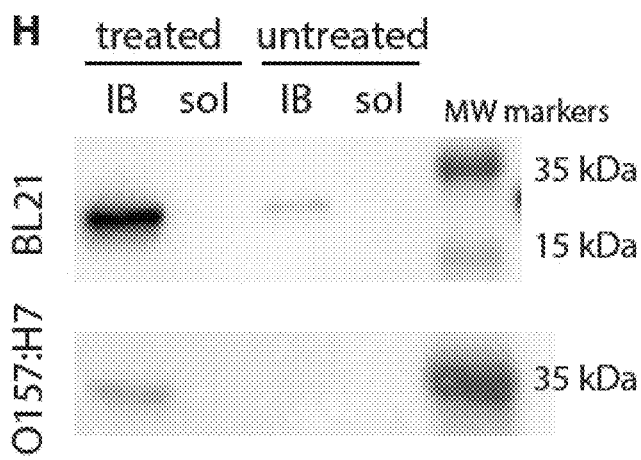
Figure 4:
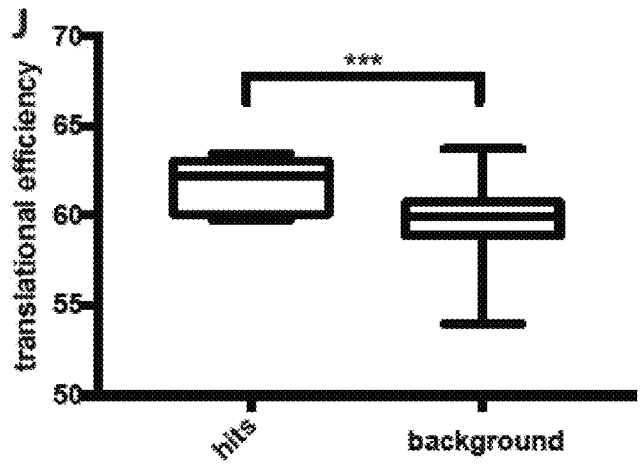

FIG. 4: Characterisation of Colpeptin1 and p53CD inclusion bodies. (A) Growth curve of bacteria overexpressing p53CD and untransformed controls. (average and s.d. of 3 replicates), (D) Coomassie staining of SDS-PAGE of inclusion bodies purified from E. coli O157 treated with Colpeptin1, P2Pro or buffer, and for comparison E. coli BL21 regular and transiently overexpressing the core domain the human p53 protein. (E) Western blot analysis of the same samples as in D. (F) Fluorescence image of E. coli cells stably expressing a fluorescent fusion of DnaK (mCer) treated with Colpeptin1. (H) Western blot of the soluble and insoluble fraction of bacteria treated with Colpeptin1 using the antibody raised against recombinantly produced HcaB. (J) Calculated translational efficiency (according to Tuller et al[35]) of proteins predicted to coaggregate with Colpeptin1.

Figure 5:

FIG. 5: Body weights of the treated mice by Colpeptin1 after 18 days injection via IP.

Figure 6:
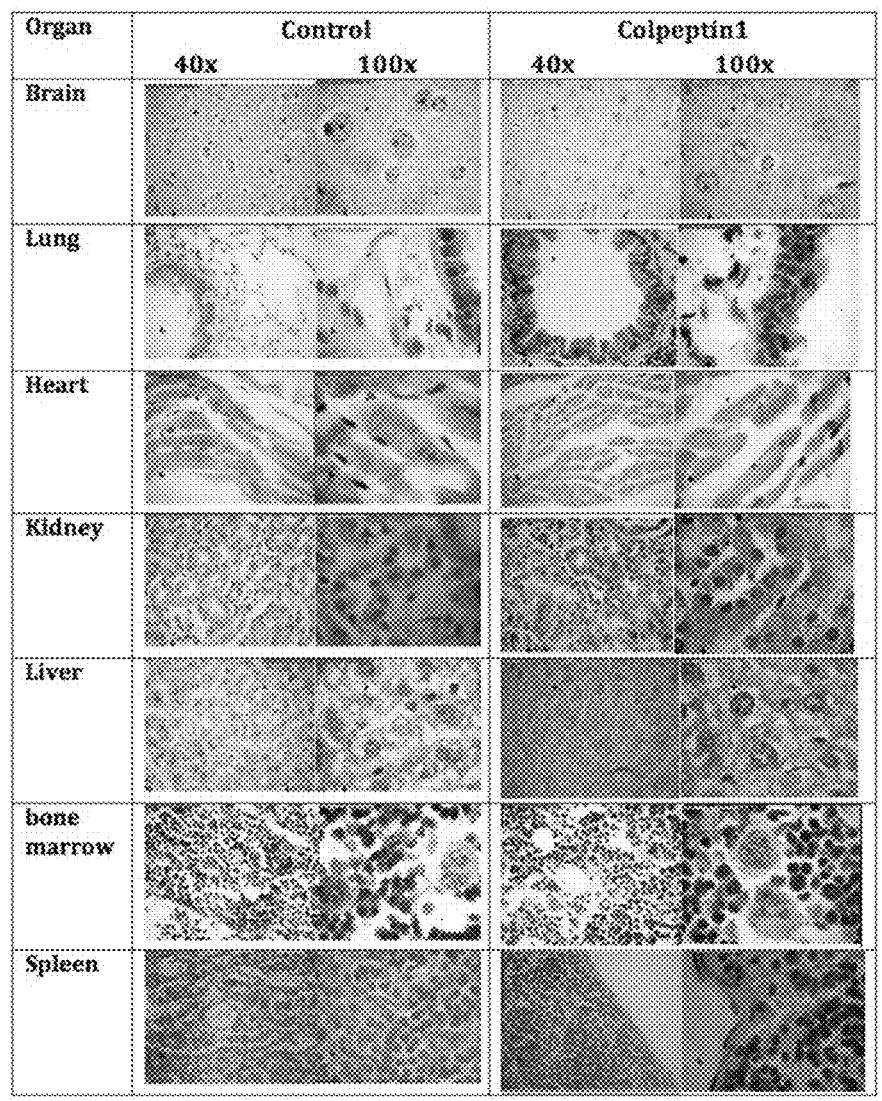

FIG. 6: Pathological analysis of tissue sections of mice treated with 30 mg/kg Colpeptin1 for 18 consecutive days.

Figure 7:
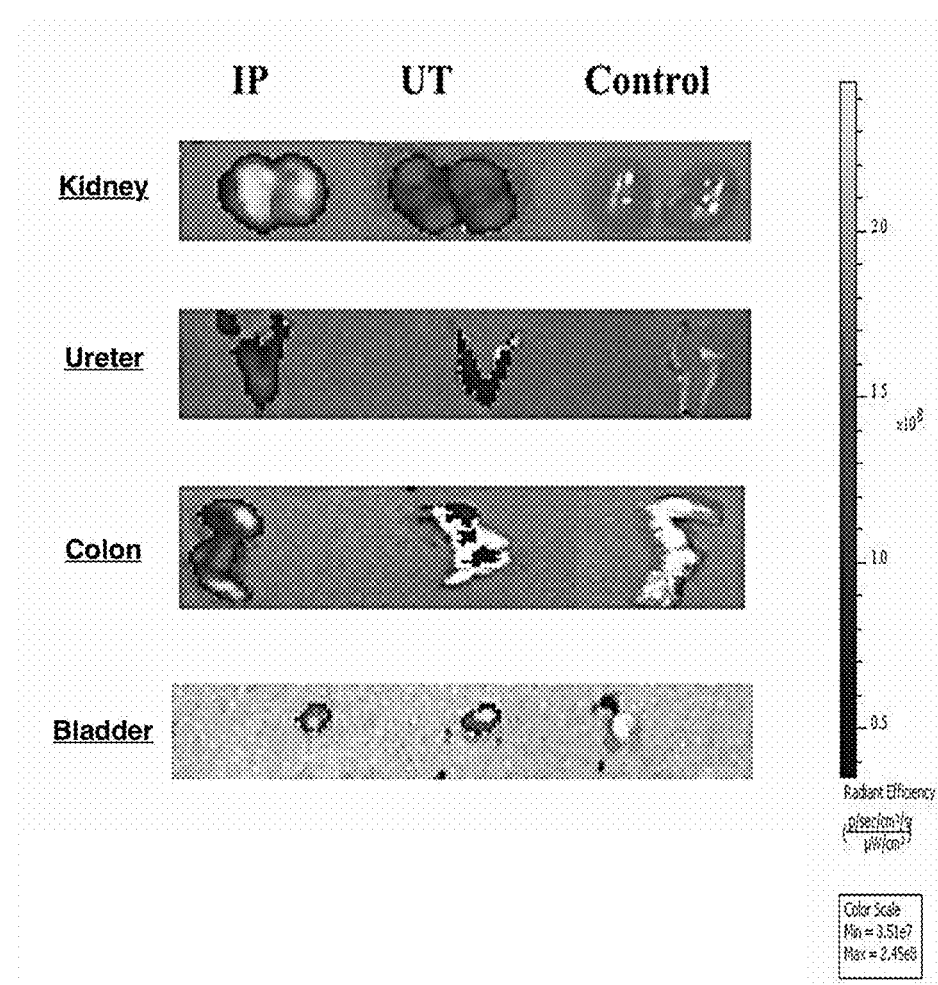

FIG. 7: Fluorescence imaging of organs ex vivo 3 h after a single injection (10 mg/kg) of Colpeptin1.

FIG. 8: a set of 28 peptides, which sequences are depicted in Table 4, were administered to the E. coli BL2 strain, Acinetobacter baumannii, Klebsiella pneumoniae and Pseudomonas aeruginosa. The MIC values are depicted.

Figure 9:
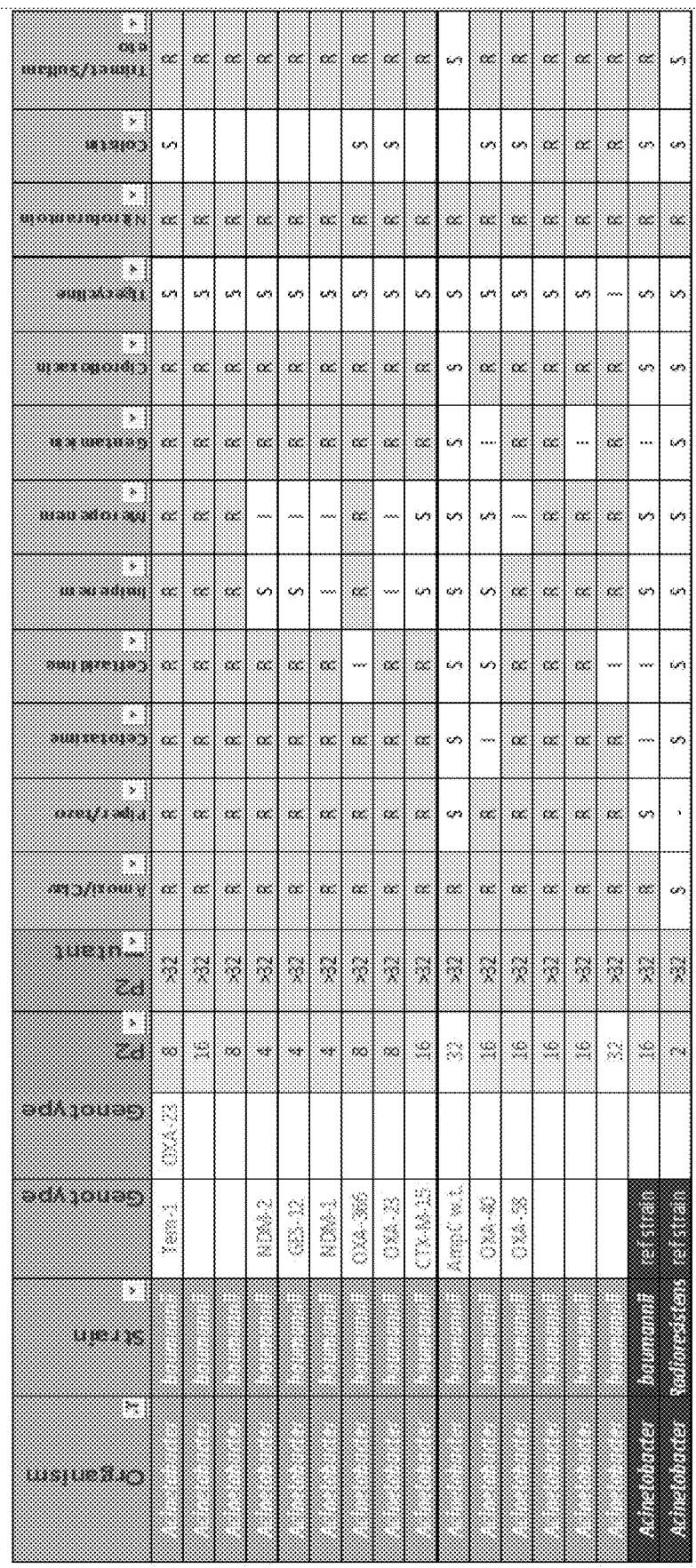

FIG. 9: The upper panel lists the activity (MIC values) of Colpeptin1 (P2 in the figure) against a number of clinical isolates of *E. coli*. Sensitivity (S) or resistance (R) or intermediate resistance (I) of the clinical isolates against 12 different antibiotics is depicted in the panel (data according to CLSI criteria for the specific antibiotics). MIC values <32 µg/ml are considered active. 32 µg/ml of colpeptin1 was the highest concentration tested. The lower panel lists the activity (MIC values) of Colpeptin1 (P2 in the figure) against a number of clinical isolates of *A. baumannii*. Sensitivity (S) or resistance (R) or intermediate resistance (1) of the clinical isolates against 12 different antibiotics is depicted in the panel (data according to CLSI criteria for the specific antibiotics). MIC values <32 µg/ml are considered active. 32 µg/ml of colpeptin1 was the highest concentration tested. The reference to P2 mutant means a variant non-active sequence derived from Colpeptin1 which is described in Table 1.

DETAILED DESCRIPTION TO THE INVENTION

The present invention will be described with respect to particular embodiments and with reference to certain figures but the invention is not limited thereto but only by the claims. Any reference signs in the claims shall not be construed as limiting the scope. Of course, it is to be understood that not necessarily all aspects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other aspects or advantages as may be taught or suggested herein.

The invention, both as to organization and method of operation, together with features and advantages thereof, may best be understood by reference to the following detailed description when read in conjunction with the accompanying figures. The aspects and advantages of the invention will be apparent from and elucidated with reference to the embodiment(s) described hereinafter. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment.

Where an indefinite or definite article is used when referring to a singular noun e.g. "a" or "an", "the", this includes a plural of that noun unless something else is specifically stated. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments, of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 4$^{th}$ ed., Cold Spring Harbor Press, Plainsview, New York (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "polypeptide" and "peptide" are interchangeably used further herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers. This term also includes post-translational modifications of the polypeptide, such as glycosylation, phosphorylation, amidation, oxidation and acetylation. By "recombinant polypeptide" is meant a polypeptide made using recombinant techniques, i.e., through the expression of a recombinant or synthetic polynucleotide. The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product. The term "recombinant host cell", "engineered cell", "expression host cell", "expression host system", "expression system" or simply "host cell", as used herein, is intended to refer to a cell into which a recombinant vector and/or chimeric gene construct has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. The term "modulate," "modulates," or "modulation" refers to enhancement (e.g. an increase) or inhibition (e.g. a decrease) in the specified level or activity. The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

The term "contact" or grammatical variations thereof as used with respect to a non-naturally occurring peptide or variants thereof of the invention and a bacterial isolate refers to bringing the non-naturally occurring peptide (or a variant thereof) and the bacterial isolate in sufficiently close proximity to each other for one to exert a biological effect on the other. In some embodiments, the term contact means binding of the specialized non-naturally occurring peptide to a bacterial isolate. A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject. By the terms "treat," "treating," or "treatment of," it is intended that the severity of the subject's condition is reduced or at least partially improved or modified and that some alleviation, mitigation or decrease in at least one clinical symptom is achieved. As used herein, a "functional" peptide is one that substantially retains at least one biological activity normally associated with that peptide (e.g. binding to and inhibiting the growth of a bacterium (or killing a bacterium). In particular embodiments, the "functional" peptide substantially retains all of the activities possessed by the unmodified peptide. By "substantially retains" biological activity, it is meant that the peptide retains at least about 20%, 30%, 40%, 50%, 60%, 75%, 85%, 90%, 95%, 97%, 98%, 99%, or more, of the biological activity of the native polypeptide (and can even have a higher level of activity than the native peptide). Biological activities such as protein binding and bacterial inhibitory activity can be measured using assays described herein and other assays that are well known in the art.

As used herein the term "conservative amino acid substitution" refers to the substitution of an amino acid that is normally present in the peptide sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

The present invention provides a novel designer antibiotics paradigm that exploits aggregation to inhibit the growth (and/or to kill) pathogenic bacteria by widespread proteostatic collapse. Specifically we identified a number of non-naturally occurring peptides, which contain a short aggregation-nucleating sequence that are redundant in the proteome of E. coli. Analysis of the mode of action of a specific representative member, designated herein further as colpeptin1, revealed that the peptides are rapidly and efficiently internalized by E. coli as 98% of the cells were positive within 15 min. Colpeptin1 uptake readily resulted in the formation of large polar inclusion bodies and bacterial cell death with about 50% cell death in 15 min and more than 80% after 1 h. The fast and lethal aggregation-associated bacterial cell death observed here is surprising as IB formation is generally a non-lethal and reversible response to acute stress in bacteria. Moreover repeated passaging of bacteria on sublethal concentrations (50% of MIC) of the active peptides for a period of 36 days did not result in the development of resistance contrary to the control antibiotic ampicillin. In addition, the peptides are active in vivo, indeed colpeptin1 effectively reduces the bacterial load in a mouse bladder infection model without adverse effects to its host. The present invention provides non-naturally occurring peptides, such as colpeptin1 and variants thereof, and methods for producing variant or similar peptides for treating pathogenic bacteria, such as for combatting difficult to treat pathogenic bacteria. Indeed, our invention shows that it is possible to exploit the sequence specificity of aggregation-prone peptide segments in proteins in bacteria to simultaneously hit several protein targets thereby resulting in fast bacterial cell death. This approach therefore represents an interesting paradigm to develop a novel class of antibiotics.

Accordingly, the invention provides in a first aspect, a non-naturally occurring anti-bacterial peptide configured to induce aggregation of one or more primary target proteins of a bacterium such as to form inclusion bodies comprising said one or more primary target proteins in said bacterium, wherein the one or more primary target proteins of said bacterium include the 3-phenylpropionate-dihydrodiol/cinnamic acid-dihydrodiol dehydrogenase (Hcab) protein.

In certain embodiments, the one or more primary target proteins of said bacterium further include:
chaperone protein skp (Skp), phosphate regulon sensor protein (PhoR), dipeptide and tripeptide permease A (Dtpa), probable sensor-like histidine kinase YedV (YedV), uncharacterized Na(+)/H(+) exchanger YjcE (YjcE), osmolarity sensor protein EnvZ (EnvZ), sensor protein RstB (RstB), sensor protein ZraS (ZraS), putative uncharacterized protein YbfO (YbfO), sensor histidine kinase DcuS (DcuS), signal transduction histidine-protein kinase AtoS (AtoS), formate hydrogenlyase subunit 4 (hycD), aromatic amino acid exporter YddG (YddG), UPF0226 protein YfcJ (YfcJ), and inner membrane protein yfeZ (YfeZ);
one or more proteins selected from the group consisting of the proteins listed in Table 8; and/or
one or more proteins selected from the group consisting of the proteins listed in Table 9.

In certain embodiments, the peptide induces aggregation of said one or more primary target proteins of said bacterium by co-aggregating with one or more aggregation-prone regions (APRs) in said one or more primary target proteins. In certain embodiments, the amino acid sequence of said one or more APRs is GLGLALV (SEQ ID NO: 128) or displays a single mismatch compared to GLGLALV (SEQ ID NO: 128).

In certain embodiments, the peptide induces aggregation of said one or more primary target proteins of said bacterium by co-aggregating with one or more APRs selected from the group consisting of: GLGLALV (SEQ ID NO: 128), GLGLALA (SEQ ID NO: 202), GLGLAIV (SEQ ID NO: 203), GLGLAMV (SEQ ID NO: 204), GLGLSLV (SEQ ID NO: 205), GLALALV (SEQ ID NO: 206), GLGLAV (SEQ ID NO: 207), GLPLALV (SEQ ID NO: 208), GVGLALV (SEQ ID NO: 209), GLGLALS (SEQ ID NO: 210), GLL-

LALV (SEQ ID NO: 211), GLGLALQ (SEQ ID NO: 212), GIGLALV (SEQ ID NO: 213).

In certain embodiments, the bacterium is Gram-negative, preferably *Escherichia* or *Acinetobacter*, more preferably *Escherichia coli*, *Acinetobacter radioresistens* or *Acinetobacter baumanii*.

In certain embodiments, the peptide shows Minimum Inhibitory Concentration (MIC) against said bacterium of less than 32 µg/ml, such as 25 µg/mL or less, 12 µg/mL or less, or 6 µg/mL or less.

In certain embodiments, the peptide comprises sequence $X_1$-$X_2$-$X_3$-$X_4$-$X_5$-$X_6$-$X_7$ configured to coaggregate with said one or more APRs, wherein:

$X_1$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_2$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_3$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_4$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_5$ is alanine or a conservative amino acid substitution of alanine or a non-natural amino acid variant of alanine or a D-amino acid of alanine or a D-amino acid of a conservative amino acid substitution of alanine or a D-amino acid of a non-natural amino acid variant of alanine, $X_6$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, and $X_7$ is valine or a conservative amino acid substitution of valine or a non-natural amino acid variant of valine or a D-amino acid of valine or a D-amino acid of a conservative amino acid substitution of valine or a D-amino acid of a non-natural amino acid variant of valine.

In certain embodiments, the peptide comprises one or more D-amino acids and/or non-natural amino acids.

In certain embodiments, the peptide comprises the following structure: $(A_{2i-1}$-$X_1$-$X_2$-$X_3$-$X_4$-$X_5$-$X_6$-$X_7$-$A_{2i}$-$Z_i)_n$, wherein:

n is an integer from 1 to 4 and i increases from 1 to n with each repeat;

each $A_{2i-1}$ and $A_{2i}$ are independently selected from 1 to 3 contiguous gatekeepers, wherein the amino-terminal gatekeeper in the peptide structure is optionally acetylated and/or wherein the carboxy-terminal gatekeeper in the peptide sequence is optionally amidated, $X_1$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_2$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_3$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_4$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_5$ is alanine or a conservative amino acid substitution of alanine or a non-natural amino acid variant of alanine or a D-amino acid of alanine or a D-amino acid of a conservative amino acid substitution of alanine or a D-amino acid of a non-natural amino acid variant of alanine, $X_6$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_7$ is valine or a conservative amino acid substitution of valine or a non-natural amino acid variant of valine or a D-amino acid of valine or a D-amino acid of a conservative amino acid substitution of valine or a D-amino acid of a non-natural amino acid variant of valine, and wherein $X_1$—$X_2$-$X_3$-$X_4$-$X_5$-$X_6$-$X_7$ and $X_7$—$X_6$-$X_5$-$X_4$-$X_3$-$X_2$-$X_1$ are used interchangeably in the repeats wherein n is 2 to 4, and each $Z_i$ is a linker.

Hence, also provided as a related aspect is a peptide comprising the following structure: $(A_{2i-1}$-$X_1$-$X_2$-$X_3$-$X_4$-$X_5$-$X_6$-$X_7$-$A_{2i}$-$Z_i)_n$, wherein:

n is an integer from 1 to 4 and i increases from 1 to n with each repeat;

each $A_{2i-1}$ and $A_{2i}$ are independently selected from 1 to 3 contiguous gatekeepers, wherein the amino-terminal gatekeeper in the peptide structure is optionally acetylated and/or wherein the carboxy-terminal gatekeeper in the peptide sequence is optionally amidated, $X_1$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_2$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_3$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_4$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_5$ is alanine or a conservative amino acid substitution of alanine or a non-natural amino acid variant of alanine or a D-amino acid of alanine or a D-amino acid of a conservative amino acid substitution of alanine or a D-amino acid of a non-natural amino acid variant of alanine, $X_6$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_7$ is valine or a conservative amino acid substitution of valine or a non-natural amino acid variant of valine or a D-amino acid of valine or a D-amino acid of a conservative amino acid substitution of valine or a D-amino acid of a non-natural amino acid variant of valine, and wherein $X_1-X_2-X_3-X_4-X_5-X_6-X_7$ and $X_7-X_6-X_5-X_4-X_3-X_2-X_1$ are used interchangeably in the repeats wherein n is 2 to 4, and each $Z_i$ is a linker.

In certain embodiments, each $A_{2i-1}$ and $A_{2i}$ are independently selected from 1 to 3 contiguous gatekeeper amino acids selected from R, K, D, E, P and/or 1 to 3 non-natural gatekeeper amino acids.

In certain embodiments, each $Z_i$ is independently selected from stretch of between 1 and 5 units, wherein a unit is PEG, an amino acid or a non-natural amino acid.

In certain embodiments, one or more amino acids of $A_{2i-1}$, $A_{2i}$, $X_1-X_2-X_3-X_4-X_5-X_6-X_7$, and/or $Z_i$ is a D-amino acid and/or a non-natural amino acid.

Also provided is a peptidomimetic generated from said peptide.

In certain embodiments, the peptide or peptidomimetic further comprises a detectable label.

In certain embodiments, the peptide or peptidomimetic further comprises a molecule which increases the half-life extension.

In certain embodiments, the peptide or peptidomimetic further comprises a moiety that increases solubility of the molecule.

In certain embodiments, the peptide or peptidomimetic displays anti-bacterial effects against more than one bacterial taxon, such as more than one bacterial genus, species or strain.

Further provided are independently:
the peptide or peptidomimetic for use as a medicine;
the peptide or peptidomimetic for use as an anti-bacterial agent; and a corresponding method of treatment of a bacterial infection using the peptide or peptidomimetic;
the peptide or peptidomimetic for use as a diagnostic agent; and a corresponding method of diagnosis using the peptide or peptidomimetic; or
a pharmaceutical composition comprising the peptide or peptidomimetic and a pharmaceutically acceptable carrier.

The invention further provides in a second aspect, a non-naturally occurring anti-bacterial peptide configured to induce aggregation of one or more primary target proteins of a bacterium such as to form inclusion bodies comprising said one or more primary target proteins in said bacterium, wherein the one or more primary target proteins of said bacterium include a protein selected from the proteins listed in Table 4.

In certain embodiments, the peptide induces aggregation of said one or more primary target proteins of said bacterium by co-aggregating with one or more aggregation-protein segments (APRs) in said one or more primary target proteins.

In certain embodiments, the amino acid sequence of said one or more APRs is as listed in Table 4 or displays a single mismatch compared thereto.

In certain embodiments, the bacterium is Gram-negative, preferably *Escherichia* or *Acinetobacter*, more preferably *Escherichia coli*, *Acinetobacter radioresistens* or *Acinetobacter baumanii*.

In certain embodiments, the peptide shows Minimum Inhibitory Concentration (MIC) against said bacterium of less than 32 µg/ml, such as 25 µg/mL or less, 12 µg/mL or less, or 6 µg/mL or less.

In certain embodiments, the peptide comprises the following structure: $(A_2 11\text{-APR-}A_2\text{-}Z_i)_n$, wherein:

n is an integer from 1 to 4 and i increases from 1 to n with each repeat;

each $A_{2i-1}$ and $A_{2i}$ are independently selected from 1 to 3 contiguous gatekeepers, wherein the amino-terminal gatekeeper in the peptide structure is optionally acetylated and/or wherein the carboxy-terminal gatekeeper in the peptide sequence is optionally amidated, the names of the peptides comprised in APR are depicted in Table 5 (P3, P4, P5, P12, P14, P16, P18, P23, P26, P29, P33, P39, P40, P49, P50, P58, P72, P76, P79, P80, P87, P88, P89, P90, P91, P92, P93, P99, P101, P103, P105, P111, P112, P113, P114, P115, P116, P117, P118, P123, P124 and P125) and the corresponding amino acid sequences for these peptides are depicted in Table 4 wherein APR comprises natural amino acids or APR comprises conservative amino acid substitutions of the amino acids present in APR or APR comprises non-natural amino acid analogues of the amino acids present in the peptide sequences present in APR or APR comprises D-amino acid substitutions in the peptide sequences of the amino acids present in APR, and wherein the amino acids in APR can be in a direct or inverted repeat wherein n is 2 to 4, and each $Z_i$ is a linker.

Hence, also provided as a related aspect is a peptide comprising the following structure: $(A_{2i-1}\text{-APR-}A_{2i}\text{-}Z_i)_n$, wherein:

n is an integer from 1 to 4 and i increases from 1 to n with each repeat;

each $A_{2i-1}$ and $A_{2i}$ are independently selected from 1 to 3 contiguous gatekeepers, wherein the amino-terminal gatekeeper in the peptide structure is optionally acetylated and/or wherein the carboxy-terminal gatekeeper in the peptide sequence is optionally amidated, the names of the peptides comprised in APR are depicted in Table 5 (P3, P4, P5, P12, P14, P16, P18, P23, P26, P29, P33, P39, P40, P49, P50, P58, P72, P76, P79, P80, P87, P88, P89, P90, P91, P92, P93, P99, P101, P103, P105, P111, P112, P113, P114, P115, P116, P117, P118, P123, P124 and P125) and the corresponding amino acid sequences for these peptides are depicted in Table 4 wherein APR comprises natural amino acids or APR comprises conservative amino acid substitutions of the amino acids present in APR or APR comprises non-natural amino acid analogues of the amino acids present in the peptide sequences present in APR or APR comprises D-amino acid substitutions in the peptide sequences of the amino acids present in APR, and wherein the amino acids in APR can be in a direct or inverted repeat wherein n is 2 to 4, and each $Z_i$ is a linker.

In certain embodiments, each $A_{2i-1}$ and $A_{2i}$ are independently selected from 1 to 3 contiguous gatekeeper amino acids selected from R, K, D, E, P and/or 1 to 3 non-natural gatekeeper amino acids.

In certain embodiments, each $Z_i$ is independently selected from stretch of between 1 and 5 units, wherein a unit is PEG, an amino acid or a non-natural amino acid.

In certain embodiments, one or more amino acids of $A_{2i-1}$, $A_{2i}$, APR, and/or $Z_i$ is a D-amino acid and/or a non-natural amino acid.

In certain embodiments, the peptide further comprises a detectable label.

In certain embodiments, the peptide further comprises a molecule which increases the half-life extension.

In certain embodiments, the peptide further comprises a moiety that increases solubility of the molecule.

Further provided are independently:
the peptide for use as a medicine;
the peptide for use as an anti-bacterial agent, and a corresponding method of treatment of a bacterial infection using the peptide;
the peptide for use as a diagnostic agent; and a corresponding method of diagnosis using the peptide; or
a pharmaceutical composition comprising the peptide and a pharmaceutically acceptable carrier.

The invention further provides in an embodiment a peptide comprising the following structure: $(A_{2i-1}\text{-APR-}A_{2i}\text{-}Z_i)_n$, wherein:

n is an integer from 1 to 4 and i increases from 1 to n with each repeat;

each $A_{2i-1}$ and $A_{2i}$ are independently selected from 1 to 3 contiguous gatekeeper amino acids selected from R, K, D, E and P and/or 1 to 3 non-natural gatekeeper amino acid selected from 3-methylproline, 3,4-dehydro-proline, 2-[(2S)-2-(hydrazinecarbonyl)pyrrolidin-1-yl]-2-oxoacetic acid, beta-homoproline, alpha-methyl-proline, hydroxyproline, 4-oxo-proline, beta,beta-dimethyl-proline, 5,5-dimethyl-proline, 4-cyclohexyl-proline, 4-phenyl-proline, 3-phenyl-proline, 4-aminoproline, 4-mercaptoproline, 2-amino-adipic acid (homoglutamic acid), 2-amino-heptanedioic acid (2-aminopimelic acid), 2-amino-octanedioic acid (aminosuberic acid), 2-amino-4-carboxy-pentanedioic acid (4-carboxyglutamic acid), glyoxal-hydroimidazolone, methylglyoxal-hydroimidazolone, N-alpha-methyl-arginine, omega-methyl-arginine, norarginine, homoarginine, N,N'-diethyl-homoarginine, beta-homoarginine, 2-amino-3-ureido-propionic acid, 2-amino-6-(1-carboxyethylamino)hexanoic acid, 2-amino-6-carboxymethylamino)hexanoic acid, 2-amino-6-(2-(furan-2-yl)-2-oxoethylamino)hexanoic acid, 2-amino-6-(formyl-5-hydroxymethyl-pyrrol-1-yl)-hexanoic acid, c-alpha-methyl-lysine, beta,beta-dimethyl-lysine, N-epsilon-formyl-lysine, N-epsilon-methyl-lysine, N-epsilon-i-propyl-lysine, N-epsilon-dimethyl-lysine, N-epsilon-trimethylamonium-lysine, N-epsilon-nicotinyl-lysine, {[5-amino-1-(hydrazinecarbonyl)pentyl]carbamoyl}formic acid, N-alpha-methyl-lysine, homolysine, beta-homolysine, 2-Amino-6-diazo-5-oxocaproic acid, norvaline, alpha-methyl-norvaline, Hydroxinorvaline, Ornithine, N-delta-methyl-ornithine, N-delta-N-delta-dimethyl-ornithine, N-delta-i-propyl-ornithine, c-alpha-methyl-ornithine, beta,beta-dimethyl-ornithine, canavanine, N-delta-methyl-N-delta-butyl-ornithine, N-delta-methyl-N-delta-phenyl-ornithine, delta-(2-methylpyrrolidine)-ornithine, delta-piperidyl-ornithine, gamma-amino-delta-piperidyl-valeric acid and delta-azepanyl-ornithine and wherein the amino-terminal gatekeeper amino acid or amino-terminal non-natural gatekeeper amino acid in the peptide structure is optionally acetylated and/or wherein the carboxy-terminal gatekeeper amino acid or carboxy-terminal non-natural gatekeeper amino acid in the peptide sequence is optionally amidated;

the names of the peptides comprised in APR are depicted in Table 5 (P2, P3, P4, P5, P12, P14, P16, P18, P23, P26, P29, P33, P39, P40, P49, P50, P58, P72, P76, P79, P80, P87, P88, P89, P90, P91, P92, P93, P99, P101, P103, P105, P111, P112, P113, P114, P115, P116, P117, P118, P123, P124 and P125) and the corresponding amino acid sequences for these peptides are depicted in Table 4 wherein APR comprises natural amino acids or APR comprises conservative amino acid substitutions of the amino acids present in APR or APR comprises non-natural amino acid analogues of the amino acids present in the peptide sequences present in APR or APR comprises D-amino acid substitutions in the peptide sequences of the amino acids present in APR, and wherein the amino acids in APR can be in a direct or inverted repeat wherein n is 2 to 4;

and each $Z_i$ is a linker and wherein each $Z_i$ is independently selected from stretch of between 1 and 5 units, wherein a unit is PEG, an amino acid or a non-natural amino acid.

In yet another embodiment the invention provides the sequences depicted in Table 5 (P2, P3, P4, P5, P12, P14, P16, P18, P23, P26, P29, P33, P39, P40, P49, P50, P58, P72, P76, P79, P80, P87, P88, P89, P90, P91, P92, P93, P99, P101, P103, P105, P111, P112, P113, P114, P115, P116, P117, P118, P123, P124 and P125) and the corresponding amino acid sequences for these peptides are depicted in Table 4.

The invention provides in a further embodiment a peptide comprising the following structure: $(A_{2i-1}\text{-}X_1\text{-}X_2\text{-}X_3\text{-}X_4\text{-}X_5\text{-}X_6\text{-}X_7\text{-}A_{2i}\text{-}Z_i)$, wherein:

n is an integer from 1 to 4 and i increases from 1 to n with each repeat;

each $A_{2i-1}$ and $A_{2i}$ are independently selected from 1 to 3 contiguous gatekeeper amino acids selected from R, K, D, E and P and/or 1 to 3 non-natural gatekeeper amino acid selected from 3-methylproline, 3,4-dehydro-proline, 2-[(2S)-2-(hydrazinecarbonyl)pyrrolidin-1-yl]-2-oxoacetic acid, beta-homoproline, alpha-methyl-proline, hydroxyproline, 4-oxo-proline, beta,beta-dimethyl-proline, 5,5-dimethyl-proline, 4-cyclohexyl-proline, 4-phenyl-proline, 3-phenyl-proline, 4-aminoproline, 4-mercaptoproline, 2-amino-adipic acid (homoglutamic acid), 2-amino-heptanedioic acid (2-aminopimelic acid), 2-amino-octanedioic acid (aminosuberic acid), 2-amino-4-carboxy-pentanedioic acid (4-carboxyglutamic acid), glyoxal-hydroimidazolone, methylglyoxal-hydroimidazolone, N-alpha-methyl-arginine, omega-methyl-arginine, norarginine, homoarginine, N,N'-diethyl-homoarginine, beta-homoarginine, 2-amino-3-ureido-propionic acid, 2-amino-6-(1-carboxyethylamino)hexanoic acid, 2-amino-6-carboxymethylamino)hexanoic acid, 2-amino-6-(2-(furan-2-yl)-2-oxoethylamino)hexanoic acid, 2-amino-6-(formyl-5-hydroxymethyl-pyrrol-1-yl)-hexanoic acid, c-alpha-methyl-lysine, beta,beta-dimethyl-lysine, N-epsilon-formyl-lysine, N-epsilon-methyl-lysine, N-epsilon-i-propyl-lysine, N-epsilon-dimethyl-lysine, N-epsilon-trimethylamonium-lysine, N-epsilon-nicotinyl-lysine, {[5-amino-1-(hydrazinecarbonyl)pentyl]carbamoyl} formic acid, N-alpha-methyl-lysine, homolysine, beta-homolysine, 2-Amino-6-diazo-5-oxocaproic acid, nor-valine, alpha-methyl-norvaline, Hydroxinorvaline, Ornithine, N-delta-methyl-ornithine, N-delta-N-delta-dimethyl-ornithine, N-delta-i-propyl-ornithine, c-alpha-methyl-ornithine, beta,beta-dimethyl-ornithine, canavanine, N-delta-methyl-N-delta-butyl-ornithine, N-delta-methyl-N-delta-phenyl-ornithine, delta-(2-methylpyrrolidine)-ornithine, delta-piperidyl-ornithine, gamma-amino-delta-piperidyl-valeric acid and delta-azepanyl-ornithine and wherein the amino-terminal gatekeeper amino acid or amino-terminal non-natural gatekeeper amino acid in the peptide structure is optionally acetylated and/or wherein the carboxy-terminal gatekeeper amino acid or carboxy-terminal non-natural gatekeeper amino acid in the peptide sequence is optionally amidated, $X_1$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_2$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_3$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_4$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_5$ is alanine or a conservative amino acid substitution of alanine or a non-natural amino acid variant of alanine or a D-amino acid of alanine or a D-amino acid of a conservative amino acid substitution of alanine or a D-amino acid of a non-natural amino acid variant of alanine, $X_6$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_7$ is valine or a conservative amino acid substitution of valine or a non-natural amino acid variant of valine or a D-amino acid of valine or a D-amino acid of a conservative amino acid substitution of valine or a D-amino acid of a non-natural amino acid variant of valine, and wherein $X_1-X_2-X_3-X_4-X_5-X_6-X_7$ and $X_7-X_6-X_5-X_4-X_3-X_2-X_1$ are used interchangeably in the repeats wherein n is 2 to 4, and each $Z_i$ is a linker and wherein each $Z_i$ is independently selected from stretch of between 1 and 5 units, wherein a unit is PEG, an amino acid or a non-natural amino acid.

The nature of the linker moieties, $Z_i$, in the peptides of the invention is not vital to the invention, although long flexible linkers are preferably not used. According to particular embodiments, each $Z_i$ is independently selected from a stretch of between 0 and 20 identical or non-identical units, wherein a unit is an amino acid, a monosaccharide, a nucleotide or a monomer. Non-identical units can be non-identical units of the same nature (e.g. different amino acids, or some copolymers). They can also be non-identical units of a different nature, e.g. a linker with amino acid and nucleotide units, or a heteropolymer (copolymer) comprising two or more different monomeric species. According to particular embodiments, the length of at least one, and particularly each $Z_i$ other than $Z_n$, is at least 1 unit. According to other particular embodiments, $Z_n$ is 0 units. According to particular embodiments, all $Z_i$ linkers other than $Z_n$ are identical.

According to further embodiments, all $Z_i$ moieties are identical.

According to specific embodiments, at least one, and particularly all, $Z_i$ are of between 0 and 10 units of the same nature, particularly between 0 and 5 units of the same nature. According to particular embodiments, at least one $Z_i$ moiety, and particularly all $Z_i$ moieties except $Z_n$, is a peptide or polypeptide linker. Particularly envisaged sequences of such linkers include, but are not limited to, PPP, PP or GS. The linker can also be of a chemical nature. Particularly envisaged chemical linkers include PEG and Ttds (aka 4,7,10-trioxatridecan-13-succinamic acid).

Typically, long linkers are not used. However, according to the particular embodiments where the aggregation-promoting moieties correspond to aggregation-inducing regions of more than one protein, it is envisaged that long linkers may be used. Indeed, to ensure that the molecule can (e.g. simultaneously) interact with more than one protein, it may be beneficial to increase the distance between the different targeting aggregation-promoting moieties, so that the interaction is not prevented due to steric hindrance. In these instances, the $Z_i$ linker may be a stretch of between 0 and 100 identical or non-identical units, wherein a unit is an amino acid, a monosaccharide, a nucleotide or a monomer; or of between 0 and 90, 0 and 80, 0 and 70, 0 and 60, 0 and 50, 0 and 40, 0 and 30 or 0 and 20. Particularly, the minimal length of the Zi linker is at least 1 unit, at least 2 units, at least 3 units, at least 4 units, or at least 5 units.

In yet another embodiment the invention provides a peptide comprising the following structure: $(A_{2i-1}-X_1-X_2-X_3-X_4-X_5-X_6-X_7-A_{2i}-Z_i)_n$, wherein:

n is an integer from 1 to 4 and i increases from 1 to n with each repeat;

each $A_{2i-1}$ and $A_{2i}$ are independently selected from 1 to 3 contiguous gatekeeper amino acids selected from R, K, D, E and P and/or wherein the amino-terminal gatekeeper amino acid is optionally acetylated and/or wherein the carboxy-terminal gatekeeper amino acid in the peptide sequence is optionally amidated, $X_1$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_2$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_3$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_4$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_5$ is alanine or a conservative amino acid substitution of alanine or a non-natural amino acid variant of alanine or a D-amino acid of alanine or a D-amino acid of a conservative amino acid substitution of alanine or a D-amino acid of a non-natural amino acid variant of alanine, $X_6$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_7$ is valine or a conservative amino acid substitution of valine or a non-natural amino acid variant of valine or a D-amino acid of valine or a D-amino acid of a conservative amino acid substitution of valine or a D-amino acid of a non-natural amino acid variant of valine, and wherein $X_1$-$X_2$-$X_3$-$X_4$-$X_5$-$X_6$-$X_7$ and $X_7$—$X_6$-$X_5$-$X_4$-$X_3$-$X_2$-$X_1$ are used interchangeably in the repeats wherein n is 2 to 4, and each $Z_i$ is a linker and wherein each $Z_i$ is independently selected from stretch of between 1 and 5 units, wherein a unit is PEG, an amino acid or a non-natural amino acid.

In yet another embodiment the invention provides a peptide comprising the following structure: $(A_{2i-1}$-$X_1$-$X_2$-$X_3$-$X_4$-$X_5$-$X_6$-$X_7$-$A_{2i}$-$Z_i)_n$, wherein:

n is an integer from 1 to 3 and i increases from 1 to n with each repeat;

each $A_{2i-1}$ and $A_{2i}$ are independently selected from 1 to 3 contiguous gatekeeper amino acids selected from R, K, D, E and P and wherein the amino-terminal gatekeeper amino acid is optionally acetylated and/or wherein the carboxy-terminal gatekeeper amino acid in the peptide sequence is optionally amidated, $X_1$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_2$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_3$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_4$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_5$ is alanine or a conservative amino acid substitution of alanine or a non-natural amino acid variant of alanine or a D-amino acid of alanine or a D-amino acid of a conservative amino acid substitution of alanine or a D-amino acid of a non-natural amino acid variant of alanine, $X_6$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_7$ is valine or a conservative amino acid substitution of valine or a non-natural amino acid variant of valine or a D-amino acid of valine or a D-amino acid of a conservative amino acid substitution of valine or a D-amino acid of a non-natural amino acid variant of valine, and wherein $X_1$—$X_2$-$X_3$-$X_4$-$X_5$-$X_6$-$X_7$ and $X_7$—$X_6$-$X_5$-$X_4$-$X_3$-$X_2$-$X_1$ are used interchangeably in the repeats wherein n is 2 to 4, and each $Z_i$ is a linker and wherein each $Z_i$ is independently selected from stretch of between 1 and 5 units, wherein a unit is PEG, an amino acid or a non-natural amino acid.

In yet another embodiment the invention provides a peptide comprising the following structure: $A_{2i-1}$-$X_1$-$X_2$-$X_3$-$X_4$-$X_5$-$X_6$-$X_7$-$A_{2i}$-$Z_i$, wherein:

each $A_{2i-1}$ and $A_{2i}$ are independently selected from 1 to 3 contiguous gatekeeper amino acids selected from R, K, D, E and P and wherein the amino-terminal gatekeeper amino acid is optionally acetylated and/or wherein the carboxy-terminal gatekeeper amino acid in the peptide sequence is optionally amidated, $X_1$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_2$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_3$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_4$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_5$ is alanine or a conservative amino acid substitution of alanine or a non-natural amino acid variant of alanine or a D-amino acid of alanine or a D-amino acid of a conservative amino acid substitution of alanine or a D-amino acid of a non-natural amino acid variant of alanine, $X_6$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_7$ is valine or a conservative amino acid substitution of valine or a non-natural amino acid variant of valine or a D-amino acid of valine or a D-amino acid of a conservative amino acid substitution of valine or a D-amino acid of a non-natural amino acid variant of valine, and each $Z_i$ is a linker and wherein each $Z_i$ is independently selected from stretch of between 1 and 5 units, wherein a unit is PEG, an amino acid or a non-natural amino acid.

In yet another embodiment the invention provides a peptide comprising the following structure: $(A_{2i-1}\text{-}X_1\text{-}X_2\text{-}X_3\text{-}X_4\text{-}X_5\text{-}X_6\text{-}X_7\text{-}A_{2i}\text{-}Z_i)_n$, wherein:

n is an integer from 1 to 2 and i increases from 1 to n with each repeat;

each $A_{2i-1}$ and $A_{2i}$ are independently selected from 1 to 3 contiguous gatekeeper amino acids selected from R, K, D, E and P and wherein the amino-terminal gatekeeper amino acid is optionally acetylated and/or wherein the carboxy-terminal gatekeeper amino acid in the peptide sequence is optionally amidated, X1 is glycine or a conservative amino acid substitution of glycine or a non-natural amino acid variant of glycine or a D-amino acid of a conservative amino acid substitution of glycine or a D-amino acid of a non-natural amino acid variant of glycine, X2 is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, X3 is glycine or a conservative amino acid substitution of glycine or a non-natural amino acid variant of glycine or a D-amino acid of a conservative amino acid substitution of glycine or a D-amino acid of a non-natural amino acid variant of glycine, X4 is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, X5 is alanine or a conservative amino acid substitution of alanine or a non-natural amino acid variant of alanine or a D-amino acid of alanine or a D-amino acid of a conservative amino acid substitution of alanine or a D-amino acid of a non-natural amino acid variant of alanine, X6 is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, X7 is valine or a conservative amino acid substitution of valine or a non-natural amino acid variant of valine or a D-amino acid of valine or a D-amino acid of a conservative amino acid substitution of valine or a D-amino acid of a non-natural amino acid variant of valine, and wherein $X_1$—$X_2$-$X_3$-$X_4$-$X_5$-$X_6$-$X_7$ and $X_7$—$X_6$-$X_5$-$X_4$-$X_3$-$X_2$-$X_1$ are used interchangeably in the repeats wherein n is 2, and each $Z_i$ is a linker and wherein each $Z_i$ is independently selected from stretch of between 1 and 5 units, wherein a unit is PEG, an amino acid or a non-natural amino acid.

In yet another embodiment the invention provides Colpeptin1 (P2) which sequence is depicted in SEQ ID NO: 1.

SEQ ID NO: 1: amino-RGLGLALVRRPRGLGLA-LVRR-carboxyl

In yet another embodiment $X_1$ and $X_3$ are selected from glycine or a non-natural variant of glycine selected from the list consisting of N-alpha-methyl-glycine (sarcosine), cyclopropylglycine and cyclopentylglycine, $X_2$, $X_4$ and $X_6$ are selected from leucine or valine or a non-natural variant of leucine selected from the list consisting of 2-amino-3,3-dimethyl-butyric acid (t-Leucine), alpha-methylleucine, hydroxyleucine, 2,3-dehydro-leucine, N-alpha-methyl-leucine, 2-Amino-5-methyl-hexanoic acid (homoleucine), 3-Amino-5-methylhexanoic acid (beta-homoleucine), 2-Amino-4,4-dimethyl-pentanoic acid (4-methyl-leucine, neopentylglycine), 4,5-dehydro-norleucine (allylglycine), L-norleucine, N-alpha-methyl-norleucine and 6-hydroxy-norleucine, $X_5$ is selected from alanine or a non-natural variant of alanine selected from the list consisting of 2-amino-isobutyric acid (2-Methylalanine), 2-Amino-2-methylbutanoic acid (Isovaline), N-alpha-Methyl-alanine, 2-Amino-2-methylpent-4-enoic acid (alpha-allylalanine), beta-homoalanine, 2-indanyl-glycine, Di-n-propyl-glycine, Di-n-butyl-glycine, Diethyl-glycine, (1-naphthyl)alanine, (2-naphthyl)alanine, cyclohexylglycine, adamantyl-glycine, beta-homoallylglycine and $X_7$ is selected from valine or leucine or a non-natural variant of leucine selected from the list consisting of c-alpha-methyl-valine (2,3-dimethylbutanoic acid), 2,3-dehydro-valine, 3,4-dehydro-valine, 3-methyl-L-isovaline (methylvaline), 2-amino-3-hydroxy-3-methylbutanoic acid (hydroxyvaline), beta-homovaline and N-alpha-methyl-valine.

The term "peptides of the invention" is conveniently used herein to encompass any peptides and peptide variants embodying the principles of the invention as disclosed herein, such as without limitation peptides based on colep-tin1 and variants thereof.

Specifically alanine analogues which can be used to develop variants of the peptides of the invention, such as variant peptides of SEQ ID NO: 1, by replacing at least one alanine in the structures of the peptides of the invention, such as in the structure of SEQ ID NO: 1, for an analogue of alanine are depicted in Table I:

TABLE I alanine analogues

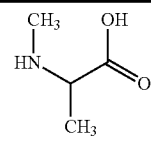

N-alpha-methyl-alanine

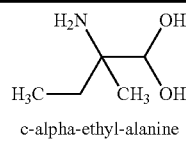

c-alpha-ethyl-alanine

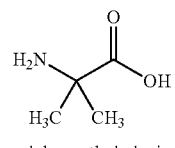

c-alpha-methyl-alanine

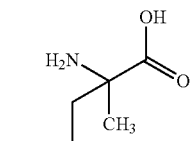

Amino-2-methylpent-4-enoic acid

TABLE I-continued alanine analogues

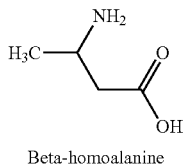
Beta-homoalanine

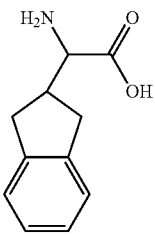
2-indanyl-glycine

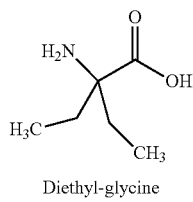
Diethyl-glycine

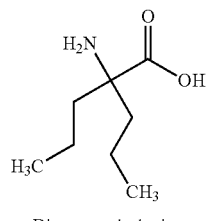
Di-n-propyl-glycine

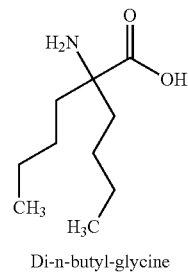
Di-n-butyl-glycine

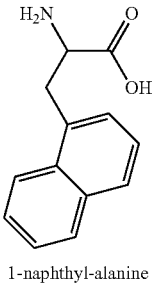 [SMILES: NC(Cc1cccc2ccccc12)C(=O)O]
1-naphthyl-alanine

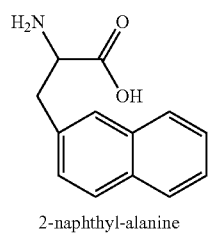
2-naphthyl-alanine

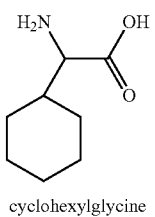
cyclohexylglycine

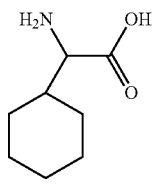
cyclohexylglycine

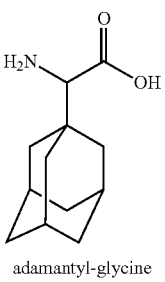
adamantyl-glycine

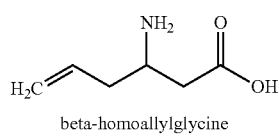
beta-homoallylglycine

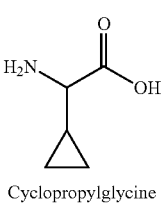
Cyclopropylglycine

TABLE I-continued alanine analogues

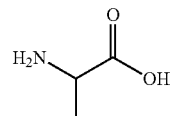
Cyclopentylglycine

Specifically arginine analogues which can be used to develop variants of the peptides of the invention, such as variants of SEQ ID NO: 1, by replacing at least one arginine in the structure in the peptides, such as in the structure of SEQ ID NO: 1, for an analogue of arginine are depicted in Table II:

TABLE II arginine analogues

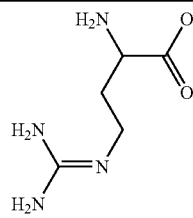

2-Amino-3-ureido-propionic acid | norarginine

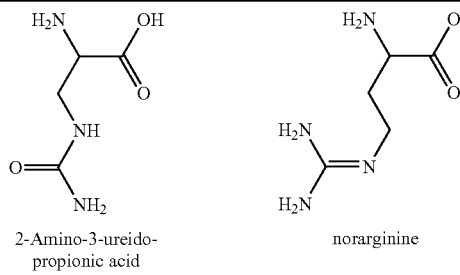

2-amino-3-guanidino-propionic acid | Methylglyoxal-hydroimidazolone

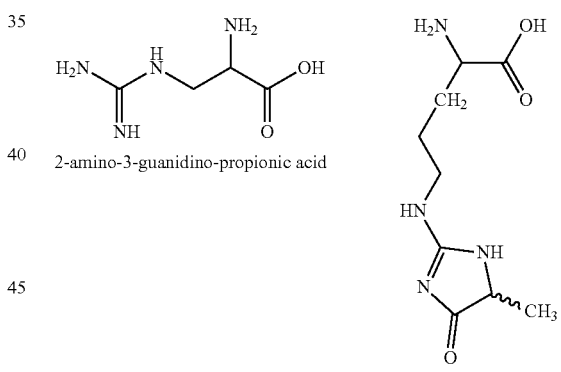

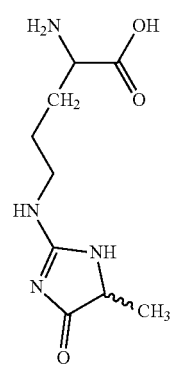

Glyoxal-hydroimidazolone | N'-nitro-arginine

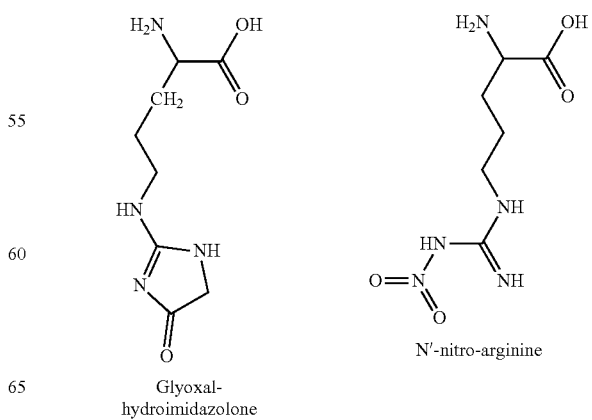

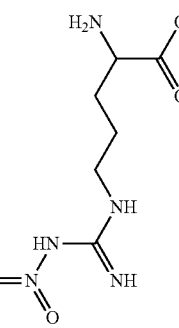

TABLE II-continued arginine analogues homoarginine omega-methyl-arginine

N-alpha-methyl-arginine

N,N'-diethyl-homoarginine

Beta-homoarginine

Specifically glycine analogues which can be used to develop variants of the peptides of the invention, such as variants of SEQ ID NO: 1, by replacing at least one glycine in the structure of the peptides, such as in the structure of SEQ ID NO: 1, for an analogue of glycine are depicted in Table III:

TABLE III glycine analogues

Sarcosine

In certain embodiments, specifically glycine analogues which can be used to develop variants of the peptides of the invention, such as variants of SEQ ID NO: 1, by replacing at least one glycine in the structure of the peptides, such as in the structure of SEQ ID NO: 1, may include beta-alanine or the analogues depicted in Table III, and may preferably be beta-alanine.

Specifically leucine analogues which can be used to develop variants of the peptides of the invention, such as variants of SEQ ID NO: 1, by replacing at least one leucine in the structure of the peptides, such as in the structure of SEQ ID NO: 1, for an analogue of leucine are depicted in Table IV:

TABLE IV leucine analogues

Hydroxyleucine

N-alpha-methyl-leucine 2,3-dehydro-leucine alpha-methyl-leucine

Homoleucine 4-methyl-leucine beta-homoleucine norleucine

TABLE IV-continued leucine analogues

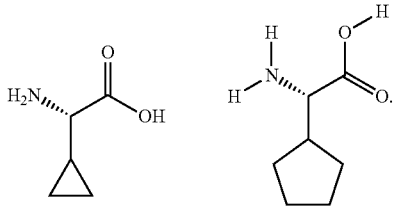 [SMILES: N[C@H](C(=O)O)C1CC1 ; N[C@H](C(=O)O)C1CCCC1]

4,5-dehydro-norleucine 6-hydroxy-norleucine

N-alpha-methyl-norleucine

2-Amino-3,3-dimethyl-butyric acid

In certain embodiments, specifically leucine analogues which can be used to develop variants of the peptides of the invention, such as variants of SEQ ID NO: 1, by replacing at least one leucine in the structure of the peptides, such as in the structure of SEQ ID NO: 1, for an analogue of leucine are depicted below:

In certain embodiments, specifically leucine analogues which can be used to develop variants of the peptides of the invention, such as variants of SEQ ID NO: 1, by replacing at least one leucine in the structure of the peptides, such as in the structure of SEQ ID NO: 1, for an analogue of leucine may be norvaline or alpha-methyl-norvaline.

Specifically valine analogues which can be used to develop variants of the peptides of the invention, such as variants of SEQ ID NO: 1, by replacing at least one valine in the structure of the peptides, such as in the structure of SEQ ID NO: 1, for an analogue of valine are depicted in Table V:

TABLE V valine analogues c-alpha-methyl-valine 2,3-dehydro-valine 3,4-dehydro-valine hydroxyvaline beta-homovaline N-alpha-methyl-valine Specifically lysine analogues which can be used to develop peptides of the invention by replacing the gatekeeper residue lysine (K) for an analogue of lysine (K) are depicted in Table VI:

TABLE VI lysine analogues

N-epsilon-formyl-L-lysine

N-epsilon-methyl-lysine

N-epsilon-i-propyl-lysine

TABLE VI-continued
lysine analogues
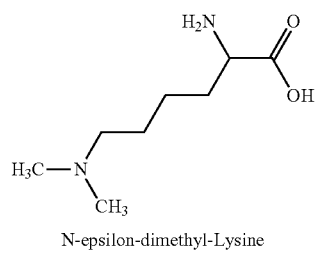
N-epsilon-dimethyl-Lysine
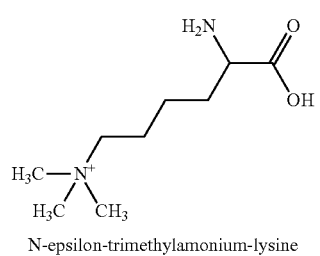
N-epsilon-trimethylamonium-lysine
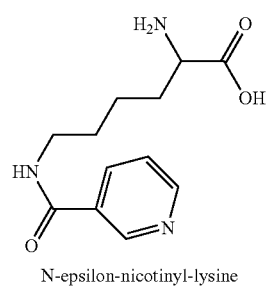 [SMILES: NC(CCCCNC(=O)c1cccnc1)C(=O)O]
N-epsilon-nicotinyl-lysine
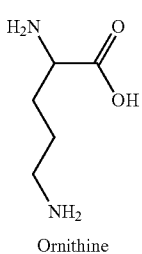
Ornithine
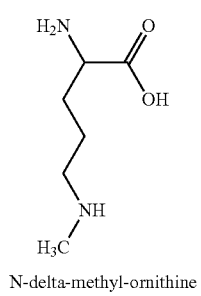
N-delta-methyl-ornithine
TABLE VI-continued
lysine analogues
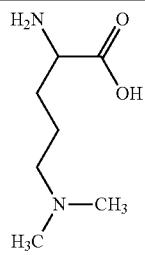
N-delta-N-delta-dimethyl-L-ornithine
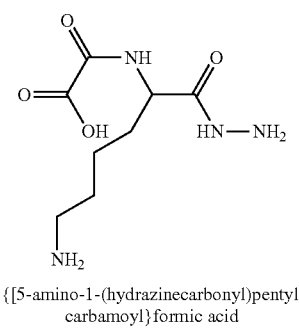 [SMILES: NCCCCC(NC(=O)C(=O)O)C(=O)NN]
{[5-amino-1-(hydrazinecarbonyl)pentyl]carbamoyl}formic acid
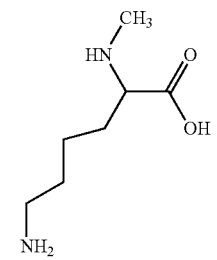
N-alpha-methyl-lysisne
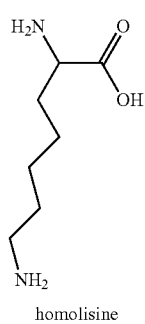 [SMILES: NCCCCCC(N)C(=O)O]
homolisine
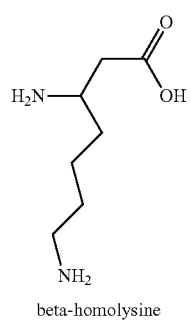 [SMILES: NCCCCC(N)CC(=O)O]
beta-homolysine TABLE VI-continued

| lysine analogues |
|---|
| 2-Amino-6-diazo-5-oxocaproic acid |
| norvaline |
| Alpha-methyl-norvaline |
| Hydroxinorvaline |
| N-delta-i-propyl-ornithine |
| C-alpha-methyl-ornithine |
| beta,beta-dimethyl-ornithine |
| canavanine |
| N-delta-methyl-N-delta-butyl-ornithine |
| delta-(2-methylpyrrolidine)-ornithine |
| N-delta-methyl-N-delta-phenyl-ornithine |
| delta-piperidyl-ornithine |

TABLE VI-continued lysine analogues

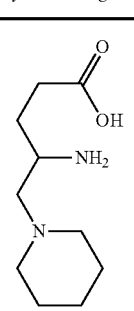

gamma-amino-delta-
piperidyl-valeric acid

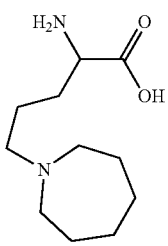

delta-azepanyl-ornithine

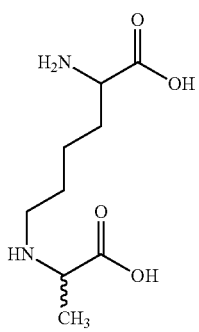

2-amino-6-(1-
carboxyethylamino)hexanoic acid

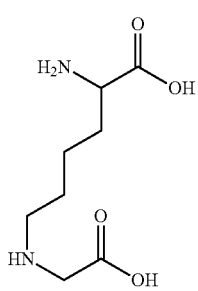

2-amino-6-
(carboxymethylamino)hexanoic acid

TABLE VI-continued lysine analogues

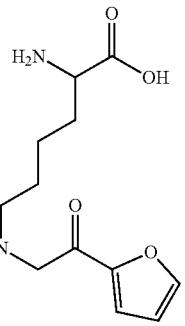

2-amino-6-(2-(furan-2-yl)-
2-oxoethylamino)hexanoic acid

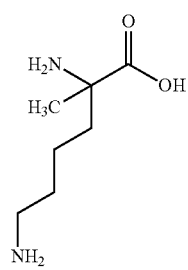

c-alpha-methyl-lysine

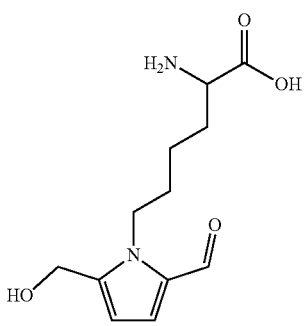

2-amino-6-(formyl-5-hydroxymethyl-
pyrrol-1-yl)-hexanoic acid

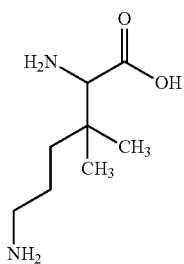

beta,beta-dimethyl-lysine

In certain embodiments, specifically lysine analogues which can be used to develop peptides of the invention by replacing the gatekeeper residue lysine (K) for an analogue of lysine (K) may be N-epsilon-formyl-lysine, N-epsilon-methyl-lysine, N-epsilon-i-propyl-lysine, N-epsilon-dimethyl-lysine, N-epsilon-trimethylamonium-lysine, N-epsilon-nicotinyl-lysine, {[5-amino-1-(hydrazinecarbonyl)pentyl]carbamoyl}formic acid, N-alpha-methyl-lysine, homolysine, beta-homolysine, 2-Amino-6-diazo-5-oxocaproic acid, Hydroxinorvaline, Ornithine, N-delta-methyl-ornithine, N-delta-N-delta-dimethyl-ornithine, N-delta-i-propyl-ornithine, c-alpha-methyl-ornithine, beta,beta-dimethyl-ornithine, canavanine, N-delta-methyl-N-delta-butyl-ornithine, N-delta-methyl-N-delta-phenyl-ornithine, delta-(2-methylpyrrolidine)-ornithine, delta-piperidyl-ornithine, gamma-amino-delta-piperidyl-valeric acid or delta-azepanyl-ornithine.

Specifically proline analogues which can be used to develop variants of the peptides of the invention, such as variants of SEQ ID NO: 1, by replacing of proline in the gatekeepers as depicted in claim 1 for an artificial proline (P) are depicted in Table VII:

TABLE VII proline analogues 3-methylproline 3,4-dehydroproline

2-[(2S)-2-(hydrazinecarbonyl)pyrrolidin-1-yl]-2-oxoacetic acid beta-Homoproline alpha-methyl-proline hydroxyproline 4-oxo-proline beta,beta-dimethyl-proline 5,5-dimethyl-proline TABLE VII-continued proline analogues 4-cyclohexyl-proline 4-phenyl-proline 3-phenyl-proline 4-Mercaptoproline 4-aminoproline In yet another embodiment the linker, $Z_i$, in the peptides of the invention consists of proline, 4-hydroxyproline, (2R, 5S)-5-phenyl-pyrrolidine-2-carboxylic acid, 3,4-dehydro-L-proline, beta-(2-benzothiazolyl)-alanine, 3-(2-furyl)-alanine or beta-(2-thienyl)-alanine.

In yet another embodiment the invention provides a cyclic peptide which is produced by forming a ring structure between an amino-terminal and carboxy-terminal non-natural gatekeeper residue ($A_{2i-1}$ and $A_{2i}$).

In yet another embodiment the peptides of the invention further comprise a detectable label.

The present invention also includes isotopically labelled peptides, which are identical to those defined herein, but for the fact that one or more atoms are replaced by an atom having an atomic mass or mass number different from the atomic mass or mass number usually found in nature. Examples of isotopes that may be incorporated into peptides of the present invention include isotopes of hydrogen, carbon, nitrogen, oxygen, phosphorous, sulphur, fluorine and chlorine, such as $^2H$, $^3H$, $^{13}C$, $^{11}C$, $^{14}C$, $^{15}N$, $^{16}O$, $^{17}O$, $^{31}P$, $^{32}P$, $^{35}S$, $^{18}F$, and $^{36}Cl$, respectively. Peptides of the present invention and pharmaceutically acceptable salts of said peptides or which contain the aforementioned isotopes and/or other isotopes of other atoms are within the scope of this invention. Certain isotopically labeled peptides of the present invention, for example those into which radioactive isotopes such as $^3H$ and $^{14}C$ are incorporated, are useful in drug and/or substrate tissue distribution assays. Tritiated, i.e. $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances, Isotopically labelled peptides of formula I of this invention may generally be prepared by carrying out the procedures disclosed in the Examples below, by substituting a readily available isotopically labelled reagent for a non-isotopically labelled reagent.

In yet another embodiment the peptides of the invention further comprise a molecule which increases the half-life extension.

In yet another embodiment the peptides of the invention further comprise a moiety that increases the solubility of the peptides.

According to other particular embodiments, the molecules may be fused to other moieties, e.g. to extend their half-life in vivo. Apart from increasing stability, such moieties may also increase solubility of the molecule they are fused to. Although the presence of gatekeepers (the numbered X moieties) is in principle sufficient to prevent premature aggregation of the molecules and keep them in solution, the further addition of a moiety that increases solubility (i.e. prevents aggregation) may provide easier handling of the molecules, and particularly improve stability and shelf-life. A well-known example of such moiety is PEG (polyethylene glycol). This moiety is particularly envisaged, as it can be used as linker as well as solubilizing moiety. Other examples include peptides and proteins or protein domains, or even whole proteins (e.g. GFP). In this regard, it should be noted that, like PEG, one moiety can have different functions or effects. For instance, a flag tag (sequence DYKDDDDK (SEQ ID NO: 236)) is a peptide moiety that can be used as a label, but due to its charge density, it will also enhance solubilisation. PEGylation has already often been demonstrated to increase solubility of biopharmaceuticals (e.g. Veronese and Mero, BioDrugs. 2008; 22(5):315-29). Adding a peptide, polypeptide, protein or protein domain tag to a molecule of interest has been extensively described in the art. Examples include, but are not limited to, peptides derived from synuclein (e.g. Park et al., Protein Eng. Des. Sel. 2004; 17:251-260), SET (solubility enhancing tag, Zhang et al., Protein Expr Purif 2004; 36:207-216), thioredoxin (TRX), Glutathione-S-transferase (GST), Maltose-binding protein (MBP), N-Utilization substance (NusA), small ubiquitin-like modifier (SUMO), ubiquitin (Ub), disulfide bond C (DsbC), Seventeen kilodalton protein (Skp), Phage T7 protein kinase fragment (T7PK), Protein G B1 domain, Protein A IgG ZZ repeat domain, and bacterial immunoglobulin binding domains (Hutt et al., J Biol Chem.; 287(7):4462-9, 2012). The nature of the tag will depend on the application, as can be determined by the skilled person. For instance, for transgenic expression of the molecules described herein, it might be envisaged to fuse the molecules to a larger domain to prevent premature degradation by the cellular machinery. Other applications may envisage fusion to a smaller solubilisation tag (e.g. less than 30 amino acids, or less than 20 amino acids, or even less than 10 amino acids) in order not to alter the properties of the molecules too much.

Apart from extending half-life, molecules may be fused to moieties that alter other or additional pharmacokinetic and pharmacodynamic properties. For instance, it is known that fusion with albumin (e.g. human serum albumin), albumin-binding domain or a synthetic albumin-binding peptide improves pharmacokinetics and pharmacodynamics of different therapeutic proteins (Langenheim and Chen, Endocrinol.; 203(3):375-87, 2009). Another moiety that is often used is a fragment crystallizable region (Fc) of an antibody. The nature of these moieties is not vital to the invention and can be determined by the person skilled in the art depending on the application.

In yet another embodiment the peptides of the invention further comprising at least one D-alanine at the amino-terminus and/or the carboxy-terminus of said peptides.

In yet another embodiment the invention provides the peptides of the invention for use as a medicament.

In yet another embodiment the invention provides the peptides of the invention for use as an anti-bacterial agent.

In yet another embodiment the invention provides the peptides of the invention for use to treat gram-positive bacteria.

In yet another embodiment the invention provides the peptides of the invention for use to treat gram-negative bacteria.

In yet another embodiment the invention provides the peptides of the invention for use to treat drug-resistant bacterial strains.

In yet another embodiment the invention provides the peptides of the invention for use to treat multidrug-resistant bacterial strains.

In yet another embodiment the invention provides the peptides of the invention for use to treat multidrug-resistant bacterial strains selected from the list comprising of carbapenem-resistant Enterobacteriaceae, drug-resistant *Neisseria gonorrhoeae*, multidrug resistant Acetinobacter, drug-resistant *Campylobacter*, extended spectrum bata-lactamase producing Enterobacteriaceae, multidrug-resistant *Pseudomonas aeruginosa*, Drug-resistant non-typhoidal *Salmonella*, Drug-resistant *Salmonella typhi* and Drug-resistant *Shigella*.

In yet another embodiment the invention provides the use of the peptides of the invention for use as a diagnostic agent.

In yet another embodiment the invention provides a pharmaceutical composition comprising the peptides of the invention and a pharmaceutically acceptable carrier.

In yet another embodiment the invention provides a method to produce an anti-bacterial peptide comprising the following steps:

i) generating an in silico list of aggregation prone regions (APRs) with a length of 5-14 amino acids, such as 5-12 amino acids, or 6-14 amino acids, such as 6-12 amino acids which APRs are identified in a bacterial proteome, ii) synthetizing a number of 20-200 different peptides comprising an APR based on the following structure: $(A_{2i-1}\text{-APR-}A_2\text{-}Z_i)_n$, wherein n is an integer from 1 to 4 and i increases from 1 to n with each repeat and each $A_{2i-1}$ and $A_2$ are independently selected from 1 to 3 contiguous gatekeeper amino acids selected from R, K, D, E and P, iii) testing said peptides for an anti-bacterial effect and producing an anti-bacterial peptide.

One particularly convenient way of identifying such sequences in a protein, in particular identifying APR sequences in proteins present in a proteome, is by using a beta-aggregation-predicting algorithm. Such algorithms may typically take into account biophysical parameters. Tango and Zyggregator are common examples of such algorithms, but many more have been described in the art, including, but not limited to those described by Bryan et al., *PLoS Comput Biol.* 5(3):e1000333, 2009; Caflish, *Curr Opin Chem BioL.* 10(5):437-44, 2006; Conchillo-Sole et al., *BMC Bioinformatics* 8:65, 2007; Galzitskaya et al., *PLoS Comput Biol.* 29;2(12):e177, 2006; Goldschmidt et al., *PNAS* 107(8):3487-92, 2010; Maurer-Stroh et al., *Nat Meth-* ods 7(3):237-42, 2010; Rojas Quijano et al., *Biochemistry* 45(14):4638-52, 2006; Saiki et al., *Biochem Biophys Res Commun* 343(4):1262-71, 2006; Sanchez de Groot et al., *BMC Struct Biol* 5:18, 2005; Tartaglia et al., *Protein Sci.* 14(10):2723-34, 2005; Tartaglia et al., *J Mol Biol.* 380(2): 425-36, 2008; Thompson et al., *PNAS* 103(11):4074-8, 2006; Trovato et al., *Protein Eng Des Sel.* 20(10):521-3, 2007; Yoon and Welsh, *Protein Sci.* 13(8):2149-60, 2004; Zibaee et al., *Protein Sci.* 16(5):906-18, 2007. Note that many of these are primarily involved with amyloid aggregating sequences and not just with amorphous beta-aggregation. The sequence space of both forms of aggregation can overlap (Rousseau et al., *Current Opinion in Structural Biology* 16:118-126, 2006), and both forms of aggregation are envisaged, as long as the kinetics and conditions of the reaction favour aggregation of the protein(s) of interest.

In some embodiments, the peptides of the invention may comprise one or more additional residues at the amino- and/or carboxyl-terminal ends. In some embodiments, the one or more additional residues are D-alanines. For example, a peptide may comprise one or two D-alanines at the amino- and/or carboxyl-terminal ends.

Likewise, those skilled in the art will appreciate that the present invention also encompasses fusion polypeptides comprising a specialized non-naturally occurring peptides. As an alternative, the fusion protein can comprise a reporter molecule. In other embodiments, the fusion protein can comprise a polypeptide that provides a function or activity that is the same as or different from the activity of the peptide, e.g. a targeting, binding, or enzymatic activity or function.

Likewise, it will be understood that the peptides specifically disclosed herein will typically tolerate substitutions in the amino acid sequence and substantially retain biological activity. To identify peptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like.

As is known in the art, a number of different programs can be used to identify whether a polypeptide has sequence identity or similarity to a known sequence. Sequence identity or similarity may be determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387 (1984), preferably using the default settings, or by inspection. An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351 (1987); the method is similar to that described by Higgins & Sharp, CABIOS 5:151 (1989). Another example of a useful algorithm is the BLAST algorithm, described in Altschul et al., J. Mol. Biol. 215:403 (1990) and Karlin et al., Proc. Natl. Acad. Sci. USA 90:5873 (1993). A particularly useful BLAST program is the WU-BLAST-2 program which was obtained from Altschul et al., Meth. Enzymol., 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity. An additional useful algorithm is gapped BLAST as reported by Altschul et al., Nucleic Acids Res. 25:3389 (1997). A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). The alignment may include the introduction of gaps in the sequences to be aligned. In addition, for sequences which contain either more or fewer amino acids than the peptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In a specific embodiment peptides of the invention can be modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by any suitable methods. For example, one or more non-naturally occurring amino acids, such as for example D-alanine, can be added to the termini. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Additionally, the peptide terminus can be modified, e.g. by acetylation of the N-terminus and/or amidation of the C-terminus. Likewise, the peptides can be covalently or noncovalently coupled to pharmaceutically acceptable "carrier" proteins prior to administration.

Administration of Peptides of the
Invention—Pharmaceutical Compositions
Comprising Peptides of the Invention In one embodiment, the peptides of the invention are administered directly to a subject. Generally, the compounds of the invention will be suspended in a pharmaceutically-acceptable carrier (e.g., physiological saline) and administered orally or by intravenous infusion, or administered subcutaneously, intramuscularly, intrathecally, intraperitoneally, intrarectally, intravaginally, intranasally, intragastrically, intratracheally, or intrapulmonarily. In another embodiment, the intratracheal or intrapulmonary delivery can be accomplished using a standard nebulizer, jet nebulizer, wire mesh nebulizer, dry powder inhaler, or metered dose inhaler. They can be delivered directly to the site of the bacterial infection, such as for example lungs, kidney, bladder, or intestines. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Wide variations in the needed dosage are to be expected in view of the variety of peptides and variants possible and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-; 20-, 50-, 100-, 150- or more fold).

In certain embodiments, the peptides of the invention comprise at least one modified terminus, e.g., to protect the peptide against degradation. In some embodiments, the N-terminus is acetylated and/or the C-terminus is amidated. In certain embodiments, the peptides of the invention comprise at least one non-natural amino acid (e.g., 1, 2, 3, or more) or at least one terminal modification (e.g. 1 or 2). In some embodiments, the peptide comprises at least one non-natural amino acid and at least one terminal modification.

The peptides of the present invention can optionally be delivered in conjunction with other therapeutic agents. The additional therapeutic agents can be delivered concurrently with the peptides of the invention. As used herein, the word "concurrently" means sufficiently close in time to produce a combined effect (that is, concurrently can be simultaneously, or it can be two or more events occurring within a short time period before or after each other). In one embodiment of the invention, the non-naturally occurring peptide is delivered to a patient concurrently with an antibiotic that modulates the growth of bacteria where the combined activity of the non-naturally occurring peptide and the antibiotic agent have superior activity to the bacteria alone. Another aspect of the invention relates to a kit comprising a peptide from the invention and useful for carrying out the methods of the invention. The kit may further comprise additional reagents for carrying out the methods (e.g., buffers, containers, additional therapeutic agents) as well as instructions. As a further aspect, the invention provides pharmaceutical formulations and methods of administering the same to achieve any of the therapeutic effects (e.g. bacterial killing) discussed above. The pharmaceutical formulation may comprise any of the reagents discussed above in a pharmaceutically acceptable carrier, e.g. a non-naturally occurring peptide or variant thereof. By "pharmaceutically acceptable" it is meant a material that is not biologically or otherwise undesirable, i.e., the material can be administered to a subject without causing any undesirable biological effects such as toxicity. The formulations of the invention can optionally comprise medicinal agents, pharmaceutical agents, carriers, adjuvants, dispersing agents, diluents, and the like. The peptides of the invention can be formulated for administration in a pharmaceutical carrier in accordance with known techniques. See, e.g. Remington, The Science And Practice of Pharmacy (Ed. 2014). In the manufacture of a pharmaceutical formulation according to the invention, the peptide (including the physiologically acceptable salts thereof) is typically admixed with, inter alia, an acceptable carrier. The carrier can be a solid or a liquid, or both, and is preferably formulated with the peptide as a unit-dose formulation, for example, a tablet, which can contain from 0.01 or 0.5% to 95% or 99% by weight of the peptide. One or more peptides can be incorporated in the formulations of the invention, which can be prepared by any of the well-known techniques of pharmacy. A further aspect of the invention is a method of treating subjects in vivo, comprising administering to a subject a pharmaceutical composition comprising a peptide of the invention in a pharmaceutically acceptable carrier, wherein the pharmaceutical composition is administered in a therapeutically effective amount. Administration of the peptides of the present invention to a human subject or an animal in need thereof can be by any means known in the art for administering compounds. The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, into the pancreas, or into a tumor or the tissue surrounding a tumor). The most suitable route in any given case will depend on the nature and severity of the condition being treated and on the nature of the particular peptide which is being used.

For injection, the carrier will typically be a liquid, such as sterile pyrogen-free water, sterile normal saline, hypertonic saline, pyrogen-free phosphate-buffered saline solution. For other methods of administration, the carrier can be either solid or liquid. For oral administration, the peptide can be administered in solid dosage forms, such as capsules, tablets, and powders, or in liquid dosage forms, such as elixirs, syrups, and suspensions. Peptides can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance. Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia. Formulations of the present invention suitable for parenteral administration comprise sterile aqueous and non-aqueous injection solutions of the peptide, which preparations are preferably isotonic with the blood of the intended recipient. These preparations can contain antioxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a peptide of the invention, in a unit dosage form in a sealed container. The peptide or salt is provided in the form of a lyophilizate which is capable of being reconstituted with a suitable pharmaceutically acceptable carrier to form a liquid composition suitable for injection thereof into a subject. The unit dosage form typically comprises from about 1 mg to about 10 grams of the peptide or salt. When the peptide or salt is substantially water-insoluble, a sufficient amount of emulsifying agent which is pharmaceutically acceptable can be employed in sufficient quantity to emulsify the peptide or salt in an aqueous carrier. One such useful emulsifying agent is phosphatidyl choline. Formulations suitable for rectal administration are preferably presented as unit dose suppositories. These can be prepared by admixing the peptide with one or more conventional solid carriers, for example, cocoa butter, and then shaping the resulting mixture. Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof. Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, Pharm. Res. 3:318 (1986) and typically take the form of an optionally buffered aqueous solution of the peptides. Suitable formulations comprise citrate or bis/tris buffer (pH 6) or ethanol/water and contain from 0.1 to 0.2M of the compound. The peptide can alternatively be formulated for nasal administration or otherwise administered to the lungs of a subject by any suitable means, e.g., administered by an aerosol suspension of respirable particles comprising the peptide, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. Aerosols of liquid particles comprising the peptide can be produced by any suitable means, such as with a pressure-driven aerosol nebulizer or an ultrasonic nebulizer, as is known to those of skill in the art. Aerosols of solid particles comprising the peptide can likewise be produced with any solid particulate medicament aerosol generator, by techniques known in the pharmaceutical art. Alternatively, one can administer the peptide in a local rather than systemic manner, for example, in a depot or sustained-release formulation.

Further, the present invention provides liposomal formulations of the peptides disclosed herein and salts thereof. The technology for forming liposomal suspensions is well known in the art. When the peptide or salt thereof is an aqueous-soluble salt, using conventional liposome technology, the same can be incorporated into lipid vesicles. In such an instance, due to the water solubility of the peptide or salt, the peptide or salt will be substantially entrained within the hydrophilic center or core of the liposomes. The lipid layer employed can be of any conventional composition and can either contain cholesterol or can be cholesterol-free. When the peptide or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques. The liposomal formulations containing the peptides disclosed herein or salts thereof, can be lyophilized to produce a lyophilizate which can be reconstituted with a pharmaceutically acceptable carrier, such as water, to regenerate a liposomal suspension. In the case of water-insoluble peptides, a pharmaceutical composition can be prepared containing the water-insoluble peptide, such as for example, in an aqueous base emulsion. In such an instance, the composition will contain a sufficient amount of pharmaceutically acceptable emulsifying agent to emulsify the desired amount of the peptide. Particularly useful emulsifying agents include phosphatidyl cholines and lecithin. In particular embodiments, the peptide is administered to the subject in a therapeutically effective amount, as that term is defined above. Dosages of pharmaceutically active peptides can be determined by methods known in the art, see, e.g., Remington's Pharmaceutical Sciences. The therapeutically effective dosage of any specific peptide will vary somewhat from peptide to peptide, and patient to patient, and will depend upon the condition of the patient and the route of delivery. As a general proposition, a dosage from about 0.1 to about 50 mg/kg will have therapeutic efficacy, with all weights being calculated based upon the weight of the peptide, including the cases where a salt is employed. Toxicity concerns at the higher level can restrict intravenous dosages to a lower level such as up to about 10 mg/kg, with all weights being calculated based upon the weight of the peptide, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 µmol/kg to 50 µmol/kg, and more particularly to about 22 µmol/kg and to 33 µmol/kg of the peptide for intravenous or oral administration, respectively. In particular embodiments of the invention, more than one administration (e.g. two, three, four, or more administrations) can be employed over a variety of time intervals (e.g., hourly, daily, weekly, monthly, etc.) to achieve therapeutic effects. The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults.

Synthesis of Peptides

In specific embodiments the peptides of the invention can be produced according to several peptide synthesis methods known in the art. The peptide synthesis method may be any of, for example, a solid phase synthesis process and a liquid phase synthesis process. That is, the object peptide can be produced by repeating condensation of a partial peptide or amino acid capable of constituting compound (1) and the remaining portion (which may be constituted by two or more amino acids) according to a desired sequence. When a product having the desirable sequence has a protecting group, the object peptide can be produced by eliminating a protecting group. Examples of the condensing method and eliminating method of a protecting group to be known include methods described in the following (1)-(5). (1) M. Bodanszky and M. A. Ondetti: Peptide Synthesis, Interscience Publishers, New York (1966), (2) Schroeder and Luebke: The Peptide, Academic Press, New York (1965), (3) Nobuo Izumiya, et al.: Peptide Gosei-no-Kiso to Jikken (Basics and experiments of peptide synthesis), published by Maruzen Co. (1975), (4) Haruaki Yajima and Shunpei Sakakibara: Seikagaku Jikken Koza (Biochemical Ex-periment) 1, Tanpakushitsu no Kagaku (Chemistry of Proteins) IV, 205 (1977) and (5) Haruaki Yajima, ed.: Zoku lyakuhin no Kaihatsu (A sequel to Development of Pharmaceuticals), Vol. 14, Peptide Synthesis, published by Hirokawa Shoten. After the reaction, the peptides can be purified and isolated using conventional methods of purification, such as solvent extraction, distillation, column chromatography, liquid chromatography, recrystallization, etc., in combination thereof. When the peptide obtained by the above-mentioned method is in a free form, it can be converted to a suitable salt by a known method; conversely, when the peptide is obtained in the form of a salt, the salt can be converted to a free form or other salt by a known method. The starting compound may also be a salt. Examples of such salt include those exemplified as salts of the peptides mentioned bellow. For condensation of protected amino acid or peptide, various activation reagents usable for peptide synthesis can be used, which are particularly preferably trisphosphonium salts, tetramethyluronium salts, carbodiimides and the like. Examples of the trisphosphonium salt include benzotriazol-1-yloxytris(pyrrolizino)phosphoniumhexafluorophosphate (PyBOP), bromotris(pyrrolizino)phosphoniumhexafluorophosphate (PyBroP), 7-azabenzotriazol-1-yloxytris(pyrrolizino)phosphoniumhexafluorophosphate (PyAOP), examples of the tetramethyluronium salt include 2-(1H-benzotriazol-1-yl)-1,1,3,3-hexafluorophosphate (HBTU), 2-(7-azabenzotriazol-1-yl)-1,1,3,3-hexafluorophosphate (HATU), 2-(1H-benzotriazol-1-yl)-1,1,3,3-tetramethyluroniumtetrafluoroborate (TBTU), 2-(5-norbornane-2,3-dicarboxyimide)-1,1,3,3-tetramethyluroniumtet-rafluoroborate (TNTU), O—(N-succimidyl)-1,1,3,3-tetramethyluroniumtetrafluoroborate (TSTU), and examples of the carbodiimide include DCC, N,N'-diisopropylcarbodiimide (DIPCDI), N-ethyl-N'-(3-dimethylaminopropyl)carbodiimide hydrochloride (EDCl·HCl) and the like. For condensation using these, addition of a racemization inhibitor (e.g., HONB, HOBt, HOAt, HOOBt etc.) can be used. A solvent to be used for the condensation can be appropriately selected from those known to be usable for peptide condensation reaction. For example, acid amides such as anhydrous or water-containing N,N-dimethylformamide, N,N-dimethylacetamide, N-methylpyrrolidone and the like, halogenated hydrocarbons such as methylene chloride, chloroform and the like, alcohols such as trifluoroethanol, phenol and the like, sulfoxides such as dimethyl-sulfoxide and the like, tertiary amines such as pyridine and the like, ethers such as dioxane, tetrahydrofuran and the like, nitriles such as acetonitrile, propionitrile and the like, esters such as methyl acetate, ethyl acetate and the like, an appropriate mixture of these and the like can be used. Reaction temperature is appropriately selected from the range known to be usable for peptide binding reactions, and is normally selected from the range of about −20 C ("C" represents "degrees Celsius") to 50 degrees C. An activated amino acid derivative is normally used from 1.5 to 6 times in excess. In phase synthesis, when a test using the ninhydrin reaction reveals that the condensation is insufficient, sufficient condensation can be conducted by repeating the condensation reaction without elimination of protecting groups. If the condensation is yet insufficient even after repeating the reaction, unreacted amino acids can be acylated with acetic anhydride, acetylimidazole or the like so that an influence on the subsequent reactions can be avoided. Examples of the protecting groups for the amino groups of the starting amino acid include Z, Boc, tert-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, trityl and the like. Examples of the carboxyl-protecting group for the starting amino acid include allyl, 2-adamantyl, 4-nitrobenzyl, 4-methoxybenzyl, 4-chlorobenzyl, phenacyl and benzyloxycarbonylhydrazide, tert-butoxycarbonylhydrazide, tritylhydrazide and the like, in addition to the above-mentioned $C_{1-6}$ alkyl group, $C_{3-10}$ cycloalkyl group, $C_{7-14}$ aralkyl group. The hydroxyl group of serine or threonine can be protected, for example, by esterification or etherification. Examples of the group suitable for the esterification include lower ($C_{2-4}$) alkanoyl groups such as an acetyl group and the like, aroyl groups such as a benzoyl group and the like, and the like, and a group derived from an organic acid and the like. In addition, examples of the group suitable for etherification include benzyl, tetrahydropyranyl, tert-butyl (Bu.sup.t), trityl (Trt) and the like. Examples of the protecting group for the phenolic hydroxyl group of tyrosine include Bzl, 2,6-dichlorobenzyl, 2-nitrobenzyl, Br—Z, tert-butyl and the like. Examples of the protecting group for the imidazole of histidine include Tos, 4-methoxy-2,3,6-trimethylbenzenesulfonyl (Mtr), DNP, Bom, Bum, Boc, Trt, Fmoc and the like.

Examples of the protecting group for the guanidino group of arginine include Tos, Z, 4-methoxy-2,3,6-trimethylbenzenesulfonyl (Mtr), p-methoxybenzenesulfonyl (MBS), 2,2,5,7,8-pentamethylchromane-6-sulfonyl (Pmc), mesitylene-2-sulfonyl (Mts), 2,2,4,6,7-pentamethyldihydrobenzofuran-5-sulfonyl (Pbf), Boc, Z, $NO_2$ and the like. Examples of the protecting group for a side chain amino group of lysine include Z, Cl—Z, trifluoroacetyl, Boc, Fmoc, Trt, Mtr, 4,4-dimethyl-2,6-dioxocyclohexylideneyl (Dde) and the like. Examples of the protecting group for indolyl of tryptophan include formyl (For), Z, Boc, Mts, Mtr and the like. Examples of the protecting group for asparagine and glutamine include Trt, xanthyl (Xan), 4,4'-dimethoxybenzhydryl (Mbh), 2,4,6-trimethoxybenzyl (Tmob) and the like. Examples of activated carboxyl groups in the starting material include corresponding acid anhydride, azide, active esters [ester with alcohol (e.g., pentachlorophenol, 2,4,5-trichlorophenol, 2,4-dinitrophenol, cyanomethylalcohol, paranitrophenol, HONB, N-hydroxysuccimide, 1-hydroxybenzotriazole (HOBt), 1-hydroxy-7-azabenzotriazole (HOAt))] and the like. Examples of the activated amino group in the starting material include corresponding phosphorous amide. Examples of the method for removing (eliminating) a protecting group include a catalytic reduction in a hydrogen stream in the presence of a catalyst such as Pd-black or Pd-carbon; an acid treatment using anhydrous hydrogen fluoride, methanesulfonic acid, trifluoromethanesulfonic acid, trifluoroacetate, trimethylsilyl bromide (TMSBr), trimethylsilyl trifluoromethanesulfonate, tetrafluoroboric acid, tris(trifluoro)boric acid, boron tribromide, or a mixture solution thereof; a base treatment using diisopropy-lethylamine, triethylamine, piperidine, piperazine or the like; and reduction with sodium in liquid ammonia, and the like. The elimination reaction by the above-described acid treatment is generally carried out at a temperature of −20 C to 40 C; the acid treatment is efficiently conducted by adding a cation scavenger such as anisole, phenol, thioanisole, metacresol and paracresol; dimethylsulfide, 1,4-butanedithiol, 1,2-ethanedithiol and the like. Also, a 2,4-dinitrophenyl group used as a protecting group of the imidazole of histidine is removed by thiophenol treatment; a formyl group used as a protecting group of the indole of tryptophan is removed by deprotection by acid treatment in the presence of 1,2-ethanedithiol, 1,4-butanedithiol, or the like, as well as by alkali treatment with dilute sodium hydroxide, dilute ammonia, or the like.

In addition, the peptides of the invention may be a solvate (e.g., hydrate) or a non-solvate (e.g., non-hydrate).The peptides may be labeled with an isotope (e.g. $^3$H, $^{14}$C, $^{11}$S, $^{125}$I) or the like. Furthermore, the peptides may be a deuterium conversion form wherein $^1$H is converted to $^2$H(D). Peptides labeled or substituted with an isotope can be used as, for example, a tracer (PET tracer) for use in Positron Emission Tomography (PET), and is useful in the fields of medical diagnosis and the like.

For the peptides mentioned herein, the left end is the N-terminal (amino terminal) and the right end is the C-terminal (carboxyl terminal) in accordance with the conventional peptide marking. The C-terminal of peptide may be any of an amide (—CONH$_2$), a carboxyl group (—COOH), a carboxylate (—COO—), an alkylamide (—CONHR), and an ester (—COOR). Particularly, amide (—CONH$_2$) is preferable. The compounds may be in a salt form. Examples of such salt include metal salts, ammonium salts, salts with organic base, salts with inorganic acid, salts with organic acid, salts with basic or acidic amino acid, and the like.

In certain embodiments, the peptides may also be in a prodrug form. A prodrug means a compound which is converted to a functional peptide of the invention with a reaction due to an enzyme, gastric acid, etc. under the physiological condition in the living body, that is, a compound which is converted to a peptide of the invention with oxidation, reduction, hydrolysis, etc. according to an enzyme; a compound which is converted to a peptide of the invention by hydrolysis etc. due to gastric acid, etc. Examples of a prodrug of a peptide of the invention include a compound wherein an amino of the peptide is acylated, alkylated or phosphorylated (e.g., compound wherein amino of the peptide is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated, and the like); a compound wherein a hydroxy of the peptide is acylated, alkylated, phosphorylated or borated (e.g., a compound wherein a hydroxy of the peptide is acetylated, palmytoylated, propanoylated, pivaloylated, succinylated, fumarylated, alanylated or dimethylaminomethylcarbonylated); a compound wherein a carboxy of the peptide is esterified or amidated (e.g., a compound wherein a carboxy of the peptide is $C_{1-6}$ alkyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl) methyl esterified, cyclohexyloxycar-bonylethyl esterified or methylamidated) and the like. Among others, a compound wherein carboxy of compound (1) is esterified with $C_{1-6}$ alkyl such as methyl, ethyl, tert-butyl or the like is preferably used. These compounds can be produced from a peptide by a method known per se. A prodrug of a peptide of the invention may also be one which is converted into a peptide of the invention under a physiological condition, such as those described in IYAKUHIN no KAIHATSU (Development of Pharmaceuticals), Vol. 7, Design of Molecules, p. 163-198, Published by HIROKAWA SHOTEN (1990). In the present specification, the prodrug may form a salt. Examples of such a salt include those exemplified as the salt of a peptide of the invention. A peptide of the invention may form a crystal. Crystals having a singular crystal form or a mixture of plural crystal forms are also included in a peptide of the invention. Crystals can be produced by crystallizing a peptide of the invention according to a crystallization method known per se. In addition, a peptide of the invention may be a pharmaceutically acceptable co-crystal or co-crystal salt. Here, the co-crystal or co-crystal salt means a crystalline substance consisting of two or more particular substances which are solids at room temperature, each having different physical properties (e.g. structure, melting point, heat of melting, hygroscopicity, solubility, stability etc.). The cocrystal and cocrystal salt can be produced by cocrystallization known per se. The crystal of a peptide of the invention is superior in physicochemical properties (e.g., melting point, solubility, stability) and biological properties (e.g. pharmacokinetics (absorption, distribution, metabolism, excretion), efficacy expression), and thus it is extremely useful as a medicament.

In further aspects and embodiments, the invention also provides subject-matter as set forth in any one and all of (1) to (14) below:

(1) A peptide comprising the following structure: $(A_{2i-1}\text{-}X_1\text{-}X_2\text{-}X_3\text{-}X_4\text{-}X_5\text{-}X_6\text{-}X_7\text{-}A_2\text{-}Z_i)_n$, wherein:

n is an integer from 1 to 4 and i increases from 1 to n with each repeat;

each $A_2$-, and $A_{2i}$ are independently selected from 1 to 3 contiguous gatekeeper amino acids selected from R, K, D, E and P and/or 1 to 3 non-natural gatekeeper amino acid selected from 3-methylproline, 3,4-dehydro-proline, 2-[(2S)-2-(hydrazinecarbonyl)pyrrolidin-1-yl]-2-oxoacetic acid, beta-homoproline, alpha-methyl-proline, hydroxyproline, 4-oxo-proline, beta,beta-dimethyl-proline, 5,5-dimethyl-proline, 4-cyclohexyl-proline, 4-phenyl-proline, 3-phenyl-proline, 4-aminoproline, 4-mercaptoproline, 2-amino-adipic acid (homoglutamic acid), 2-aminoheptanedioic acid (2-aminopimelic acid), 2-aminooctanedioic acid (aminosuberic acid), 2-amino-4-carboxy-pentanedioic acid (4-carboxyglutamic acid), glyoxal-hydroimidazolone, methylglyoxal-hydroimidazolone, N-alpha-methyl-arginine, omega-methyl-arginine, norarginine, homoarginine, N,N'-diethyl-homoarginine, beta-homoarginine, 2-amino-3-ureido-propionic acid, 2-amino-6-(1-carboxyethylamino)hexanoic acid, 2-amino-6-carboxymethylamino)hexanoic acid, 2-amino-6-(2-(furan-2-yl)-2-oxoethylamino)hexanoic acid, 2-amino-6-(formyl-5-hydroxymethyl-pyrrol-1-yl)-hexanoic acid, c-alpha-methyl-lysine, beta,beta-dimethyl-lysine, N-epsilon-formyl-lysine, N-epsilon-methyl-lysine, N-epsilon-i-propyl-lysine, N-epsilon-dimethyl-lysine, N-epsilon-trimethylamonium-lysine, N-epsilon-nicotinyl-lysine, {[5-amino-1-(hydrazinecarbonyl)pentyl]carbamoyl}formic acid, N-alpha-methyl-lysine, homolysine, beta-homolysine, 2-Amino-6-diazo-5-oxocaproic acid, norvaline, alpha-methyl-norvaline, Hydroxinorvaline, Ornithine, N-delta-methyl-ornithine, N-delta-N-delta-dimethyl-ornithine, N-delta-i-propyl-ornithine, c-alpha-methyl-ornithine, beta,beta-dimethyl-ornithine, canavanine, N-delta-methyl-N-delta-butyl-ornithine, N-delta-methyl-N-delta-phenyl-ornithine, delta-(2-methylpyrrolidine)-ornithine, delta-piperidyl-ornithine, gamma-amino-delta-piperidyl-valeric acid and delta-azepanyl-ornithine and wherein the amino-terminal gatekeeper amino acid or amino-terminal non-natural gatekeeper amino acid in the peptide structure is optionally acetylated and/or wherein the carboxy-terminal gatekeeper amino acid or carboxy-terminal non-natural gatekeeper amino acid in the peptide sequence is optionally amidated, $X_1$ is glycine or a conservative amino acid substitution of glycine or a non-natural amino acid variant of glycine or a D-amino acid of a conservative amino acid substitution of glycine or a D-amino acid of a non-natural amino acid variant of glycine, $X_2$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_3$ is glycine or a conservative amino acid substitution of glycine or a non-natural amino acid variant of glycine or a or a D-amino acid of a conservative amino acid substitution of glycine or a D-amino acid of a non-natural amino acid variant of glycine, $X_4$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_5$ is alanine or a conservative amino acid substitution of alanine or a non-natural amino acid variant of alanine or a D-amino acid of alanine or a D-amino acid of a conservative amino acid substitution of alanine or a D-amino acid of a non-natural amino acid variant of alanine, $X_6$ is leucine or a conservative amino acid substitution of leucine or a non-natural amino acid variant of leucine or a D-amino acid of leucine or a D-amino acid of a conservative amino acid substitution of leucine or a D-amino acid of a non-natural amino acid variant of leucine, $X_7$ is valine or a conservative amino acid substitution of valine or a non-natural amino acid variant of valine or a D-amino acid of valine or a D-amino acid of a conservative amino acid substitution of valine or a D-amino acid of a non-natural amino acid variant of valine, and wherein $X_1$—$X_2$-$X_3$-$X_4$-$X_5$-$X_6$-$X_7$ and $X_7$—$X_6$-$X_5$-$X_4$-$X_3$-$X_2$-$X_1$ are used interchangeably in the repeats wherein n is 2 to 4, and each $Z_i$ is a linker and wherein each $Z_i$ is independently selected from stretch of between 1 and 5 units, wherein a unit is PEG, an amino acid or a non-natural amino acid.

(2) A peptide according to (1) wherein:

$X_1$ and $X_3$ are selected from glycine, N-alpha-methyl-glycine (sarcosine), cyclopropylglycine and cyclopentylglycine $X_2$, $X_4$ and $X_6$ are selected from leucine, valine, 2-amino-3,3-dimethyl-butyric acid (t-Leucine), alpha-methylleucine, hydroxyleucine, 2,3-dehydro-leucine, N-alpha-methyl-leucine, 2-Amino-5-methyl-hexanoic acid (homoleucine), 3-Amino-5-methylhexanoic acid (beta-homoleucine), 2-Amino-4,4-dimethyl-pentanoic acid (4-methyl-leucine, neopentylglycine), 4,5-dehydro-norleucine (allylglycine), L-norleucine, N-alpha-methyl-norleucine and 6-hydroxy-norieucine $X_5$ is selected from alanine, 2-amino-isobutyric acid (2-Methylalanine), 2-Amino-2-methylbutanoic acid (Isovaline), N-alpha-Methyl-alanine, 2-Amino-2-methylpent-4-enoic acid (alpha-allylalanine), beta-homoalanine, 2-indanyl-glycine, Di-n-propyl-glycine, Di-n-butyl-glycine, Diethyl-glycine, (1-naphthyl)alanine, (2-naphthyl)alanine, cyclohexylglycine, adamantyl-glycine, beta-homoallylglycine $X_7$ is selected from valine, leucine, c-alpha-methyl-valine (2,3-dimethylbutanoic acid), 2,3-dehydro-valine, 3,4-dehydro-valine, 3-methyl-L-isovaline (methylvaline), 2-amino-3-hydroxy-3-methylbutanoic acid (hydroxyvaline), beta-homovaline and N-alpha-methyl-valine.

(3) A peptide according to (1) or (2) wherein $Z_i$ consists of proline, 4-hydroxyproline, (2R,5S)-5-penyl-pyrrolidine-2-carboxylic acid, 3,4-dehydro-L-proline, beta-(2-benzothiazolyl)-alanine, 3-(2-furyl)-alanine or beta-(2-thienyl)-alanine.

(4) A cyclic peptide according to any one of (1) to (3) wherein the aminoterminal and carboxyterminal gatekeeper aminoacids $A_{2i-1}$ and $A_2$ form a ring structure.

(5) A peptidomimetic generated from a peptide according to (1), (2), (3) or (4). (6) The peptide or peptidomimetic of any one of (1) to (5), further comprising a detectable label. (7) The peptide or peptidomimetic of any one of (1) to (5), further comprising a molecule which increases the half-life extension.

(8) The peptide or peptidomimetic of any one of (1) to (5), further comprising a moiety that increases solubility of the molecule.

(9) The peptide or peptidomimetic of any one of (1) to (5), further comprising at least one D-alanine at the amino-terminus and/or the carboxy-terminus.

(10) A molecule according to any one of (1) to (9) for use as a medicine.

(11) A molecule according to any one of (1) to (9) for use as an anti-bacterial agent.

(12) A molecule according to any one of (1) to (9) for use as a diagnostic agent.

(13) A pharmaceutical composition, comprising according to any one of (1) to (9) and a pharmaceutically acceptable carrier.

(14) In yet another embodiment the invention provides a method to produce an anti-bacterial peptide comprising the following steps:

(i) generating an in silico list of aggregation prone regions (APRs) with a length of 6-12 amino acids which APRs are identified in a bacterial proteome, (ii) synthetizing a number of 20-200 different peptides comprising an APR based on the following structure: $(A_{2i-1}\text{-APR-}A_{2i}\text{-}Z_i)_n$, wherein n is an integer from 1 to 4 and i increases from 1 to n with each repeat and each $A_{2i-1}$ and $A_{2i}$ are independently selected from 1 to 3 contiguous gatekeeper amino acids selected from R, K, D, E and P, (iii) testing said peptides for an anti-bacterial effect and producing an anti-bacterial peptide.

In further aspects and embodiments, the invention also provides subject-matter as set forth in any one and all of (1*) to (12*) below:

(1*) A peptide comprising the following structure: $(A_{2i-1}\text{-APR-}A_{2i}\text{-}Z_i)_n$, wherein:

n is an integer from 1 to 4 and i increases from 1 to n with each repeat;

each $A_{2i-1}$ and $A_{2i}$ are independently selected from 1 to 3 contiguous gatekeeper amino acids selected from R, K, D, E and P or 1 to 3 non-natural gatekeeper amino acid selected from 3-methylproline, 3,4-dehydro-proline, 2-[(2S)-2-(hydrazinecarbonyl)pyrrolidin-1-yl]-2-oxoacetic acid, beta-homoproline, alpha-methyl-proline, hydroxyproline, 4-oxo-proline, beta,beta-dimethyl-proline, 5,5-dimethyl-proline, 4-cyclohexyl-proline, 4-phenyl-proline, 3-phenyl-proline, 4-aminoproline, 4-mercaptoproline, 2-amino-adipic acid (homoglutamic acid), 2-amino-heptanedioic acid (2-aminopimelic acid), 2-amino-octanedioic acid (aminosuberic acid), 2-amino-4-carboxy-pentanedioic acid (4-carboxyglutamic acid), glyoxal-hydroimidazolone, methylglyoxal-hydroimidazolone, N-alpha-methyl-arginine, omega-methyl-arginine, norarginine, homoarginine, N,N'-diethyl-homoarginine, beta-homoarginine, 2-amino-3-ureido-propionic acid, 2-amino-6-(1-carboxyethylamino)hexanoic acid, 2-amino-6-carboxymethylamino)hexanoic acid, 2-amino-6-(2-(furan-2-yl)-2-oxoethylamino)hexanoic acid, 2-amino-6-(formyl-5-hydroxymethyl-pyrrol-1-yl)-hexanoic acid, c-alpha-methyl-lysine, beta,beta-dimethyl-lysine, N-epsilon-formyl-lysine, N-epsilon-methyl-lysine, N-epsilon-i-propyl-lysine, N-epsilon-dimethyl-lysine, N-epsilon-trimethylamonium-lysine, N-epsilon-nicotinyl-lysine, {[5-amino-1-(hydrazinecarbonyl)pentyl]carbamoyl}formic acid, N-alpha-methyl-lysine, homolysine, beta-homolysine, 2-Amino-6-diazo-5-oxocaproic acid, norvaline, alpha-methyl-norvaline, Hydroxinorvaline, Ornithine, N-delta-methyl-ornithine, N-delta-N-delta-dimethyl-ornithine, N-delta-i-propyl-ornithine, c-alpha-methyl-ornithine, beta,beta-dimethyl-ornithine, canavanine, N-delta-methyl-N-delta-butyl-ornithine, N-delta-methyl-N-delta-phenyl-ornithine, delta-(2-methylpyrrolidine)-ornithine, delta-piperidyl-ornithine, gamma-amino-delta-piperidyl-valeric acid and delta-azepanyl-ornithine and wherein the amino-terminal gatekeeper amino acid or amino-terminal non-natural gatekeeper amino acid in the peptide structure is optionally acetylated and/or wherein the carboxy-terminal gatekeeper amino acid or carboxy-terminal non-natural gatekeeper amino acid in the peptide sequence is optionally amidated, the names of the peptides comprised in APR are depicted in Table 5 (P3, P4, P5, P12, P14, P16, P18, P23, P26, P29, P33, P39, P40, P49, P50, P58, P72, P76, P79, P80, P87, P88, P89, P90, P91, P92, P93, P99, P101, P103, P105, P111, P112, P113, P114, P115, P116, P117, P118, P123, P124 and P125) and the corresponding amino acid sequences for these peptides are depicted in Table 4 wherein APR comprises natural amino acids or APR comprises conservative amino acid substitutions of the amino acids present in APR or APR comprises non-natural amino acid analogues of the amino acids present in the peptide sequences present in APR or APR comprises D-amino acid substitutions in the peptide sequences of the amino acids present in APR, and wherein the amino acids in APR can be in a direct or inverted repeat wherein n is 2 to 4, and each $Z_i$ is a linker and wherein each $Z_i$ is independently selected from stretch of between 1 and 5 units, wherein a unit is PEG, an amino acid or a non-natural amino acid.

(2*) A peptide according to (1*) wherein Z; consists of proline, 4-hydroxyproline, (2R,5S)-5-phenyl-pyrrolidine-2-carboxylic acid, 3,4-dehydro-L-proline, beta-(2-benzothiazolyl)-alanine, 3-(2-furyl)-alanine or beta-(2-thienyl)-alanine.

(3*) A cyclic peptide according to any one of (1*) to (2*) wherein the aminoterminal and carboxyterminal gatekeeper aminoacids $A_{2i-1}$, and $A_2$ form a ring structure.

(4*) The peptide of any one of (1*) to (3*), further comprising a detectable label (5*) The peptide of any one of (1*) to (4*), further comprising a molecule which increases the half-life extension.

(6*) The peptide of any one of (1*) to (3*), further comprising a moiety that increases solubility of the molecule.

(7*) The peptide of any one of (1*) to (3*), further comprising at least one D-alanine at the amino-terminus and/or the carboxy-terminus.

(8*) A molecule according to any one of (1*) to (7*) for use as a medicine.

(9*) A molecule according to any one of (1*) to (7*) for use as an anti-bacterial agent.

(10*) A molecule according to any one of (1*) to (7*) for use as a diagnostic agent.

(11*) A pharmaceutical composition, comprising according to any one of (1*) to (7*) and a pharmaceutically acceptable carrier.

(12*) A method to produce an anti-bacterial peptide comprising the following steps:

(i) generating an in silico list of aggregation prone regions (APRs) with a length of 6-10 amino acids which APRs are identified in a bacterial proteome, (ii) synthesizing a number of 20-200 different peptides comprising an APR based on the following structure: $(A_{2i-1}\text{-APR-}A_{2i}\text{-}Z_i)_n$, wherein n is an integer from 1 to 4 and i increases from 1 to n with each repeat and each $A_{2i-1}$ and $A_{2i}$ are independently selected from 1 to 3 contiguous gatekeeper amino acids selected from R, K, D, E and P, (iii) testing said peptides for an anti-bacterial effect and producing an anti-bacterial peptide.

It is to be understood that although particular embodiments, specific configurations as well as materials and/or molecules, have been discussed herein for engineered peptides and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

1. Design and Screening of *E. coli* Specific Aggregating Peptides

In the present invention we used the statistical thermodynamics algorithm TANGO to identify aggregation prone regions (APR) in the proteome of *E. coli* strain O157:H7. This yielded 3535 sequences of at least 6 amino acids in length and a TANGO score of at least 20%. In order to generate efficient aggregation seeds, we employed a previously devised tandem repeat design [19, 21], in which the APRs are repeated once and separated by a linker. Given the length limitation on solid phase peptide synthesis with regard to yield and purity, we focused on the 1542 APRs with a length of 7 amino acids. In order to maximize the potential of these peptides to induce aggregation in *E. coli*, we ranked the APRs by their frequency of occurrence throughout the *E. coli* proteome, allowing a single amino acid mismatch, and selected the first 75 most frequently occurring sequences from this list (Table 4). In the design pattern, and in order to increase the colloidal stability of these aggregating peptides, the APRs are flanked by aggregation gatekeepers, a class of residues that was previously shown to reduce aggregation kinetics[22-24]. Since positively charged residues have been shown to help bacterial uptake[25], we selected arginine to obtain the following peptide layout: R-APR-RR. To generate the tandem we used a single proline residue as a linker between the gatekeeper-flanked APRs. In addition to the 75 peptides generated in this fashion, we added 2 variants of each of the first 25 peptides in the list by randomly mutating one residue in the first APR repeat to arginine to further modulate the aggregation propensity of the peptides (Table 4). All the peptides were generated using solid phase synthesis at 200 nmole scale and dissolved in DMSO to a theoretical stock concentration of 2 mM (assuming 100% synthesis efficiency). Peptide activity on the growth of *E. coli* O157:H7 was measured at dilutions of the peptide corresponding to concentrations of 1, 6, 12 and 25 µg/mL. Although no peptide was able to inhibit bacterial growth at the highest dilution, 43 of them were active against *E. coli* O157 at 25 µg/mL, of which 11 were active at 12 µg/mL and 6 had an apparent Minimum Inhibitory Concentration (MIC) value of 6 µg/mL (Table 5). We used the CAMP software prediction algorithm, which is trained to identify known AMPs[26], to analyse our sequences and found that 90% were predicted to be antibacterial, irrespective of whether we found them to be active or not (65% were inactive). The Matthews Correlations Coefficient (MCC) with the measured activity was 0.1 at 12 µg/mL and 0.24 at 25 µg/mL. This indicates that the key properties of known AMPs, such as hydrophobicity and charge, captured by a machine learning algorithm are not sufficient to predict the antibacterial activity of aggregating peptides and that our peptides work by a mechanism not incorporated in the current prediction algorithms.

2. Activity and Selectivity of *E. coli* Derived Aggregating Peptides

We selected, resynthesized and HPLC purified several peptides from the screen, i.e. P2 (RGLGLALVRRPRGLGLALVRR, SEQ ID NO: 1), P5 (RALLTTLLRRPRALLTTLLRR, SEQ ID NO: 3), P14 (RGLLALLARRPRGLLALLARR, SEQ ID NO: 6) as well as P105 (RALLRTLLRRPRALLTTLLRR, SEQ ID NO: 5) and confirmed Minimum Inhibitory Concentration (MIC) and Minimum Bactericidal Concentration (MBC) values of HPLC-grade purified peptides to be 6-12 µg/mL (see Table 1). Analysis of the rate of peptide bactericidal activity against *E. coli* O157:H7 (at MIC concentration) showed that the peptides exerted full bactericidal effect within 30 min to 2 h (FIG. 1A). Cross-section transmission electron microscopy of peptide-treated bacteria revealed the widespread presence of large inclusion bodies, a hallmark of protein aggregation in *E. coli*, suggesting that the peptides act by interfering with bacterial proteostasis (FIG. 11B, C, D). These inclusion bodies, which are also called Large Polar Aggregates, are mostly located at the poles of the bacterial cells, as expected for these structures due to nucleoid occlusion[27]. Interestingly, when bacteria were repeatedly passaged on sublethal concentrations (50% of MIC) of the active peptides for a period of 36 days, no development of resistance was observed, whereas this was the case for the control antibiotic ampicillin (FIG. 1E). As a first indication of specificity of the peptides, we evaluated their hemolytic activity on human erythrocytes (FIG. 1F), which revealed the P2 peptide (RGLGLALVRRPRGLGLALVRR, SEQ ID NO: 1) to have a favourable, (particularly, the most specific) toxicity profile towards *E. coli* strain O157:H7. This was further confirmed by CellTiter Blue (FIG. 1G) and LDH release (FIG. 1H) assays on HeLa cells. The specificity of P2 for *E. coli* O157:H7 was estimated by determining the concentration at which bacterial growth is 50% inhibited (IC50=1.5 µg/mL) and compared to the concentration at which the peptide induces 50% lysis of human erythrocytes (LC50=1100 µg/mL) yielding a therapeutic ratio of 730. Based on this observation, P2 was selected for further characterization and will henceforth be called colpeptin1. As a control, we generated mutants of colpeptin1 in which we introduced proline substitutions at different positions in the APRs (Table 1), which conserves the hydrophobicity but disrupts the beta-sheet propensity and hence reduces the aggregation propensity of the peptides. Due to the conservation of hydrophobicity and charge of the mutant peptides, the CAMP prediction software again classifies these controls as antimicrobial. However, when we treated bacteria with the control peptides, we obtained MIC values of more than 200 µg/mL, indicating that beta-structure formation is key to the antimicrobial activity of our peptides and confirming that the mode of action of other AMPs is not predictive for the antibacterial activity observed with our sequences. In a next step we evaluated the activity of colpeptin1 against various bacterial strains and correlated this with the sequence conservation of the HcaB protein present in the bacterial strains. The data are shown in Table 2.

3. Colpeptin1 Forms Soluble Oligomeric Beta-Structured Aggregates that Mature into Amorphous Aggregates Analysis of colpeptin1 by electrospray ionisation-mass spectrometry linked to ion mobility spectrometry (ESI-IMS-MS)[28] revealed that immediately following solubilisation of colpeptin1 in 100 mM ammonium acetate buffer the peptide is not only monomeric, but also readily forms soluble oligomers ranging from dimers up to 9-mers, and likely higher order (FIG. 1I). Consistent with this, the main species observed by Dynamic Light Scattering (DLS) upon dissolving have apparent hydrodynamic radii of approximately 1-2 nm, which quickly grow to large particles within a few hours (FIG. 1J). The composition of the colpeptin1 solution evolves over time towards larger species, which in the mass spectrometer is paralleled by a consumption of the smaller species (the larger being outside the detection range of the instrument). A study of the solubility of the peptide over time using ultracentrifugation also shows aggregation, with less than 60% of the peptide remaining in solution by ultracentrifugation 30 min after dissolving (FIG. 1K). The insoluble fraction collected in this manner was brought back into suspension (in 10% of the original volume) and the secondary structure content was analysed using Fourier Transform Infrared Spectroscopy (FTIR), which shows major peaks around 1622 and 1641, consistent with beta-structure formation (FIG. 1L). Mature aggregates were only mildly positive for the amyloid-specific dye pentameric formyl thiophene acetic acid (p-FTAA)[29-31] (FIG. 1M). By transmission electron microscopy mature aggregates mainly formed amyloid-like aggregates, which occasionally assembled into ordered fibrils (FIG. 1N). Taken together, these features are consistent with colpeptin1 forming β-structured soluble oligomers that slowly convert to insoluble fiber-like aggregates. Upon exposure of Colpeptin1 to polyphosphate, a naturally abundant form of phosphate in *E. coli* that was previously shown to facilitate amyloid formation[32], the peptide displays typical amyloid-aggregation kinetics as measured using pFTAA fluorescence (FIG. 1O). An analysis of a proline substituted and inactive control of colpeptin1 (termed P-colpeptin1) showed that upon solubilisation under identical conditions, P-colpeptin1 is almost completely soluble and does not adopt a beta-structured conformation, although sedimentation analysis still reveals aggregation on a longer timescale (FIGS. 1K & L).

4. Colpeptin1 Displays In Vivo Activity Against *E. coli* in a Bladder Infection Model In order to test the in vivo potential of colpeptin1 we treated a co-culture of mammalian (HeLa) cells and *E. coli* O157:H7 with colpeptin1 and observed the preferential accumulation of colpeptin1 in bacteria but not in mammalian cells (FIG. 2A). Finally we found that colpeptin1 incubated in 25% or 50% human serum for 2 hours was still able to inhibit bacterial growth at 25 µg/mL and 50 µg/mL (FIG. 2D). Given these positive results, we then established the tolerance of the Swiss mice to the peptide by performing a dose escalation experiment. We observed no acute adverse effects across the entire basic concentration range to the basic physiological and behavioral parameters of the animals upon intraperitoneal administration of up to 30 mg/kg colpeptin1. The parameters observed included body weight, food and water consumption, home cage activity and locomotion. We subsequently treated a cohort of 6 mice with daily injections at the maximum tolerated dose for 18 days without any apparent adverse effects. The mice were allowed to recover for 3 days, at which point they were sacrificed and a survey of the major organs was undertaken, which revealed no major morphological signs of toxicity (Tables 6, 7 and FIGS. 5, 6). In addition an ELISA assay on the serum of these animals revealed no specific antibody response towards the colpeptin1 peptide (FIG. 2E). A limited biodistribution study in healthy animals following injection (IP or urinary tract) of a single dose of 10 mg/kg FITC-labelled colpeptin1 revealed a clear distribution of fluorescent material for at least 3 h after injection and a total clearance of the peptide after 24 h (FIG. 7). Based on these observations, we tested the antibacterial efficacy of the colpeptin1 in a mouse bladder infection model. In this model, an inoculum of 50 µL of a $10^8$ CFU/mL suspension of *E. coli* O157:H7 was delivered via the urethra to the bladder of healthy Swiss mice. 1 h post-infection, we administered a single injection of colpeptin1 at 10 mg/kg, either via the urethra (n=15) or intraperitoneally (n=15). 24 h after treatment, the animals were sacrificed and the bacterial titer in kidney, colon, bladder and ureter was determined by plating the macerated tissue (FIG. 2F-I). These experiments revealed a significant reduction of the bacterial titer in the different organs of colpeptin1 treated animals of more than 2-log fold, both after intraperitoneal and urethral delivery (p-val<$10^{-4}$ compared to buffer control & p-val<$10^{-4}$ compared to non-aggregating P-colpeptin1 control, anova with Tukey post-test). The effect was comparable to that of orally dosed ampicillin (20 mg/kg) that was used as a control, indicating that the antimicrobial activity of colpeptin1 against *E. coli* is maintained in vivo.

5. Colpeptin1 Uptake Results in IB Formation and Growth Inhibition

To study its mode of action, we derivatized colpeptin1 with fluorescein isothiocyanate (FITC) and established that the conjugate retained its antibacterial activity (MIC=3 µg/mL against *E. coli* O157: H7) and quantified colpeptin1 uptake by flow cytometry. Analysis of colpeptin1 uptake by *E. coli* O157:H7 showed that after 15 minutes already, 97.7±2.9% (N=4) of the cells are positive for FITC (FIGS. 3B & F), increasing to nearly 100% after 1 h and beyond (FIG. 3C-F). In parallel, fluorescence microscopy of treated *E. coli* O157:H7 at MIC concentration confirmed no enrichment at the cell membrane of FITC-colpeptin1, but rather showed a clear accumulation of fluorescence in intracellular polar inclusion bodies (IBs) from 15 minutes onwards (FIG. 3G) that persisted at later time points (FIG. 3H). In addition, colpeptin1 induced IBs could be stained with p-FTAA, a dye that specifically binds to amyloid-like aggregates as well as disease-associated protein inclusion bodies[31], confirming the ordered beta-sheet rich aggregated protein structure of these inclusions (FIGS. 3I & J). This demonstrates that colpeptin1 uptake and IB formation occur in close succession. Kinetics of bacterial cell death as measured by CFU determination after colpeptin1 treatment (FIG. 3K) also closely follow peptide internalization and coincide with the appearance of IBs after 15 min treatment (50% after 15 min). On the other hand, bacterial cell death as monitored by Propidium Iodide (PI) uptake as a result of membrane permeabilisation increased more slowly (2.1±1.3% after 15 min to 85±13.2% after 3 h, FIGS. 3A-E & 3L), showing that at short treatment times, significant growth inhibition is established coincidentally with IB formation but before membrane permeability can be observed. In agreement with this, morphological analysis of bacteria treated at 4×MIC for 2 h and untreated controls using Scanning Electron Microscopy (SEM, FIG. 3M, N, O) shows that colpeptin1-treated bacteria appear shrunken but no cellular leakage is apparent. Together these data suggest a chain of events in which colpeptin1 internalisation is coincidental with colpeptin1-containing IB formation and bacterial growth inhibition.

6. Colpeptin1 Induces Lethal Bacterial Proteostatic Collapse

Bacterial IB formation is a common event associated with cellular stress including exposure to heat and recombinant protein (over)expression. This process however is often transient and reversible and does not necessarily lead to bacterial cell death. In fact, recombinant protein production in bacteria relies to a large extent on the ability of bacteria to cope with IBs. As an example, we measured the consequences of overexpressing the highly aggregation-prone core domain of the human p53 protein (p53CD) on growth (FIG. 4A) of *E. coli* BL21 cells, which are routinely used for recombinant protein production. Although p53CD expression resulted in a delay of the exponential growth phase, consistent with cellular stress resulting from the overexpression, there was no effect on colony formation, showing the stress is not lethal. In order to understand why colpeptin1 induced IB formation is irreversibly toxic we compared the composition of IBs purified from *E. coli* O157:H7 cells treated with colpeptin1 at MIC concentration for 1 h with IBs purified from *E. coli* strain BL21 overnight overexpressing p53CD. Inspection of the resulting samples by TEM confirmed the successful purification of these IBs (FIG. 4C). The composition of IBs was subsequently analysed by coomassie-stained SDS-PAGE (FIG. 4D). The overall pattern of coomassie staining revealed that a large number of similar bacterial proteins are trapped in the IBs of both colpeptin1 treated *E. coli* O157:H7 and p53 overexpressing *E. coli* BL21, but not in untreated bacteria suggesting a common molecular machinery associated with IB formation. Among the IB trapped proteins, a number of molecular chaperones that are known to occur in inclusion bodies could be detected, including the bacterial Hsp70 homolog DnaK, the Hsp60 chaperonin GroEL, the ribosome associated chaperone Trigger Factor (TF) and the bacterial Hsp40 DnaJ (FIG. 4E). The polar localization of a fluorescently traceable DnaK-mCerulean3 fusion protein (the latter moiety comprising a blue fluorescent protein) in *E. coli* K12 MG1655 cells exposed to colpeptin1 confirms the association of DnaK with IBs (FIG. 4F). Our data show that colpeptin1 and p53CD IBs share a number of proteins, including many chaperones and ribosomal proteins which are common constituents of IBs. Second, in addition to this common core, we find that colpeptin1 IBs contain many more additional proteins than p53CD IBs. This shows that the toxic impact of colpeptin1 treatment corresponds to a more extensive proteomic impact than the effect of p53CD overexpression. This observation is in line with our initial design hypothesis aiming at inducing proteostatic collapse by aggregation of multiple proteins.

7. Colpeptin1 Induces the Co-Translational Aggregation of Direct Sequence Targets In accordance with our design, the colpeptin1 APR is highly redundant in the *E. coli* proteome and can also be found in 18 other *E. coli* proteins with a single mismatch (Table 8) and 158 proteins with a double mismatch. In the case of colpeptin1, its direct APR match is the GLGLALV (SEQ ID NO: 128) sequence from HcaB, where SEQ ID NO: 128 begins at position 17, and ends at position 23, of the HcaB sequence. HcaB (3-phenylpropionate-dihydrodiol/cinnamic acid-dihydrodiol dehydrogenase) is a non-essential enzyme in the aromatic compound metabolism that occurs at very low abundance (0.015 ppm according to PaxDB[33]). Taguchi and co-workers have previously determined the solubility of the entire *E. coli* proteome including HcaB using a cell-free translation system showing that HcaB is a highly aggregation prone protein that is highly dependent on GroEL/ES for folding[34]. In a next step we cloned HcaB into an inducible vector for recombinant expression and chromatographically purified the protein from lysates of *E. coli* BL21:DE3 cells overexpressing HcaB. Using this material we performed an immunisation scheme in mouse (see materials and methods), yielding antiserum against HcaB in a Western blot, revealing a band at the right molecular weight, as well as 2 off-target bands (FIG. 4H). Using this antiserum, we compared the effect of colpeptin1 treatment (1 h at MIC concentration) on the presence of HcaB in the soluble and insoluble fraction of *E. coli* O157:H7, endogenously expressing HcaB, and *E. coli* BL21 cells overexpressing HcaB (FIG. 4H), confirming the accumulation of HcaB in the inclusion body fraction of colpeptin1 treated cells. This confirms that HcaB does aggregate upon treatment with colpeptin1. When calculating the translational efficiency of these genes based on Tuller's method[35], which uses typical decoding times of individual codons, we found that the translational efficiency of the colpeptin1 target proteins was significantly higher (student t test, $p<0.001$, FIG. 4J) than for undetected putative targets, suggesting that a high translation rate might facilitate colpeptin1 induced aggregation. To verify this hypothesis, we measured the MBC value of colpeptin1 in the presence of the macrolide antibiotic erythromycin, which is a bacteriostatic drug that acts by blocking the polypeptide exit channel in the ribosome. Strikingly, we observed a marked desensitization of bacteria (*E. coli* O157) (MBC>100 µg/mL) to colpeptin1 after pretreating the cells with 100 µg/mL erythromycin for 2 h to block translation during the exposure to colpeptin1, strongly supporting a co-translational induction of protein aggregation as the mode of action.

The colpeptin1 APR is highly redundant in the *Acinetobacter baumannii* proteome and can also be found in 18 other *A. baumannii* proteins with a single mismatch and 268 proteins with a double mismatch (Table 9), supporting the observed bactericidal activity of colpeptin1 against both *E. coli* and *A. baumanii*. (FIG. 9)

8. Colpeptin1 Induces a Multi-Target Aggregation Cascade Leading to Proteostatic Collapse The question then remains how the aggregation of colpeptin1 and its detected targets relates to the aggregation of the other proteins found in colpeptin1 IBs. A first possibility is that colpeptin1-induced proteostatic collapse results from saturation of bacterial chaperones. In order to test this possibility we determined the effect on colpeptin1 activity of major bacterial chaperones and proteases in the *E. coli* K-12 BW25113 strain (KEIO collection[37]) and found that from the individual knockouts of the principal proteostatic components of *E. coli*, only DnaK had a mild effect on colpeptin1 activity (Table 3). Furthermore, previously designed peptides that induce lethal aggregation in *Staphylococcus epidermidis*[19], using tandem repeats of strain specific APRs flanked by positive charges are not active against Gram-negative *E. coli* and vice versa even though these peptides are internalized. Together these data suggest that saturation of chaperones and the proteostatic system by aggregating peptides is not the principal mechanism of action of colpeptin1. Alternatively, and in line with our hypothesis, APR redundancy drives proteostatic collapse by a sequence-specific cascade of protein aggregation. We reasoned that the primary colpeptin1 targets have additional APRs in their sequence and these form colpeptin1-induced co-aggregated proteins which are also present in these IBs, which proteins on their own can be further connected by an aggregation cascade determined by secondary APRs in primary colpeptin1 targets. Going one step further, still an additional number of proteins can be connected in a similar manner by a third layer, finally leaving few proteins unconnected in the cell.

To compare, the p53CD has one dominant APR according to TANGO (ILTIITL, SEQ ID NO: 223)[38], which has no exact match in the proteome of *E. coli* O157:H7, but it has 3 proteins that have an APR with one mutation, and 50 proteins with an APR that is 2 mutations away. None of these proteins could be detected in the IBs (data not shown), demonstrating that p53CD aggregation is a much more isolated event in sequence space. The proteins detected in IBs of p53CD on the other hand consist mainly of chaperone clients[39-46], confirming that p53CD aggregation constitutes a proteostatic stress but which contrary to colpeptin1 does not cause a proteostatic collapse and is not lethal to the bacterial cell.

9. Determination of the MIC Values for 28 Different Peptides Against a Set of Bacteria In this experiment a set of 28 peptides of which the amino acid sequences are depicted in Table 4, were administered to the *E. coli* BL2 strain, *Acinetobacter baumannii*, *Kiebsielia pneumoniae* and *Pseudomonas aeruginosa*. The MIC values were determined and are depicted in FIG. 8.

10. Colpeptin1 has Broad within Species Reactivity and is not Affected by the Pathogen Resistance Profile In this experiment we assessed the potency of Colpeptin1 against a number of clinical isolates of *E. coli* and a number of clinical isolates of *Acinetobacter baumannii* (including 2 reference strains). FIG. 9 (upper panel) lists the MIC values of Colpeptin1 (indicated as P2 in the FIG. 8) against a number of clinical isolates of *E. coli*. FIG. 9 (lower panel) lists the MIC values of Colpeptin1 (indicated as P2 in the FIG. 9) Sensitivity (S) or resistance (R) or intermediate resistance (1) of the clinical isolates against 12 different antibiotics is depicted in the panel (data according to CLSI criteria for the specific antibiotics). Our data show that that colpeptin1 has a broad within species activity and that the MIC values are not affected by the antibiotic pathogen resistance profile, both for *E. coli* and *Acinetobacter baumannii*.

Materials and Methods

1. Bio-Informatics Analysis

Protein sequences for various bacterial strains were obtained from UniProt (*Nucleic Acid Res*. (2008) 36, D190-5), and redundancy was removed using the cd-hit algorithm (Fu L. et al (2012) *Bioinformatics* 28, 3150). We used the TANGO algorithm for all APR identifications in this manuscript. We used a cutoff on the TANGO score of 5 per residue since this gives a Mathews Correlation Coefficient between prediction and experiment of 0.92 (Fernandez-Escamilla A M et al (2004) *Nat. Biotechnol.* 22, 1302). The settings of TANGO were Temperature=298K, pH=7.5, Ionic Strength=0.10 M.

2. Peptide Synthesis

During the screening stage peptides were synthesized using standard solid-phase peptide synthesis (JPT, Berlin, Germany). Peptide hits were resynthesised in-house at higher scale using an Intavis Multipep RSi synthesis robot and HPLC purified to 95% using Zorbax SB-C3 semi-preparative column (Agilent, USA) on a Prominence HPLC (Shimadzu, Japan). Peptides were lyophilized and stored at −20° C. prior to use.

3. Bacterial Strains and Growth Conditions

Gram negative bacterial strains were cultivated in Luria-Bertani (LB) broth (Difco) and gram positive bacteria strains were grown in a rich medium, brain heart infusion (BHI) broth (Difco, Sparks, MD) at 37° C. Whenever required, growth media were supplemented with appropriate antibiotic to the medium or plates. *Escherichia coli* DH5α was used for cloning and plasmid amplification. For selection of antibiotic resistance colonies, *E. coli* carrying plasmid were grown in LB medium supplemented with 25 µg/mL ampicillin or 100 µg/mL Erythromycin (sigma). Bacterial CFU counting was done on blood agar plates (BD Biosciences). Species identification and antibiograms for all clinical isolates were performed using MALDI-TOF and VITEK® 2 automated system (bioMérieux).

4. MIC Determination

The MICs of active peptides were determined via the Broth microdilution assay according to the EUCAST guideline, which were performed in 96-well polystyrene flat-bottom microtiter plates (BD Biosciences). Briefly, a single colony was inoculated into 5 mL LB medium and grown to the end-exponential growth phase in a shaking incubator at 37° C. Cultures were subsequently diluted to an $OD_{600}$ of 0.002 ($1 \times 10^8$ CFU/mL) in fresh LB medium. 100 µL of LB medium with different concentration of peptides ranging from 100 µg/mL to 1 µg/mL were serially diluted to the sterile 96-well plate (at least 3 wells in each plate). Afterward, 100 µL of the diluted bacteria were pipetted into 96-well plates containing different concentration of peptides. In each plate, the grown bacteria with maximum concentration of carrier and medium were considered as positive and negative controls, respectively. Thereafter, 96-well plates was statically incubated overnight at 37° C. to allow bacterial growth. A multipurpose UV/VIS plate reader at $OD_{590}$ nm, 1 s shaking measured the absorbance of the growth bacteria using a Perkin Elmer spectrophotometer (1420 Multilabel Counter Victor 3).

5. Antibody and Antibiotic Product Codes

Anti-CLPB (Aviva, Catalog #ARP53790_P050), Anti-DnaK (Aviva, Catalog #OAED00201), Anti-Trigger Factor (Clontech, Catalog #M201), Anti-groEL (Abcam, Catalog #ab82592), Anti-DnaJ (Enzo Life Sciences, Catalog #ADI-SPA-410-D). Ampicillin sodium, CAS number 69-52-3, Duchefa Biochemie, catalog #A0104. Erythromycin, CAS Number 114-07-8, Sigma Aldrich, CAS Number 114-07-8, catalog #E5389.

6. Biophysical Characterization

Dynamic light scattering (DLS) measurements were made at room temperature with a DynaPro DLS plate reader instrument (Wyatt, Santa Barbara, CA, USA) equipped with a 830 nm laser source. Samples (100 µL PBS buffer, 2 mM peptide) were placed into a flat-bottom 96-well microclear plate (Greiner, Frickenhausen, Germany). The autocorrelation of scattered light intensity at a 90° angle was recorded for 10 s and averaged over 40 recordings to obtain a single data point. The Wyatt Dynamics software was used to calculate the hydrodynamic radius by assuming a spherical particle shape. Attenuated Total Reflection Fourier Transform Infrared Spectroscopy (ATR FTIR) was performed using a Bruker Tensor 27 infrared spectrophotometer equipped with a Bio-ATR II accessory. Spectra were recorded in the range of 900-3500 cm$^{-1}$ at a spectral resolution of 4 cm$^{-1}$ by accumulating 120 data acquisitions. The spectrophotometer was continuously purged with dried air. Spectra were corrected for atmospheric interference, baseline-subtracted, and rescaled in the amide II area (1500 to 1600 cm$^{-1}$). For Transmission Electron Microscopy (TEM) aliquots from peptide preparations were adsorbed to carbon-coated Formvar 400-mesh copper grids (Agar Scientific) for 1 min. The grids were blotted, washed, and stained with 1% (wt.vol-) uranyl acetate. Samples were studied with a JEOL JEM-1400 microscope (JEOL Tokyo, Japan) at 80 kV.

7. Time Killing Kinetic Assay

The time-kill kinetics study of the peptides was carried out to assess the killing rate of the bacteria at enough exposure time points. This study was done according to standard guide for assessment of antimicrobial activity using time-kill kinetics procedure. Selection of agent concentrations was guided by MIC endpoints.

Briefly, 20 µL of frozen cultures of *E. coli* O157:H7 were inoculated into 5 mL LB and grown to the end-exponential growth phase in a shaking incubator at 37° C. Cultures were subsequently diluted to an OD$_{600}$=0.002 (1×10$^8$ CFU/mL) in fresh LB medium (1 mL). To evaluate the effect of aggregators over time, bacteria were subjected to a concentration of different peptides at the MIC value for different periods of time (5 min, 10 min, 30 min, 1 h, till 6 h). After the defined contact period, 50 µl of each culture were serially diluted and plated on blood agar plates. Plates were overnight incubated at 37° C. without shaking. Positive and negative controls were bacteria treated with maximum used buffer and the LB medium, respectively. The number of viable organisms was counted as CFU/ml.

8. Multistep Resistance Development Study

The ability of the target strains to develop resistance to active compounds was evaluated by repeated subculturing in the presence of the half-MIC value of the active peptides over 30 days. Briefly, *E. coli* O157 cultures were grown in Luria Broth (LB) medium; the optical density of bacteria was then adjusted to an OD600 of 0.002 (equivalent to 1×10$^8$ CFU/mL). Then, bacteria were treated by the P2 peptide at half-MIC concentration, after a 24 h incubation period, the MIC's were tested by a micro-dilution assay according to the EUCAST guideline and the bacteria re-cultured in the presence of the half-MIC value of the respective aggregator. Ampicillin was used as the positive control in this experiment.

9. Scanning Electron Microscopy

For scanning electron microscopy (SEM) *E. coli* O157 bacteria in end-exponential growth phase were diluted to a density of 10$^8$ CFU/mL and treated with supra-MIC concentrations of peptides. After 2 h treatment, bacteria were fixed with 2% glutaraldehyde for 1 hour. 1% Osmium tetroxide (OsO4) was used as postfixation in 0.1 M sodium cacodylate buffer for 1 h. Samples were washed three times with cacodylate buffer (0.1 M sodium cacodylate) for 10 min at room temperature. The samples were dehydrated with a graded ethanol series (50%, 70%, 96%, 100% alcohol). After the dehydration step, samples were dried by Hexamethyldisilazane (HMDS) for 1 h, and mounted on the specimen stubs and sputter coated with gold. A SEM-FEG microscope (JEOL JSM 6700F) with an accelerating voltage of 30 kV was used.

10. Cross-Section Transmission Electron Microscopy

*E. coli* at the end-exponential growth phase were washed twice and diluted with physiological water and subsequently treated with either 4× MIC value of specific aggregator peptides (Colpeptin1 or P2Pro2) or buffer for 2 h (Control group) at 37° C. After 2 h, bacteria were centrifuged at 6000 rpm for 4 min and pellets were fixed by 2,5% glutaraldehyde in 0,1M Na-cacodylate buffer pH=7,2-7,4 [+2.5 mM CaCl2+1 mM MgCl2] for 1 h. Then, the pellets were washed with cacodylate buffer, resuspended in 1,5% low melting point agarose (Sigma A4018) in cacodylate buffer (40° C.) and centrifuged at 6000 rpm, 4 min. The centrifuge tubes were placed on ice for 15 minutes, after which the tips containing the pellets were cut off and the pellets removed in a drop of cacodylate buffer. Pellets were cut in 1 mm$^3$ cubes (4° C.), post-fixed with 1% Osmium tetroxide (OsO4) in distillate water for 2 h and washed twice with distillate water. Thereupon the samples were dehydrated in a graded ethanol series (30, 50, 70, 90, 100%) 5 min each step at 4° C. while slowly rotating (ethanol 100%, 3 times repeated). Finally, cells were treated by propylene oxide twice 15 min at 4° C., infiltrated with a 1:1 mixture of epoxy resin and propylene oxide (60'@4° C., slowly rotate) and subsequently left in a mixture of 2:1 epoxyresin and propylene oxide overnight under a fume hood without caps. The next morning, samples were placed in 100% fresh epoxy resin, embedded in BEEM capsules in the evening and polymerized for 2 days in an oven at 60° C. Ultrathin sections were cut with a Leica ultracut UCT ultramicrotome and observed in a JEOL JEM1400 transmission electron microscope operated at 80 kV and equipped with an Olympus Quemesa 11 Mpxl camera.

11. In Vitro Haemolytic Activity Test

The hemolytic activities of peptides were determined by hemolysis against human erythrocytes. Pooled fresh blood was obtained and erythrocytes were collected by centrifugation 3000 rpm for 5 minutes (Anticoagulated by EDTAK) (Cristina et al. 2015). The pellet was washed three times with PBS and was diluted to a concentration of 8% in PBS. 100 µL of 8% Red blood cells solution was mixed with 100 µL of serial dilutions of peptides in PBS buffer in 96 well plates (BD Biosciences). The reaction mixtures were incubated for 1 h at 37° C. Thereupon, the plate was centrifuged for 10 minutes at 3000 rpm and 100 µL of supernatant was transferred to a sterilized 96-well plate (flat bottom). The release of hemoglobin was determined by measuring the absorbance of the supernatant at 405 nm. The hemolytic activity was determined as the minimal peptide concentration that caused hemolysis (minimal hemolytic concentration, MHC). Erythrocytes in 1% Triton and Max used concentration of vehicle were used as control of 100% and 0% hemolysis, respectively.

12. In Vitro Mammalian Cytotoxicity

Mammalian cytotoxicity was measured using the LDH release (Roche, Mannheim, Germany) and CellTiter Blue (Promega) methods. Briefly, HeLa cells (obtained from Bart De Strooper lab, tested to be *mycoplasma* free) were seeded in 96-well round bottom plates at a concentration of $3\times10^5$ cells/mL in Dulbecco's Modified Eagle's Medium and treated by different concentrations of peptides. Cells treated with 1% Triton™ X-100 and vehicle were considered as positive and negative controls, respectively. Micro-plates were incubated at 37° C., 5% $CO_2$ and 90% humidity for 4 hours. The micro-plate was centrifuged at 1350 rpm for 10 minutes. 100 µL of supernatant was transferred into clear 96-well flat bottom microplates. In order to determine LDH activity in the supernatants, 100 µl reaction mix (catalyst and dye solution) were added to each well and incubated for 30 min at RT in the dark and the LDH reaction was stopped by adding 100 ul of the Stop solution. The absorbances of the samples were measured at 490 nm. The cell viability was calculated using the formula: (exp. value−negative control value)/(positive control value−negative control value)*100. The amount of absorbance is proportional to the number of living cells and corresponds to the cells' metabolic activity.

13. Cloning and Expression of the hcaB Gene in *E. coli* ATCC 25922 Strain

The coding regions of *E. coli* O157 HcaB were amplified using hcaB specific primers (ATGTCGACATGAGC-GATCTGCATAACGA (SEQ ID NO: 224), ATGTCGA-CATGGAGCGATTTATCGAAGAAGGC (SEQ ID NO: 225), ATCCCGGGTTAAAGATCCAACCCAGCCG (SEQ ID NO: 226)) containing additionally a SalI and SmaI restriction site for cloning purposes. Two truncates versions of the gene, one with the targeted gene part, APR, and the other one without the target region were designed. Genomic DNA (gDNA) of bacteria *E. coli* O157 strain, a clinical isolate was used as a template. The amplicons were ligated into SalI/SmaI-digested pCN68 *E. coli-Staphylococcus* shuttle vectors yielding different truncated version pCN-hcaB. In this plasmid, PblaZ is the promoter. Ampicillin (25 µg/mL) or erythromycin (100 µg/mL) was used as the selection marker. Correctness of cloning was confirmed first by restriction enzyme digestion, PCR, and nucleotide sequence analysis of the insert and then sequencing.

14. Macrolides and Peptides Interaction

To evaluate the effect of peptides in the presence of Erythromycin, *E. coli* O157 was grown in 5 ml of LB (Luria-Bertani). Exponential-phase cultures were then diluted to $10^8$ cell/ml. Bacteria was treated by Erythromycin at the concentration of 100 ug/ml for 3 h to stop growing at 37° C., without shaking. Different concentrations of peptides (from 100 ug/ml to 0.75 ug/ml) or buffer were plated in 96 well with at least 3 times replicate wells (50 ul). 50 ul of erythromycin treated bacteria was added to each wells and 96 well plate was incubated for 2 h at 37° C. After 2 h, bacteria was serially diluted and cultured on blood agar plates. Plates were incubated at 37° C., overnight. The number of living cells were quantified by CFU counting.

Fluorescence microscopy of co-cultures of Bacteria and mammalian cell conjugated with FITC labeled peptides For imaging purposes, human HELA cells were grown on small cell view cellular dish with glass bottom (Greiner Bio-One/GmbH/35 mm ref: 627860) to form a confluent monolayer. Thereupon, cells were infected with 200 µL of overnight culture of *E. coli* O157 strain with FITC peptide (3× MIC) for 24 h. Cells were stained with CellMask Deep Red plasma membrane dye and 1 µl of NucBlue reagent for 30 min (Invitrogen), then medium was removed and 2 ml paraformaldehyde 4% was added to the plate for fixation. Plate was incubated for 6 h at RT. The co-cultured cells were washed with 3× with 1 mL saline prior to imaging.

15. Staining with Luminescent Conjugated Oligomers (LCOs)

200 µL of end-exponential culture *E. coli* O157 were washed with PBS for three times, the bacterial numbers were adjusted to $10^8$ cells and afterward bacteria were treated with peptides (at MIC) or Pro2 peptides as control for 2 h. After 2 h, cells were incubated with 1 µL of the LCO dye p-FTAA for 1 h and 30 min. The absorption and emission spectra were measured at 480 to 600 nm.

16. Flow Cytometry Analysis of Bacteria Using Labeled Peptides and Propidium Iodide (P)

Using a double staining technique with propidium iodide (PI) and FITC peptides, killing rate and peptides uptake were evaluated in a two dimensional analysis. Briefly, end-exponential growth phase *E. coli* O157 cells ($10^8$ CFU/mL) were washed with PBS and treated by peptides (Col-peptin11 or Pro2/FITC labeled) at MIC value for different time periods. Treated bacteria were again washed with PBS buffer three times. 1 ul of PI (Invitrogen) was added to the bacteria, and after incubated for 5 min, the mixture was aliquoted (500 µL) into FACs tubes. To correlate the activity of the peptides with cell death, the fluorescence intensity was measured in two channels using the Gallios™ Flow Cytometer, PI: excitation 536 nm and emission 617 nm, FITC: excitation 490 nm and emission 525 nm.

17. Inclusion Body Purification 20 mL of overnight culture of bacteria was centrifuged for 30 min at 6000 rpm and washed by physiological water. Bacteria were treated by peptide at MIC for half killing time, afterward the bacterial pellets were washed by 10 mL buffer A (50 mM Hepes pH 7.5, 300 mM NaCl, 5 mM Beta-Mercapto ethanol, 1.0 mM EDTA) and centrifuged at 4° C. for 30 min at 6 k rpm. The supernatant were discard and 20 mL of Buffer B (Buffer A plus 1 µg/mL Leupeptin, 0.1 mg/mL AEBSF) was added to the bacterial pellet. In order to break the cells, a Glen Creston Cell Homogenizer with pressure set to 20000-25000 psi was used and in addition, the suspensions were sonicated (Branson Digital sonifier 50/60 HZ) on ice with alternating 2 min (15 pulse at 50% power with 30 sec pause on ice, until completing 2 min total sonication time). The lysed cells were centrifuged at 4° C. for 30 min at 10 k rpm. The precipitated fraction was afterwards re-suspended with 10 mL Buffer D (Buffer A plus: 0.8% V/V Triton X-100, 1% Sodium Deoxycholate) and the suspension was sonicated to ensure the pellet is completely dissolved. This step was repeated 3 times. Centrifugation was performed at 4° C. for 30 min at 10.000 rpm. Finally to solubilize IB, the pellet was suspended in 1 mL of buffer F (50 mM Hepes pH 7.5, 8.0 M urea) per gram of precipated fraction.

18. Peptides Activity and Stability in Presence of Serum

Briefly, in order to get human serum, the fresh blood was kept at RT (room temperature) for 20 min to be clot. The tube was then centrifuged at 3000 pm for 10 min and serum separated. Serum was diluted into RPMI medium (50%) and peptides with different concentration of 5 µg/mL, 25 µg/mL and 50 μg/mL were added to each well. After 2 h incubation, End-exponential *E. coli* O157 culture washed three times by PBS (8000 rpm, 10 min). The number of bacteria then adjusted to $9 \times 10^8$ cells in RPMI medium with or without Serum. After 2 h incubation, bacteria were serially diluted and were cultured on blood agar plats. Plates were then incubated at 37° C. overnight. The numbers of living bacteria were quantified as the number of CFU/ml (colony-forming units).

19. HcaB Purification and Antibody Production

The coding whole *E. coli* hcaB gene (SE2232, Taxonomy ID: 83333) was amplified using hcaB-specific primer (CATATGATGCATCATCACCATCACCACAGC-GATCTGCATAACGA (SEQ ID NO: 227) and CCTAGGT-TAAAGATCCAACCCAGCCG (SEQ ID NO: 228)) with additionally NdeI and BamHI restriction site (underlined and italic) for cloning purposes. Anti-6X His (bold) tag used as a tag on the recombinant proteins to facilitate protein purification. Genomic DNA (gDNA) of *E. coli* strain O157 was used as a template. The amplicon was ligated into NdeI/BamHI-digested pET11C plasmid as a component of a system for protein expression in *E. coli* yielding pET-his-hcaB. In this plasmid, T7 RNA polymerase (highly active constitutive promoter) was the promoter. Ampicillin was used as the selection marker. All recombinant plasmids were replicated in *E. coli* BL21 to have BL21 pET-his-hcaB. Correctness of cloning was confirmed by restriction enzyme digestion, and nucleotide sequence analysis of the insert. Protein purified as described previously (Luminy and Cedex 2011). Briefly, *E. coli* BL21 pET-his-hcaB was grown in 1 L Luria-Bertani (LB) broth with 100 μg/ml ampicillin and 1 mM isopropyl-β-D-thiogalactopyranoside (IPTG) in 37° C., overnight with shaking. Afterwards, by centrifugation (4,000 rpm, 10 min, 4° C.) the cells harvested and re-suspended in 25 ml lysis buffer (PBS pH 7.5, 1 mM b-mercaptoethanol plus 1 tablet protease inhibitor Mini, EDTA-freelyse), bacteria lysed by French pressed and stirred in 4° C. with adding Dnasel and whole proteins were purified. To get rid of aggregation, we kept the proteins on the ice and then filtered. HcaB protein purification performed by AKTA FPLC system, which is a fully automated liquid chromatography system, where HcaB protein purified using HiPrep™ HP 5 ml column. Before actual purification run, the AKTA were stripped, charged, and blanked. The Purification was done by program in AKTA Xpress. The purified proteins collected from different tubes and combine fractions and kept at 4° C. Purified proteins were checked by running that on SDS gel. Three Swiss mice immunized twice intraperitoneally, in 10 days. The first injection was administered with a mixture of HcaB protein (50 ug/mouse) and Complete Freund's adjuvant (CFA; Sigma) (1:1). In day tenth, a booster injection (protein and Incomplete Freund's adjuvant (IFA; Sigma) performed after titration of the antibody by ELISA. Then from the serum, the total immunoglobulin Gs (IgGs) purified by absorption to a protein G column (GE Healthcare) according to the manufacturer's instructions.

20. Experimental Animals

Female swiss mice from 5 to 8 weeks (20 and 23 g) were used for the experiments. The animals were used in experiments after a period of 3 days of adaptation to the experimental cages, with regular 12 h light-dark periods and ambient temperature of 20° C.

21. In Vivo Toxicity Test

The procedures used in the assays were approved by the local Animal Ethical Committee and conform to international standards of animal welfare (Approval P067/2015 of the Ethical Committee of KU Leuven). A safe concentration of 30 mg/kg dose achieved from escalation experiment and observed no acute adverse effects upon intraperitoneal administration. Briefly, 5-6 week-old Swiss females were divided into 3 groups (6 animals/group) and administered 30 mg/kg of Colpeptin1 (group A) or vehicle (physiological water pH 7.5) (group b) once a day for 18 days via IP injection. During the treatment period the clinical, physiological and behavioral parameters including body weight, food and water consumption, body condition score, home cage activity and locomotion were constantly monitored and recorded.

Three days after the last administration animals were anesthetized and blood was collected using a standard retro-orbital puncture from each animal. Next, the mice sacrificed and underwent complete necropsy with gross examination and organ weights. The organs (Heart, Liver, Spleen, kidney, bone marrow, Brain, Lung) were sampled and immersion fixed in 4% paraformaldehyde. Formalin-fixed tissues after dehydration were routinely processed and embedded in paraffin blocks for histopathological examination. 5 μm thick sections taken from these blocks (Thermo Scientific Microm HM355S microtome) were then stained with Hematoxylin and Eosin (Leica ST5010 Autostainer XL) and evaluated under a Leica DM 2500 light microscope by a board-certified veterinary pathologist. Hematology examination was performed using an automate high-resolution flow cytometer, Abbott Cell-Dyn 3700.

22. The Urinary Tract Infection Model 8 weeks old Swiss female mice were used for the urinary tract infection model as described previously[4]. Briefly, mice were anesthetized by intraperitoneal administration of Nembutal 10% then with fingers gently the bladder of mouse was massaged and pushed down on to expel remaining urine. Thereafter, the anesthetized mice were inoculated transurethrally with 50 μl of bacterial suspension slowly ($1 \times 10^8$ cfu/ml) by sterile catheter in the bladder over 5 s in order to avoid vesicoureteral reflux through a surgical microscope. We estimated the sample size as follows: allowing a type I error rate of 0.05, a type II error 0.2 and estimating the maximum standard deviation of the CFU determination at 1 log CFU, we calculated that a sample size of 15 would allow us to reliably detect an effect size of 1 log CFU difference between treated and untreated. After 1 h mice were randomized and divided into 5 groups (15 mice/groups) group A and B received 10 mg/Kg Colpeptin interaperitoneally or transurethrally, respectively. Group C received P2Pro2 peptides (Proline substitutions) via transurethrally. Group D received the Ampicillin orally as the positive control and Group D received the vehicle (physiological water). The catheter was then removed immediately after inoculation. 24 h post infection, mice were sacrificed and Kidney, Bladder, Ureter, Colon were washed with PBS and homogenized. The homogenized tissues were serially diluted and were cultured on blood agar plates. The plates were kept in 37° C. overnight. The rate of bacteria was measured by CFU value. Blinding: Sample preparation and treatment of the animals was performed by L.K. and L.K., who also performed the CFU determination, however between treatment and readout the animals were randomly shuffled by P.C. and the key to the grouping was not revealed until after all the results were in.

23. Construction of E. coli MG1655 dnaK-mCer3

To construct E. coli MG1655 dnaK-mCer3, plasmid pGBKD-mCer3 was first constructed by integrating a mCer3 amplicon, generated with primers 5'-AGAAT-TCGGCAGCGGCAGCGGCAGCGT-GAGCAAGGGCGAGGA-3' (Fw) (SEQ ID NO: 229) and 5'-AGGATCCTTACTTGTACAGCTCGTCCA-3' (Rev) (SEQ ID NO: 230), into pGBKDparSpMT1[5] using EcoRi and BamHI restriction sites. In addition to adding the respective restriction sites to the end of the amplicon, these primer pairs also add a flexible linker (encoding GSGSGS[6]) facilitating folding of fluorescent fusion proteins constructed with these sequences. A mCer3-frt-cat-frt cassette was subsequently PCR amplified from plasmid pGBKD-mCer3 using primer pair (Fw)
(SEQ ID NO: 231)
5'-AGATGACGATGTTGTCGACGCTGAATTTGAAGAAGTCAAAGACAAAAAAG
GCAGCGGCAGCGGCA-3'
and (Rev)
(SEQ ID NO: 232)
5'-AGGAAATTCCCCTTCGCCCGTGTCAGTATAATTACCCGTTTATAGGGCGA
GTGTAGGCTGGAGCTGCTTC-3'.

The amplicon was subsequently inserted into MG1655, creating a C-terminal DnaK-mCer3 fusion. The cat cassette was subsequently flipped out by transiently equipping this strain with plasmid pCP20[7], resulting in the desired MG1655 dnaK-mCer3 strain.

24. Protein Purification from SDS Gel for MS Analysis

The purified inclusion bodies were loaded on SDS gel (4-15% Mini-PROTEAN® TGX™ Precast Protein Gels, 10-well, 50 µl) and stained by coomassie blue (R250). The excised bands were cut by a sterile scalpel under a laminar flow. The gel slices washed in several cycles by incubating them in 50 mM ammonium bicarbonate/ACN (acetonitrile) (1:1) for 10 min at room temperature until the blue stain is gone and replacing the buffer by 100% ACN and incubating for 5 min. After the last cycle, the samples were dried by speedvac and digested with 250 ng of modified trypsin (Promega) in 50 mM ammonium bicarbonate buffer (pH 8.3) overnight at 37° C. Peptides were extracted by adding 5% ACN+0.1% formic acid, and followed by 10% ACN+0.1% FA and 95% ACN in 0.5% FA) and dried by Speedvac. The extracted peptides were cleaned up by using pierce C18 spin Columns (Thermo Fisher Scientific) according to the manufacturer's instructions. The samples were diluted in 10 µL with 5% ACN+0.1% FA for injection in MS machine.

25. Statistics

Statistical calculations were performed using Prism unless otherwise indicated. For the ANOVA analysis of the infection model (FIG. 2F-1), the assumption that the groups have similar standard deviations was tested using Bartlett's test, which showed no significant differences between the standard deviations, except for the ureter data, which we ignored because it was caused by a reduction in the standard deviation of the untreated group.

TABLE 1

MIC and MBC values of selected peptides purified by HPLC-grade on E. coli O157.

| Purified Peptide | Sequences | MIC (µg/ml) | MBC (µg/ml) |
|---|---|---|---|
| P2 | RGLGLALVRRPRGLGLALVRR SEQ ID NO: 1 | 6 | 6 |
| P2 pro2 | RGLGPALPRRPRGLGPALPRR SEQ ID NO: 2 | >100 | >100 |
| P5 | RALLTTLLRRPRALLTTLLRR SEQ ID NO: 3 | 6 | 6 |
| P5R | RRALLTTLLRRPRALLTTLLRR SEQ ID NO: 4 | 12 | 12 |
| P105 | RALLRTLLRRPRALLTTLLRR SEQ ID NO: 5 | 12 | 12 |
| P14 | RGLLALLARRPRGLLALLARR SEQ ID NO: 6 | 6 | 6 |

MIC: Minimum inhibitory concentration
MBC: Minimum bactericidal concentration

TABLE 2

Activity profile of Colpeptin1 against various bacterial strains and sequence conservation of the HcaB protein and the target APR.

| strain | MIC (µg/mL) | Sequence ID APR | Sequence ID protein |
|---|---|---|---|
| Klebsiella pneumoniae (ATCC 1388) | 50 | 100 | 86 |
| Enterobacter cloacae LMG2783T | 50 | 57 | 29 |
| E coli ATCC 25922 | 12 | 0 | 0 |
| Proteus mirabilis | 50 | 43 | 27 |
| Acinetobacter radioresistens | 5 | 86 | 56 |
| Pseudomonas aeruginosa | 200 | 71 | 38 |
| Neisseria | 50 | 57 | 28 |
| Staphylococcus epidermidis 12228 | 50 | 42 | 27 |
| Staphylococcus aureus MRSA326 | 200 | 28 | 27 |
| Acinetobacter baumanii | 6 | 100 | 100 |
| E. coli O157 | 6 | 100 | 100 |

TABLE 3

Minimum Inhibitory Concentration of Colpeptin1 for chaperone deletion strains

| Strains | MIC (µg/mL) |
|---|---|
| KEIO WT | 12 |
| Δ Clp A | 12 |
| Δ Clp P | 12 |
| Δ Clp B | 12 |
| Δ Clp S | 12 |
| Δ Clp X | 12 |
| Δ Dan J | 12 |
| Δ Dan K | 6 |
| Δ htp G | 12 |
| Δ gro L | 12 |

TABLE 4

Peptide design and screening

| Name | Polypeptide | APR/ (SEQ ID NO) | TANGO score | Matches[1] | APR length | peptide sequence (SEQ ID NO) | CAMP[2] |
|---|---|---|---|---|---|---|---|
| P1 | EBESCP00000213293 | LLLSLLV (127) | 76.83 | 22 | 7 | RLLLSLLVRRPRLLLSLLVRR (SEQ ID NO: 7) | AMP |
| P2 | EBESCP00000210864 | GLGLALV (128) | 20.85 | 19 | 7 | RGLGLALVRRPRGLGLALVRR (SEQ ID NO: 1) | AMP |
| P3 | EBESCP00000209910 | LLLALLS (129) | 57.27 | 19 | 7 | RLLLALLSRRPRLLLALLSRR (SEQ ID NO: 8) | AMP |
| P4 | EBE5CP00000209975 | LALALLL (130) | 44 | 17 | 7 | RLALALLLRRPRLALALLLRR (SEQ ID NO: 9) | AMP |
| P5 | EBE5CP00000207772 | ALLTTLL (131) | 20.71 | 16 | 7 | RALLTTLLRRPRALLTTLLRR (SEQ ID NO: 3) | AMP |
| P6 | EBESCP00000212702 | TVTVTFG (132) | 32.55 | 16 | 7 | RTVTVTFGRRPRTVTVTFGRR (SEQ ID NO: 10) | NAMP |
| P7 | EBESCP00000212122 | TVTVTFG (133) | 32.7 | 16 | 7 | RTVTVTFGRRPRTVTVTFGRR (SEQ ID NO: 11) | NAMP |
| P8 | EBESCP00000209162 | IGALLLL (134) | 39.24 | 15 | 7 | RIGALLLLRRPRIGALLLLRR (SEQ ID NO: 12) | AMP |
| P9 | EBESCP00000212122 | TVTVTFN (135) | 32.28 | 15 | 7 | RTVTVTFNRRPRTVTVTFNRR (SEQ ID NO: 13) | NAMP |
| P10 | EBE5CP00000209965 | ALIAALQ (136) | 21.77 | 14 | 7 | RALIAALQRRPRALIAALQRR (SEQ ID NO: 14) | AMP |
| P11 | EBESCP00000211133 | VLALAAL (137) | 37.47 | 14 | 7 | RVLALAALRRPRVLALAALRR (SEQ ID NO: 15) | AMP |
| P12 | EBE5CP00000207824 | ALAVALL (138) | 72.72 | 13 | 7 | RALAVALLRRPRALAVALLRR (SEQ ID NO: 16) | AMP |
| P13 | EBESCP00000211390 | AVLGLLA (139) | 41.53 | 13 | 7 | RAVLGLLARRPRAVLGLLARR (SEQ ID NO: 17) | AMP |
| P14 | EBE5CP00000208655 | GLLALLA (140) | 33.3 | 13 | 7 | RGLLALLARRPRGLLALLARR (SEQ ID NO: 6) | AMP |
| P15 | EBESCP00000213158 | LIGIALG (141) | 33.04 | 13 | 7 | RLIGIALGRRPRLIGIALGRR (SEQ ID NO: 18) | AMP |
| P16 | EBESCP00000210379 | ALLTAVL (142) | 33.53 | 12 | 7 | RALLTAVLRRPRALLTAVLRR (SEQ ID NO: 19) | AMP |
| P17 | EBESCP00000210098 | QLVALLV (143) | 66.61 | 12 | 7 | RQLVALLVRRPRQLVALLVRR (SEQ ID NO: 20) | AMP |
| P18 | EBE5CP00000212988 | SAVLALL (144) | 43.39 | 12 | 7 | RSAVLALLRRPRSAVLALLRR (SEQ ID NO: 21) | AMP |
| P19 | EBE5CP00000212122 | VVTVTLN (145) | 50.97 | 12 | 7 | RVVTVTLNRRPRVVTVTLNRR (SEQ ID NO: 22) | NAMP |
| P20 | EBE5CP00000212555 | AVVLATG (146) | 24.03 | 11 | 7 | RAVVLATGRRPRAVVLATGRR (SEQ ID NO: 23) | AMP |
| P21 | EBE5CP00000209874 | LLLIVLG (147) | 81.63 | 11 | 7 | RLLLIVLGRRPRLLLIVLGRR (SEQ ID NO: 24) | AMP |
| P22 | EBESCP00000213098 | ALAVAIG (148) | 21.08 | 10 | 7 | RALAVAIGRRPRALAVAIGRR (SEQ ID NO: 25) | AMP |
| P23 | EBE5CP00000210425 | ALLITLL (149) | 74.9 | 10 | 7 | RALLITLLRRPRALLITLLRR (SEQ ID NO: 26) | AMP |
| P24 | EBE5CP00000212549 | GLLLALQ (150) | 30.59 | 10 | 7 | RGLLLALQRRPRGLLLALQRR (SEQ ID NO: 27) | AMP |
| P25 | EBESCP00000212702 | IVTVTLN (151) | 48.24 | 10 | 7 | RIVTVTLNRRPRIVTVTLNRR (SEQ ID NO: 28) | AMP |

TABLE 4-continued

Peptide design and screening

| Name | Polypeptide | APR/ (SEQ ID NO) | TANGO score | Matches[1] | APR length | peptide sequence (SEQ ID NO) | CAMP[2] |
|---|---|---|---|---|---|---|---|
| P26 | EBESCP00000211310 | LFVGLAL (152) | 39.45 | 10 | 7 | RLFVGLALRRPRLFVGLALRR (SEQ ID NO: 29) | AMP |
| P27 | EBESCP00000212038 | VLGLAAL (153) | 21.58 | 10 | 7 | RVLGLAALRRPRVLGLAALRR (SEQ ID NO: 30) | AMP |
| P28 | EBE5CP00000208389 | VVGLLAG (154) | 29.48 | 10 | 7 | RVVGLLAGRRPRVVGLLAGRR (SEQ ID NO: 31) | AMP |
| P29 | EBESCP00000211990 | ATVLALL (155) | 25.16 | 9 | 7 | RATVLALLRRPRATVLALLRR (SEQ ID NO: 32) | AMP |
| P30 | EBE5CP00000212858 | AVLVAIG (156) | 75.97 | 9 | 7 | RAVLVAIGRRPRAVLVAIGRR (SEQ ID NO: 33) | AMP |
| P31 | EBE5CP00000209426 | GLLVTLA (157) | 36.24 | 9 | 7 | RGLLVTLARRPRGLLVTLARR (SEQ ID NO: 34) | AMP |
| P32 | EBESCP00000209882 | LFVILAL (158) | 76.02 | 9 | 7 | RLFVILALRRPRLFVILALRR (SEQ ID NO: 35) | AMP |
| P33 | EBESCP00000211614 | LGIAVAL (159) | 20.13 | 9 | 7 | RLGIAVALRRPRLGIAVALRR (SEQ ID NO: 36) | AMP |
| P34 | EBESCP00000208407 | LLLLVNL (160) | 68.83 | 9 | 7 | RLLLLVNLRRPRLLLLVNLRR (SEQ ID NO: 37) | AMP |
| P35 | EBESCP00000212122 | TVTVALG (161) | 25.08 | 9 | 7 | RTVTVALGRRPRTVTVALGRR (SEQ ID NO: 38) | NAMP |
| P36 | EBESCP00000207816 | VGVIVGA (162) | 42.18 | 9 | 7 | RVGVIVGARRPRVGVIVGARR (SEQ ID NO: 39) | AMP |
| P37 | EBE5CP00000212873 | VVVAIAL (163) | 92.48 | 9 | 7 | RVVVAIALRRPRVVVAIALRR (SEQ ID NO: 40) | AMP |
| P38 | EBESCP00000212079 | AGLLSLV (164) | 24.67 | 8 | 7 | RAGLLSLVRRPRAGLLSLVRR (SEQ ID NO: 41) | AMP |
| P39 | EBESCP00000210861 | ALLIQLL (165) | 39.25 | 8 | 7 | RALLIQLLRRPRALLIQLLRR (SEQ ID NO: 42) | AMP |
| P40 | EBESCP00000212018 | AQVLALL (166) | 51.57 | 8 | 7 | RAQVLALLRRPRAQVLALLRR (SEQ ID NO: 43) | AMP |
| P41 | EBESCP00000209188 | AVVLAVN (167) | 72.36 | 8 | 7 | RAVVLAVNRRPRAVVLAVNRR (SEQ ID NO: 44) | AMP |
| P42 | EBESCP00000210332 | FVAGFIG (168) | 64.88 | 8 | 7 | RFVAGFIGRRPRFVAGFIGRR (SEQ ID NO: 45) | AMP |
| P43 | EBESCP00000210737 | LAIALAQ (169) | 25.46 | 8 | 7 | RLAIALAQRRPRLAIALAQRR (SEQ ID NO: 46) | AMP |
| P44 | EBESCP00000212024 | LFIIATA (170) | 66.7 | 8 | 7 | RLFIIATARRPRLFIIATARR (SEQ ID NO: 47) | AMP |
| P45 | EBESCP00000209032 | LIVAAIA (171) | 73.49 | 8 | 7 | RLIVAAIARRPRLIVAAIARR (SEQ ID NO: 48) | AMP |
| P46 | EBESCP00000211255 | LLAGIVA (172) | 34.55 | 8 | 7 | RLLAGIVARRPRLLAGIVARR (SEQ ID NO: 49) | AMP |
| P47 | EBESCP00000209206 | LLLAYLL (173) | 87.85 | 8 | 7 | RLLLAYLLRRPRLLLAYLLRR (SEQ ID NO: 50) | AMP |
| P48 | EBESCP00000208308 | LLLMLAG (174) | 50.96 | 8 | 7 | RLLLMLAGRRPRLLLMLAGRR (SEQ ID NO: 51) | AMP |
| P49 | EBE5CP00000212564 | LLTLLNL (175) | 20.02 | 8 | 7 | RLLTLLNLRRPRLLTLLNLRR (SEQ ID NO: 52) | AMP |

TABLE 4-continued

Peptide design and screening

| Name | Polypeptide | APR/ (SEQ ID NO) | TANGO score | Matches[1] | APR length | peptide sequence (SEQ ID NO) | CAMP[2] |
|---|---|---|---|---|---|---|---|
| P50 | EBESCP00000211085 | LVGLVLG (176) | 46.09 | 8 | 7 | RLVGLVLGRRPRLVGLV LGRR (SEQ ID NO: 53) | AMP |
| P51 | EBESCP00000210979 | LVVTAIA (177) | 55.99 | 8 | 7 | RLVVTAIARRPRLVVTAIA RR (SEQ ID NO: 54) | AMP |
| P52 | EBESCP00000207741 | PVIILTA (178) | 68.83 | 8 | 7 | RPVIILTARRPRPVIILTAR R (SEQ ID NO: 55) | AMP |
| P53 | EBESCP00000212005 | QAIVITG (179) | 30.47 | 8 | 7 | RQAIVITGRRPRQAIVITG RR (SEQ ID NO: 56) | AMP |
| P54 | EBESCP00000210487 | TVVLLAA (180) | 57.57 | 8 | 7 | RTVVLLAARRPRTVVLLA ARR (SEQ ID NO: 57) | AMP |
| P55 | EBE5CP00000209584 | AALITAL (181) | 23.95 | 7 | 7 | RAALITALRRPRAALITAL RR (SEQ ID NO: 58) | AMP |
| P56 | EBE5CP00000208677 | AALLAYV (182) | 59.49 | 7 | 7 | RAALLAYVRRPRAALLAY VRR (SEQ ID NO: 59) | AMP |
| P57 | EBESCP00000210682 | AITLVLT (183) | 42.08 | 7 | 7 | RAITLVLTRRPRAITLVLT RR (SEQ ID NO: 60) | AMP |
| P58 | EBESCP00000207808 | ALVSLLL (184) | 34.45 | 7 | 7 | RALVSLLLRRPRALVSLL LRR (SEQ ID NO: 61) | AMP |
| P59 | EBESCP00000211568 | GIVGLVG (185) | 43.59 | 7 | 7 | RGIVGLVGRRPRGIVGLV GRR (SEQ ID NO: 62) | AMP |
| P60 | EBESCP00000213181 | GLAVGVI (186) | 49.09 | 7 | 7 | RGLAVGVIRRPRGLAVG VIRR (SEQ ID NO: 63) | AMP |
| P61 | EBESCP00000208911 | GTVLLVS (187) | 52.8 | 7 | 7 | RGTVLLVSRRPRGTVLL VSRR (SEQ ID NO: 64) | AMP |
| P62 | EBESCP00000210871 | GVALVVA (188) | 77.53 | 7 | 7 | RGVALVVARRPRGVALV VARR (SEQ ID NO: 65) | AMP |
| P63 | EBESCP00000212804 | GVLAVFA (189) | 78.55 | 7 | 7 | RGVLAVFARRPRGVLAV FARR (SEQ ID NO: 66) | AMP |
| P64 | EBESCP00000208059 | ILLLTLV (190) | 98.77 | 7 | 7 | RILLLTLVRRPRILLLTLV RR (SEQ ID NO: 67) | AMP |
| P65 | EBESCP00000210221 | IVIVGGG (191) | 27.51 | 7 | 7 | RIVIVGGGRRPRIVIVGG GRR (SEQ ID NO: 68) | AMP |
| P66 | EBESCP00000211867 | LCLLLAL (192) | 39.47 | 7 | 7 | RLCLLLALRRPRLCLLLA LRR (SEQ ID NO: 68) | AMP |
| P67 | EBESCP00000209059 | LLAILAS (193) | 42.95 | 7 | 7 | RLLAILASRRPRLLAILAS RR (SEQ ID NO: 69) | AMP |
| P68 | EBESCP00000211824 | LLIAVGA (194) | 54.41 | 7 | 7 | RLLIAVGARRPRLLIAVG ARR (SEQ ID NO: 70) | AMP |
| P69 | EBE5CP00000210873 | LLIVLGA (195) | 75.39 | 7 | 7 | RLLIVLGARRPRLLIVLGA RR (SEQ ID NO: 71) | AMP |
| P70 | EBE5CP00000211959 | NVVLLAL (196) | 68.93 | 7 | 7 | RNVVLLALRRPRNVVLLA LRR (SEQ ID NO: 72) | AMP |
| P71 | EBE5CP00000210460 | PAIVAAV (197) | 33.39 | 7 | 7 | RPAIVAAVRRPRPAIVAA VRR (SEQ ID NO: 73) | AMP |
| P72 | EBESCP00000211391 | QLLLTLL (198) | 73.1 | 7 | 7 | RQLLLTLLRRPRQLLLTL LRR (SEQ ID NO: 74) | AMP |
| P73 | EBE5CP00000209484 | SAIIGII (199) | 60.99 | 7 | 7 | RSAIIGIIRRPRSAIIGIIRR (SEQ ID NO: 75) | AMP |
| P74 | EBESCP00000212211 | VSLVAIL (200) | 57.68 | 7 | 7 | RVSLVAILRRPRVSLVAIL RR (SEQ ID NO: 76) | AMP |

TABLE 4-continued

Peptide design and screening

| Name | Polypeptide | APR/ (SEQ ID NO) | TANGO score | Matches[1] | APR length | peptide sequence (SEQ ID NO) | CAMP[2] |
|---|---|---|---|---|---|---|---|
| P75 | EBE5CP00000209467 | VVALVAG (201) | 60.61 | 7 | 7 | RVVALVAGRRPRVVALV AGRR (SEQ ID NO: 77) | AMP |
| P76 | same as P1 | | | | 7 | RLRLSLLVRRPRLLLSLL VRR (SEQ ID NO: 78) | AMP |
| P77 | same as P2 | | | | 7 | RGLRLALVRRPRGLGLA LVRR (SEQ ID NO: 79) | AMP |
| P78 | same as P3 | | | | 7 | RLLLARLSRRPRLLLALL SRR (SEQ ID NO: 80) | AMP |
| P79 | same as P4 | | | | 7 | RLALRLLLRRPRLALALL LRR (SEQ ID NO: 81) | AMP |
| P80 | same as P5 | | | | 7 | RALRTTLLRRPRALLTTL LRR (SEQ ID NO: 82) | AMP |
| P81 | same as P6 | | | | 7 | RTVTRTFGRRPRTVTVT FGRR (SEQ ID NO: 83) | NAMP |
| P82 | same as P7 | | | | 7 | RTVTVRFGRRPRTVTVT FGRR (SEQ ID NO: 84) | NAMP |
| P83 | same as P8 | | | | 7 | RIRALLLLRRPRIGALLLL RR (SEQ ID NO: 85) | AMP |
| P84 | same as P9 | | | | 7 | RTVTVTRNRRPRTVTVT FNRR (SEQ ID NO: 86) | NAMP |
| P85 | same as P10 | | | | 7 | RALRAALQRRPRALIAAL QRR (SEQ ID NO: 87) | AMP |
| P86 | same as P11 | | | | 7 | RVLARAALRRPRVLALA ALRR (SEQ ID NO: 88) | AMP |
| P87 | same as P12 | | | | 7 | RALRVALLRRPRALAVAL LRR (SEQ ID NO: 89) | AMP |
| P88 | same as P13 | | | | 7 | RAVRGLLARRPRAVLGL LARR (SEQ ID NO: 90) | AMP |
| P89 | same as P14 | | | | 7 | RGLLARLARRPRGLLALL ARR (SEQ ID NO: 91) | AMP |
| P90 | same as P15 | | | | 7 | RLRGIALGRRPRLIGIALG RR (SEQ ID NO: 92) | AMP |
| P91 | same as P16 | | | | 7 | RALLTARLRRPRALLTAV LRR (SEQ ID NO: 93) | AMP |
| P92 | same as P17 | | | | 7 | RQLVARLVRRPRQLVAL LVRR (SEQ ID NO: 94) | AMP |
| P93 | same as P18 | | | | 7 | RSARLALLRRPRSAVLAL LRR (SEQ ID NO: 95) | AMP |
| P94 | same as P19 | | | | 7 | RVVTVRLNRRPRVVTVT LNRR (SEQ ID NO: 96) | AMP |
| P95 | same as P20 | | | | 7 | RAVRLATGRRPRAVVLA TGRR (SEQ ID NO: 97) | AMP |
| P96 | same as P21 | | | | 7 | RLRLIVLGRRPRLLLIVLG RR (SEQ ID NO: 98) | AMP |
| P97 | same as P22 | | | | 7 | RARAVAIGRRPRALAVAI GRR (SEQ ID NO: 99) | AMP |
| P98 | same as P23 | | | | 7 | RARLITLLRRPRALLITLL RR (SEQ ID NO: 100) | AMP |

TABLE 4-continued

Peptide design and screening

| Name | Polypeptide | APR/ (SEQ ID NO) | TANGO score | Matches[1] | APR length | peptide sequence (SEQ ID NO) | CAMP[2] |
|---|---|---|---|---|---|---|---|
| P99 | same as P24 | | | | 7 | RGLRLALQRRPRGLLLALQRR (SEQ ID NO: 101) | AMP |
| P100 | same as P25 | | | | 7 | RIVRVTLNRRPRIVTVTLNRR (SEQ ID NO: 102) | AMP |
| P101 | same as P1 | | | | 7 | RLLRSLLVRRPRLLLSLLVRR (SEQ ID NO: 103) | AMP |
| P102 | same as P2 | | | | 7 | RGLGRALVRRPRGLGLALVRR (SEQ ID NO: 104) | AMP |
| P103 | same as P3 | | | | 7 | RLLLALRSRRPRLLLALLSRR (SEQ ID NO: 105) | AMP |
| P104 | same as P4 | | | | 7 | RLALARLLRRPRLALALLLRR (SEQ ID NO: 106) | AMP |
| P105 | same as P5 | | | | 7 | RALLRTLLRRPRALLTTLLRR (SEQ ID NO: 5) | AMP |
| P106 | same as P6 | | | | 7 | RTVTVRFGRRPRTVTVTFGRR (SEQ ID NO: 107) | NAMP |
| P107 | same as P7 | | | | 7 | RTVTVTRGRRPRTVTVTFGRR (SEQ ID NO: 108) | NAMP |
| P108 | same as P8 | | | | 7 | RIGRLLLLRRPRIGALLLLRR (SEQ ID NO: 109) | AMP |
| P109 | same as P9 | | | | 7 | RTVTVTFRRRPRTVTVTFNRR (SEQ ID NO: 110) | NAMP |
| P110 | same as P10 | | | | 7 | RALIRALQRRPRALIAALQRR (SEQ ID NO: 111) | AMP |
| P111 | same as P11 | | | | 7 | RVLALRALRRPRVLALAALRR (SEQ ID NO: 112) | AMP |
| P112 | same as P12 | | | | 7 | RALARALLRRPRALAVALLRR (SEQ ID NO: 113) | AMP |
| P113 | same as P13 | | | | 7 | RAVLRLLARRPRAVLGLLARR (SEQ ID NO: 114) | AMP |
| P114 | same as P14 | | | | 7 | RGLLALRARRPRGLLALLARR (SEQ ID NO: 115) | AMP |
| P115 | same as P15 | | | | 7 | RLIRIALGRRPRLIGIALGRR (SEQ ID NO: 116) | AMP |
| P116 | same as P16 | | | | 7 | RALLTAVRRRPRALLTAVLRR (SEQ ID NO: 117) | AMP |
| P117 | same as P17 | | | | 7 | RQLVALRVRRPRQLVALLVRR (SEQ ID NO: 118) | AMP |
| P118 | same as P18 | | | | 7 | RSAVRALLRRPRSAVLALLRR (SEQ ID NO: 119) | AMP |
| P119 | same as P19 | | | | 7 | RVVIVTIRNRRPRVVIVTLNRR (SEQ ID NO: 120) | NAMP |
| P120 | same as P20 | | | | 7 | RAVVRATGRRPRAVVLATGRR (SEQ ID NO: 121) | AMP |
| P121 | same as P21 | | | | 7 | RLLRIVLGRRPRLLLIVLGRR (SEQ ID NO: 122) | AMP |
| P122 | same as P22 | | | | 7 | RALRVAIGRRPRALAVAIGRR (SEQ ID NO: 123) | AMP |

TABLE 4-continued

Peptide design and screening

| Name | Polypeptide | APR/ (SEQ ID NO) | TANGO score | Matches[1] | APR length | peptide sequence (SEQ ID NO) | CAMP[2] |
|---|---|---|---|---|---|---|---|
| P123 | same as P23 | | | | 7 | RALRITLLRRPRALLITLLRR (SEQ ID NO: 124) | AMP |
| P124 | same as P24 | | | | 7 | RGLLRALQRRPRGLLLALQRR (SEQ ID NO: 125) | AMP |
| P125 | same as P25 | | | | 7 | RIVTRTLNRRPRIVTVTLNRR (SEQ ID NO: 126) | AMP |

[1]The number of matching sequences in the *E. coli* O157:H7 proteome, allowing 1 mutation.
[2]Prediction of the antibacterial activity using the CAMP software8

TABLE 5

Active peptides against *E. coli* O157 under 25 ug/ml.

| Number | Name | *E. coli* O157(ug/ml) |
|---|---|---|
| 1 | P2 | 6 |
| 2 | P3 | 12 |
| 3 | P4 | 6 |
| 4 | P5 | 12 |
| 5 | P12 | 25 |
| 6 | P14 | 12 |
| 7 | P16 | 25 |
| 8 | P18 | 12 |
| 9 | P23 | 25 |
| 10 | P26 | 25 |
| 11 | P29 | 25 |
| 12 | P33 | 25 |
| 13 | P39 | 25 |
| 14 | P40 | 25 |
| 15 | P49 | 12 |
| 16 | P50 | 6 |
| 17 | P58 | 12 |
| 18 | P72 | 25 |
| 19 | P76 | 12 |
| 20 | P79 | 12 |
| 21 | P80 | 25 |
| 22 | P87 | 25 |
| 23 | P88 | 25 |
| 24 | P89 | 12 |
| 25 | P90 | 25 |
| 26 | P91 | 25 |
| 27 | P92 | 6 |
| 28 | P93 | 25 |
| 29 | P99 | 25 |
| 30 | P101 | 12 |
| 31 | P103 | 25 |
| 32 | P105 | 6 |
| 33 | P111 | 25 |
| 34 | P112 | 25 |
| 35 | P113 | 25 |
| 36 | P114 | 25 |
| 37 | P115 | 25 |
| 38 | P116 | 6 |
| 39 | P117 | 25 |
| 40 | P118 | 25 |
| 41 | P123 | 25 |
| 42 | P124 | 12 |
| 43 | P125 | 25 |

TABLE 6

Organs weights of mice treated with 30 mg/kg Colpeptin1 after 18 consecutive days injection.

| | Organs weights (gr) | |
|---|---|---|
| | Control | Colpeptin 1 |
| Heart | 0.20 ± 0.01 | 0.20 ± 0.02 |
| Kidneys | 0.58 ± 0.01 | 0.58 ± 0.01 |
| Spleen | 0.12 ± 0.01 | 0.12 ± 0.01 |
| Liver | 1.75 ± 0.11 | 1.90 ± 0.11 |
| Brain | 0.60 ± 0.03 | 0.56 ± 0.02 |

TABLE 7

Hematological values (mean + SD) of mice treated by Colpeptin 1 after 18 consecutive days of injection.

| Hematological Parameters | Control Mean ± SD | Colpeptin1 Mean ± SD |
|---|---|---|
| WBC | 5.63 ± 0.16 | 6.89 ± 0.42 |
| NEU | 0.491 ± 0.03 | 0.80 ± 0.06 |
| LYM | 4.70 ± 0.02 | 5.32 ± 0.52 |
| MONO | 0.099 ± 0.04 | 0.15 ± 0.05 |
| EOS | 0.058 ± 0.01 | 0.14 ± 0.06 |
| BASO | 0.270 ± 0.02 | 0.24 ± 0.02 |
| RBC | 10.02 ± 024 | 10.9 ± 0.46 |
| HGB | 19.60 ± 0.20 | 17.8 ± 0.45 |
| HCT | 99.43 ± 2.06 | 98.87 ± 3.7 |
| MCV | 280.4 ± 1.06 | 273 ± 1.32 |
| MCH | 49.3 ± 1.090 | 48.2 ± 0.34 |
| MCHC | 51.89 ± 0.70 | 53.7 ± 0.42 |
| PLT | 1997 ± 30.7 | 1595 ± 50.7 |
| MPV | 17.65 ± 0.09 | 16.36 ± 0.2 |
| PCT | 1.150 ± 0.06 | 0.88 ± 0.05 |
| PDW | 49.3 ± 0.11 | 49.9 ± 0.43 |

WBC, White Blood Cell or Leukocyte count. NEU, Neutrophil absolute count % N—Neutrophil percent. LYM, Lymphocyte absolute count % L—Lymphocyte percent. MONO, Monocyte absolute count % M—Monocyte percent. EOS, Eosinophil absolute count % E—Eosinophil percent. BASO, Basophil absolute count % B—Basophil percent. RBC, Red Blood Cell or Erythrocyte count. HGB, Hemoglobin concentration. HCT, Hematocrit. MCV, Mean Corpuscular Volume. MCH, Mean Corpuscular Hemoglobin. MCHC, Mean Corpuscular Hemoglobin Concentration. PLT, Platelet or Thrombocyte count. MPV, Mean Platelet Volume. PDW, Platelet Distribution Width. PCT, Plateletcrit.

WBC, White Blood Cell or Leukocyte count. NEU, Neutrophil absolute count % N—Neutrophil percent .LYM, Lymphocyte absolute count % L—Lymphocyte percent. MONO, Monocyte absolute count % M—Monocyte percent. EOS, Eosinophil absolute count % E—Eosinophil percent. BASO, Basophil absolute count % B—Basophil percent. RBC, Red Blood Cell or Erythrocyte count. HGB, Hemoglobin concentration. HCT, Hematocrit. MCV, Mean Corpuscular Volume. MCH, Mean Corpuscular Hemoglobin. MCHC, Mean Corpuscular Hemoglobin Concentration. PLT, Platelet or Thrombocyte count. MPV, Mean Platelet Volume. PDW, Platelet Distribution Width. PCT, Plateletcrit.

TABLE 8

Proteins from the *E coli* proteome with a sequence segment similar (identical, or 1 mismatch (85.71% identity)) to the APR of Colpeptin1.

| APR/ (SEQ ID NO) | % Sequence ID | Gene | UniProt | Protein Name | PaxDB abundance (ppm) | Solubility (%) |
|---|---|---|---|---|---|---|
| GLGLALV (128) | 100 | hcaB | HCAB_ECOLI | 3-phenylpropionate-dihydrodiol/cinnamic acid-dihydrodiol dehydrogenase | 0.015 | 10 |
| GLGLALA (202) | 85.71 | skp | SKP_ECOLI | Chaperone protein skp | 796 | 49 |
| GLGLAIV (203) | 85.71 | phoR | PHOR_ECOLI | Phosphate regulon sensor protein PhoR | 13.3 | 13 |
| GLGLAMV (204) | 85.71 | dtpA | DTPA_ECOLI | Dipeptide and tripeptide permease A | 8.42 | NA |
| GLGLSLV (205) | 85.71 | yedV | YEDV_ECOLI | Probable sensor-like histidine kinase YedV | 3.44 | 13 |
| GLALALV (206) | 85.71 | yjcE | YJCE_ECOLI | Uncharacterized Na(+)/H(+) exchanger YjcE | 2.04 | NA |
| GLGLAIV (203) | 85.71 | envZ | ENVZ_ECOLI | Osmolarity sensor protein EnvZ | 1.99 | NA |
| GLGLAIV (203) | 85.71 | rstB | RSTB_ECOLI | Sensor protein RstB | 1.25 | 54 |
| GLGLAVV (207) | 85.71 | zraS | ZRAS_ECOLI | Sensor protein ZraS | 0.816 | NA |
| GLPLALV (208) | 85.71 | ybfO | YBFO_ECOLI | Putative uncharacterized protein YbfO | 0.48 | 8 |
| GVGLALV (209) | 85.71 | dcuS | DCUS_ECOLI | Sensor histidine kinase DcuS | 0.185 | 35 |
| GLGLALS (210) | 85.71 | atoS | ATOS_ECOLI | Signal transduction histidine-protein kinase AtoS | 0.153 | 27 |
| GLLLALV (211) | 85.71 | hycD | HYCD_ECOLI | Formate hydrogenlyase subunit 4 | 0.01 | NA |
| GLLLALV (211) | 85.71 | yddG | YDDG_ECOLI | Aromatic amino acid exporter YddG | 0.01 | NA |
| GLGLALQ (212) | 85.71 | yfeJ | YFCJ_ECOLI | UPF0226 protein YfcJ | 0.01 | NA |
| GIGLALV (213) | 85.71 | yfeZ | YFEZ_ECOLI | Inner membrane protein yfeZ | 0.01 | 41 |
| GLGLAIV (203) | 85.71 | cpxA | CPXA_ECOLI | Sensor protein CpxA | | |
| GLGLAFV (214) | 85.71 | creC | CREC_ECOLI | Sensor protein CreC | | |
| GLSLALV (215) | 85.71 | yqhA | YQHA_ECOLI | UPF0114 protein YqhA | | |

TABLE 9

Proteins from the *Acinetobacter* proteome with a sequence segment similar (identical, or 1 mismatch (85.71% identity)) to the APR Colpeptin1.

| % Sequence ID | target | APR/ (SEQ ID NO) |
|---|---|---|
| 100 | tr\|A0A0M3FL55\|A0A0M3FL55_ACIBA 2,3-dihydroxy-2,3-dihydrophenylpropionate dehydrogenase OS = *Acinetobacter baumannii* GN = APC61_00140 PE = 4 SV = 1 | GLGLALV (128) |
| 85.71 | tr\|A0A154DMZ0\|A0A154DMZ0_ACIBA Peptidase inhibitor 178 family protein OS = *Acinetobacter baumannii* GN = LV37_00119 PE = 4 SV = 1 | FLGLALV (216) |
| 85.71 | tr\|A0A154FG10\|A0A154FG10_ACIBA Styrene monooxygenase StyA OS = *Acinetobacter baumannii* GN = styA PE = 4 SV = 1 | GIGLALV (213) |
| 85.71 | tr\|A0A15400C4\|A0A15400C4_ACIBA Inner membrane transport protein YdhP OS = *Acinetobacter baumannii* GN = ydhP_2 PE = 4 PV = 1 | GLGLLLV (217) |
| 85.71 | tr\|A0A0C4Y9D8\|A0A0C4Y9D8_ACIBA Uncharacterized protein OS = *Acinetobacter baumannii* GN = NG19_0091 PE = 4 SV = 1 | GLGLANV (218) |
| 85.71 | tr\|V5V981\|V5V981_ACIBA HAMP domain protein OS = *Acinetobacter baumannii* GN = envZ PE = 4 PV = 1 | GLGLAIV (203) |
| 85.71 | tr\|A0A059ZK79\|A0A059ZK79_ACIBA Histidine kinase OS = *Acinetobacter baumannii* GN = AB988_1084 PE = 4 SV = 1 | GLGLAIV (203) |
| 85.71 | tr\|A0A0H4UH22\|A0A0H4UH22_ACIBA Histidine kinase OS = *Acinetobacter baumannii* GN = ACX61_00500 PE = 4 SV = 1 | GLGLAIV (203) |
| 85.71 | tr\|A0A0E1F1S4\|A0A0E1FIS4_ACIBA Restriction endonuclease subunit R OS = *Acinetobacter baumannii* GN = IX87_01010 PE = 4 SV = 1 | GLPLALV (208) |
| 85.71 | tr\|V5VG19\|V5VG19_ACIBA NADH dehydrogenase 1 chain M membrane subunit OS = *Acinetobacter baumannii* GN = nouM PE = 4 SV = 1 | GLGLALW (219) |
| 85.71 | tr\|A0A0R0R589\|A0A0R0R589_ACIBA Aminio acid ABC transporter substrate binding protein OS = *Acinetobacter baumannii* GN = APB90_07745 PE = 4 PV = 1 | GLGLALL (220) |
| 85.71 | tr\|A0A0Q1\|X94\|A0A0Q1\|X94_ACIBA Histidine kinase OS = *Acinetobacter baumannii* GN = APD31_17375 PE = 4 SV = 1 | GLGLAVV (207) |
| 85.71 | tr\|A0A0B2XQZ1\|A0A0B2XQZ1_ACIBA Hemolysin OS = *Acinetobacter baumannii* GN = NT90_18235 PE = 4 SV = 1 | FLGLALV (216) |
| 85.71 | tr\|A0A0N8Z036\|A0A0N8Z036_ACIBA AraC family transcriptional regulator OS = *Acinetobacter baumannii* GN = APB90_07655 PE = 4 SV = 1 | DLGLALV (221) |
| 85.71 | tr\|A0A0VV3DY21\|A0A0VV3DY21_ACIBA Histidine kinase OS = *Acinetobacter baumannii* GN = AL489_08625 PE = 4 SV = 1 | GLGLALS (210) |
| 85.71 | tr\|A0A0R0S9N3\|A0A0R0S9N3_ACIBA Histidine kinase OS = *Acinetobacter baumannii* GN = APC61_19600 PE = 4 SV = 1 | GLGLAVV (207) |
| 85.71 | tr\|A0A0H4UPE2\|A0A0H4UPE2_ACIBA Histidine kinase OS = *Acinetobacter baumannii* GN = ACX61_09245 PE = 4 SV = 1 | GLGLAVV (207) |
| 85.71 | tr\|A0A0VV3DVP5\|A0A0VV3DVP5_ACIBA Histidine kinase OS = *Acinetobacter baumannii* GN = AL489_14670 PE = 4 SV = 1 | GLGLAVV (207) |
| 85.71 | tr\|A0A0VV3DX13\|A0A0VV3DX13_ACIBA Adenosylmethionine-8-amino-7-oxononanoate aminotransferase OS = *Acinetobacter baumannii* GN = AL489_17500 PE = 3 SV = 1 | GLGLALR (222) |

REFERENCES

1 Balch, W. E., Morimoto, R. I., Dillin, A. & Kelly, J. W. Adapting proteostasis for disease intervention. *Science* 319, 916-919, doi:319/5865/916 [pii]10.1126/science.1141448 (2008).
2 Ellis, R. J. Macromolecular crowding: obvious but underappreciated. *Trends Biochem Sci* 26, 597-604. (2001).
3 Young, J. C., Agashe, V. R., Siegers, K. & Hartl, F. U. Pathways of chaperone-mediated protein folding in the cytosol. *Nat Rev Mol Cell Biol* 5, 781-791, doi:10.1038/nrm1492 (2004).
4 Mogk, A., Huber, D. & Bukau, B. Integrating protein homeostasis strategies in prokaryotes. *Cold Spring Harbor perspectives in biology* 3, doi:10.1101/cshperspect.a004366 (2011).
5 Dobson, C. M. Protein folding and misfolding. *Nature* 426, 884-890 (2003).
6 Krebs, M. R., Morozova-Roche, L. A., Daniel, K., Robinson, C. V. & Dobson, C. M. Observation of sequence specificity in the seeding of protein amyloid fibrils. *Protein Sci* 13, 1933-1938, doi:10.1110/ps.04707004 13/7/1933 [pii] (2004).
7 O'Nuallain, B., Williams, A. D., Westermark, P. & Wetzel, R. Seeding specificity in amyloid growth induced by heterologous fibrils. *J Biol Chem* 279, 17490-17499 (2004).
8 Ganesan, A. et al. Selectivity of aggregation-determining interactions. *J Mol Biol* 427, 236-247, doi:10.1016/j.jmb.2014.09.027 (2015).
9 De Baets, G., Schymkowitz, J. & Rousseau, F. Predicting aggregation-prone sequences in proteins. *Essays Biochem* 56, 41-52, doi:10.1042/bse0560041 (2014).
10 Ganesan, A. et al. Structural hot spots for the solubility of globular proteins. *Nature communications* 7, 10816, doi:10.1038/ncomms10816 (2016).
11 Willmund, F. et al. The cotranslational function of ribosome-associated Hsp70 in eukaryotic protein homeostasis. *Cell* 152, 196-209, doi:10.1016/j.cell.2012.12.001 (2013).
12 Linding, R., Schymkowitz, J., Rousseau, F., Diella, F. & Serrano, L. A comparative study of the relationship between protein structure and beta-aggregation in globular and intrinsically disordered proteins. *J Mol Biol* 342, 345-353, doi:10.1016/j.jmb.2004.06.088 (2004).
13 Tompa, P. Intrinsically unstructured proteins. *Trends Biochem Sci* 27, 527-533 (2002).
14 Rousseau, F., Serrano, L. & Schymkowitz, J. W. How evolutionary pressure against protein aggregation shaped chaperone specificity. *J Mol Biol* 355, 1037-1047, doi:10.1 016/j.jmb.2005.11.035 (2006).
15 Bednarska, N. G., Schymkowitz, J., Rousseau, F. & Van Eldere, J. Protein aggregation in bacteria: the thin boundary between functionality and toxicity. *Microbiol-Sgm* 159, 1795-1806, doi:10.1099/mic.0.069575-0 (2013).
16 Seefeldt, A. C. et al. The proline-rich antimicrobial peptide Onc112 inhibits translation by blocking and destabilizing the initiation complex. *Nat Struct Mol Biol* 22, 470-475, doi:10.1038/nsmb.3034 (2015).
17 Last, N. B., Schlamadinger, D. E. & Miranker, A. D. A common landscape for membrane-active peptides. *Protein Sci* 22, 870-882, doi:10.1002/pro.2274 (2013).
18 Last, N. B. & Miranker, A. D. Common mechanism unites membrane poration by amyloid and antimicrobial peptides. *Proc Natl Acad Sci USA* 110, 6382-6387, doi:10.1073/pnas.1219059110 (2013).
19 Bednarska, N. G. et al. Protein aggregation as an antibiotic design strategy. *Mol Microbiol*, doi:10.1111/mmi.13269 (2015).
20 Hayashi, T. et al. Complete genome sequence of enterohemorrhagic *Escherichia coli* O157:H7 and genomic comparison with a laboratory strain K-12. *DNA Res* 8, 11-22 (2001).
21 Betti, C. et al. Sequence-Specific Protein Aggregation Generates Defined Protein Knockdowns in Plants. *Plant physiology* 171, 773-787, doi:10.1104/pp. 16.00335 (2016).
22 De Baets, G., Van Durme, J., Rousseau, F. & Schymkowitz, J. A genome-wide sequence-structure analysis suggests aggregation gatekeepers constitute an evolutionary constrained functional class. *J Mol Biol* 426, 2405-2412, doi:10.1016/j.jmb.2014.04.007 (2014).
23 Beerten, J. et al. Aggregation gatekeepers modulate protein homeostasis of aggregating sequences and affect bacterial fitness. *Protein Eng Des Sel* 25, 357-366, doi:10.1093/protein/gzs031 (2012).
24 Rousseau, F., Serrano, L. & Schymkowitz, J. W. H. How evolutionary pressure against protein aggregation shaped chaperone specificity. *Journal of Molecular Biology* 355, 1037-1047, doi:10.1016/j.jmb.2005.11.035 (2006).
25 Hancock, R. E. & Chapple, D. S. Peptide antibiotics. *Antimicrobial agents and chemotherapy* 43, 1317-1323 (1999).
26 Waghu, F. H. et al. CAMP: Collection of sequences and structures of antimicrobial peptides. *Nucleic Acids Res* 42, D1154-1158, doi:10.1093/nar/gktl 157 (2014).
27 Rokney, A. et al. *E. coli* transports aggregated proteins to the poles by a specific and energy-dependent process. *J Mol Biol* 392, 589-601, doi:10.1016/j.jmb.2009.07.009 (2009).
28 Young, L. M. et al. Screening and classifying smallmolecule inhibitors of amyloid formation using ion mobility spectrometry-mass spectrometry. *Nat Chem* 7, 73-81, doi:10.1038/nchem.2129 (2015).
29 Klingstedt, T. et al. Synthesis of a library of oligothiophenes and their utilization as fluorescent ligands for spectral assignment of protein aggregates. *Organic & biomolecular chemistry* 9, 8356-8370, doi:10.1039/c1ob05637a (2011).
30 Hammarstrom, P. et al. A fluorescent pentameric thiophene derivative detects in vitro-formed prefibrillar protein aggregates. *Biochemistry* 49, 6838-6845, doi:10.1021/bi100922r (2010).
31 Aslund, A. et al. Novel pentameric thiophene derivatives for in vitro and in vivo optical imaging of a plethora of protein aggregates in cerebral amyloidoses. *ACS chemical biology* 4, 673-684, doi:10.1021/cb900112v (2009).
32 Cremers, C. M. et al. Polyphosphate: A Conserved Modifier of Amyloidogenic Processes. *Mol Cell* 63, 768-780, doi:10.1016/j.molcel.2016.07.016 (2016).
33 Wang, M. et al. PaxDb, a database of protein abundance averages across all three domains of life. *Mol Cell Proteomics* 11, 492-500, doi:10.1074/mcp.0111.014704 (2012).
34 Niwa, T. et al. Bimodal protein solubility distribution revealed by an aggregation analysis of the entire ensemble of *Escherichia coli* proteins. *Proceedings of the National Academy of Sciences of the United States of America* 106, 4201-4206, doi:10.1073/pnas.0811922106 (2009).
35 Dana, A. & Tuller, T. Mean of the typical decoding rates: a new translation efficiency index based on the analysis of ribosome profiling data. *G3 (Bethesda)* 5, 73-80, doi:10.1534/g3.114.015099 (2014).

36 Huang da, W., Sherman, B. T. & Lempicki, R. A. Systematic and integrative analysis of large gene lists using DAVID bioinformatics resources. *Nat Protoc* 4, 44-57, doi:10.1038/nprot.2008.211 (2009).
37 Baba, T. et al. Construction of *Escherichia coli* K-12 in-frame, single-gene knockout mutants: the Keio collection. *Mol Syst Biol* 2, 2006 0008, doi:10.1038/msb4100050 (2006).
38 Xu, J. et al. Gain of function of mutant p53 by coaggregation with multiple tumor suppressors. *Nat Chem Biol* 7, 285-295, doi:10.1038/nchembio.546 (2011).
39 Calloni, G. et al. DnaK functions as a central hub in the *E. coli* chaperone network. *Cell reports* 1, 251-264, doi:10.1016/j.celrep.2011.12.007 (2012).
40 Chapman, E. et al. Global aggregation of newly translated proteins in an *Escherichia coli* strain deficient of the chaperonin GroEL. *Proc Natl Acad Sci* USA 103, 15800-15805, doi:10.1073/pnas.0607534103 (2006).
41 Fujiwara, K., Ishihama, Y., Nakahigashi, K., Soga, T. & Taguchi, H. A systematic survey of in vivo obligate chaperonin-dependent substrates. *EMBO J* 29, 1552-1564, doi:10.1038/emboj.2010.52 (2010).
42 Houry, W. A., Frishman, D., Eckerskorn, C., Lottspeich, F. & Hartd, F. U. Identification of in vivo substrates of the chaperonin GroEL. *Nature* 402, 147-154 (1999).
43 Kerner, M. J. et al. Proteome-wide analysis of chaperonin-dependent protein folding in *Escherichia coli*. *Cell* 122, 209-220, doi:10.1016/j.cell.2005.05.028 (2005).
44 Niwa, T., Kanamori, T., Ueda, T. & Taguchi, H. Global analysis of chaperone effects using a reconstituted cell-free translation system. *Proc Natl Acad Sci USA* 109, 8937-8942, doi:10.1073/pnas.1201380109 (2012).
45 Mogk, A. et al. Identification of thermolabile *Escherichia coli* proteins: prevention and reversion of aggregation by DnaK and ClpB. *Embo J* 18, 6934-6949 (1999).
46 Deuerling, E. et al. Trigger Factor and DnaK possess overlapping substrate pools and binding specificities. *Mol Microbiol* 47, 1317-1328 (2003).
47 Gallardo, R. et al. De novo design of a biologically active amyloid. *Science* 354, doi:10.1 126/science.aah4949 (2016).

The invention claimed is:

1. A non-naturally occurring anti-bacterial peptide configured to induce aggregation of one or more primary target proteins of a bacterium so as to form inclusion bodies comprising said one or more primary target proteins in said bacterium, wherein the peptide has an amino acid sequence selected from P2 (SEQ ID NO: 1), P3 (SEQ ID NO: 8), P4 (SEQ ID NO: 9), P5 (SEQ ID NO: 3), P12 (SEQ ID NO: 16), P14 (SEQ ID NO: 6), P16 (SEQ ID NO: 19), P18 (SEQ ID NO: 21), P23 (SEQ ID NO: 26), P26 (SEQ ID NO: 29), P29 (SEQ ID NO: 32), P33 (SEQ ID NO: 36), P39 (SEQ ID NO: 42), P40 (SEQ ID NO: 43), P49 (SEQ ID NO: 52), P50 (SEQ ID NO: 53), P58 (SEQ ID NO: 61), P72 (SEQ ID NO: 74), P76 (SEQ ID NO: 78), P79 (SEQ ID NO: 81), P80 (SEQ ID NO: 82), P87 (SEQ ID NO: 89), P88 (SEQ ID NO: 90), P89 (SEQ ID NO: 91), P90 (SEQ ID NO: 92), P91 (SEQ ID NO: 93), P92 (SEQ ID NO: 94), P93 (SEQ ID NO: 95), P99 (SEQ ID NO: 101), P101 (SEQ ID NO: 103), P103 (SEQ ID NO: 105), P105 (SEQ ID NO: 5), P111 (SEQ ID NO: 112), P112 (SEQ ID NO: 113), P113 (SEQ ID NO: 114), P114 (SEQ ID NO: 115), P115 (SEQ ID NO: 116), P116 (SEQ ID NO: 117), P117 (SEQ ID NO: 118), P118 (SEQ ID NO: 119), P123, (SEQ ID NO: 124), P124 (SEQ ID NO: 125), and P125 (SEQ ID NO: 126).

2. The peptide according to claim 1, wherein the peptide induces aggregation of at least one protein selected from:
a) a 3-phenylpropionate-dihydrodiol/cinnamic acid-dihydrodiol dehydrogenase (Hcab), a chaperone protein skp (Skp), a phosphate regulon sensor protein (PhoR), a dipeptide and tripeptide permease A (Dtpa), a probable sensor-like histidine kinase YedV (YedV), an uncharacterized Na(+)/H(+) exchanger YjcE (YjcE), an osmolarity sensor protein EnvZ (EnvZ), a sensor protein RstB (RstB), a sensor protein ZraS (ZraS), a putative uncharacterized protein YbfO (YbfO), a sensor histidine kinase DcuS (DcuS), a signal transduction histidine-protein kinaseAtoS (AtoS), aformate hydrogenlyase subunit 4 (hycD), an aromatic amino acid exporter YddG (YddG), a UPF0226 protein YfcJ (YfcJ), an inner membrane protein yfeZ (YfeZ), sensor protein CpxA (CpxA), sensor protein CreC (CreC), and UPF0114 protein YghA (YqhA);
b) one or more proteins having an amino acid sequence selected from the group consisting of SEQ ID NOs: 128, and 202-215; and/or
c) one or more proteins having an amino acid sequence selected from the group consisting of SEQ ID NOs: 128, 203, 207, 208, 210, 213, 216, 217, 218, 219, 220, 221, and 222.

3. The peptide according to claim 1, wherein the peptide induces aggregation of one or more primary target proteins by co-aggregating with one or more aggregation prone regions (APRs) in one or more primary target proteins and the amino acid sequence of one or more APRs is selected from the group consisting of: GLGLALV (SEQ ID NO: 128), GLGLALA (SEQ ID NO: 202), GLGLAIV (SEQ ID NO: 203), GLGLAMV (SEQ ID NO: 204), GLGLSLV (SEQ ID NO: 205), GLALALV (SEQ ID NO: 206), GLGLAVV (SEQ ID NO: 207), GLPLALV (SEQ ID NO: 208), GVGLALV (SEQ ID NO: 209), GLGLALS (SEQ ID NO: 210), GLLLALV (SEQ ID NO: 211), GLGLALQ (SEQ ID NO: 212), GIGLALV (SEQ ID NO: 213), GLGLAFV (SEQ ID NO: 214), and GLSLALV (SEQ ID NO: 215).

4. The peptide according to claim 1, wherein the bacterium is Gram-negative, or wherein the bacterium is *Escherichia* or *Acinetobacter*, or wherein the bacterium is *Escherichia coli, Acinetobacter radioresistens* or *Acinetobacter baumanii.*

5. The peptide according to claim 1, wherein the peptide shows Minimum Inhibitory Concentration (MIC) against said bacterium of less than 32 μg/ml, or 25 μg/mL or less, 12 μg/mL or less, or 6 μg/mL or less.

6. The peptide of claim 1, further comprising:
   a) a detectable label;
   b) a molecule which increases the half-life; or
   c) a moiety that increases solubility of the molecule.

7. The peptide of claim 1, wherein the peptide displays anti-bacterial effects against more than one bacterial taxon, wherein the more than one bacterial taxon is a bacterial genus, species or strain.

8. A pharmaceutical composition, comprising the peptide of claim 1, and a pharmaceutically acceptable carrier.

9. A method for treating a bacterial infection in a subject, comprising administering the peptide of claim 1.

* * * * *

SEQUENCE LISTING

```
<160> NUMBER OF SEQ ID NOS: 236

<210> SEQ ID NO 1
<211> LENGTH: 21
<212> TYPE: PRT
<213> ORGANISM: Artificial Sequence
<220> FEATURE:
<223> OTHER INFORMATION: Peptide sequence

<400> SEQUENCE: 1

Arg Gly Leu Gly Leu Ala Leu Val Arg Arg Pro Arg Gly Leu Gly Leu
1               5                   10                  15

Ala Leu Val Arg Arg
            20

<210> SEQ ID NO 2
<211> LENGTH: 21
<212> TYPE: PRT
<213> ORGANISM: Artificial Sequence
<220> FEATURE:
<223> OTHER INFORMATION: Peptide sequience

<400> SEQUENCE: 2

Arg Gly Leu Gly Pro Ala Leu Pro Arg Arg Pro Arg Gly Leu Gly Pro
1               5                   10                  15

Ala Leu Pro Arg Arg
            20

<210> SEQ ID NO 3
<211> LENGTH: 21
<212> TYPE: PRT
<213> ORGANISM: Artificial Sequence
<220> FEATURE:
<223> OTHER INFORMATION: Peptide sequence

<400> SEQUENCE: 3

Arg Ala Leu Leu Thr Thr Leu Leu Arg Arg Pro Arg Ala Leu Leu Thr
1               5                   10                  15

Thr Leu Leu Arg Arg
            20

<210> SEQ ID NO 4
```

```
<211> LENGTH: 22
<212> TYPE: PRT
<213> ORGANISM: Artificial Sequence
<220> FEATURE:
<223> OTHER INFORMATION: Peptide sequence

<400> SEQUENCE: 4

Arg Arg Ala Leu Leu Thr Thr Leu Leu Arg Arg Pro Arg Ala Leu Leu
1               5                   10                  15

Thr Thr Leu Leu Arg Arg
            20

<210> SEQ ID NO 5
<211> LENGTH: 21
<212> TYPE: PRT
<213> ORGANISM: Artificial Sequence
<220> FEATURE:
<223> OTHER INFORMATION: Peptide sequience

<400> SEQUENCE: 5

Arg Ala Leu Leu Arg Thr Leu Leu Arg Arg Pro Arg Ala Leu Leu Thr
1               5                   10                  15

Thr Leu Leu Arg Arg
            20

<210> SEQ ID NO 6
<211> LENGTH: 21
<212> TYPE: PRT
<213> ORGANISM: Artificial Sequence
<220> FEATURE:
<223> OTHER INFORMATION: Peptide sequence

<400> SEQUENCE: 6

Arg Gly Leu Leu Ala Leu Leu Ala Arg Arg Pro Arg Gly Leu Leu Ala
1               5                   10                  15

Leu Leu Ala Arg Arg
            20

<210> SEQ ID NO 7
<211> LENGTH: 21
<212> TYPE: PRT
<213> ORGANISM: Artificial Sequence
<220> FEATURE:
<223> OTHER INFORMATION: Peptide sequence

<400> SEQUENCE: 7

Arg Leu Leu Leu Ser Leu Leu Val Arg Arg Pro Arg Leu Leu Leu Ser
1               5                   10                  15

Leu Leu Val Arg Arg
            20

<210> SEQ ID NO 8
<211> LENGTH: 21
<212> TYPE: PRT
<213> ORGANISM: Artificial Sequence
<220> FEATURE:
<223> OTHER INFORMATION: Peptide sequence

<400> SEQUENCE: 8

Arg Leu Leu Leu Ala Leu Leu Ser Arg Arg Pro Arg Leu Leu Leu Ala
1               5                   10                  15

Leu Leu Ser Arg Arg
            20
```

```
<210> SEQ ID NO 9
<211> LENGTH: 21
<212> TYPE: PRT
<213> ORGANISM: Artificial Sequence
<220> FEATURE:
<223> OTHER INFORMATION: Peptide sequence

<400> SEQUENCE: 9

Arg Leu Ala Leu Ala Leu Leu Leu Arg Arg Pro Arg Leu Ala Leu Ala
1               5                   10                  15

Leu Leu Leu Arg Arg
            20

<210> SEQ ID NO 10
<211> LENGTH: 21
<212> TYPE: PRT
<213> ORGANISM: Artificial Sequence
<220> FEATURE:
<223> OTHER INFORMATION: Peptide sequence

<400> SEQUENCE: 10

Arg Thr Val Thr Val Thr Phe Gly Arg Arg Pro Arg Thr Val Thr Val
1               5                   10                  15

Thr Phe Gly Arg Arg
            20

<210> SEQ ID NO 11
<211> LENGTH: 21
<212> TYPE: PRT
<213> ORGANISM: Artificial Sequence
<220> FEATURE:
<223> OTHER INFORMATION: Peptide sequence

<400> SEQUENCE: 11

Arg Thr Val Thr Val Thr Phe Gly Arg Arg Pro Arg Thr Val Thr Val
1               5                   10                  15

Thr Phe Gly Arg Arg
            20

<210> SEQ ID NO 12
<211> LENGTH: 21
<212> TYPE: PRT
<213> ORGANISM: Artificial Sequence
<220> FEATURE:
<223> OTHER INFORMATION: Peptide sequence

<400> SEQUENCE: 12

Arg Ile Gly Ala Leu Leu Leu Arg Arg Pro Arg Ile Gly Ala Leu
1               5                   10                  15

Leu Leu Leu Arg Arg
            20

<210> SEQ ID NO 13
<211> LENGTH: 21
<212> TYPE: PRT
<213> ORGANISM: Artificial Sequence
<220> FEATURE:
<223> OTHER INFORMATION: Peptide sequence

<400> SEQUENCE: 13

Arg Thr Val Thr Val Thr Phe Asn Arg Arg Pro Arg Thr Val Thr Val
1               5                   10                  15

Thr Phe Asn Arg Arg
            20
```

```
<210> SEQ ID NO 14
<211> LENGTH: 21
<212> TYPE: PRT
<213> ORGANISM: Artificial Sequence
<220> FEATURE:
<223> OTHER INFORMATION: Peptide sequence

<400> SEQUENCE: 14

Arg Ala Leu Ile Ala Ala Leu Gln Arg Arg Pro Arg Ala Leu Ile Ala
1               5                   10                  15

Ala Leu Gln Arg Arg
            20

<210> SEQ ID NO 15
<211> LENGTH: 21
<212> TYPE: PRT
<213> ORGANISM: Artificial Sequence
<220> FEATURE:
<223> OTHER INFORMATION: Peptide sequence

<400> SEQUENCE: 15

Arg Val Leu Ala Leu Ala Ala Leu Arg Arg Pro Arg Val Leu Ala Leu
1               5                   10                  15

Ala Ala Leu Arg Arg
            20

<210> SEQ ID NO 16
<211> LENGTH: 21
<212> TYPE: PRT
<213> ORGANISM: Artificial Sequence
<220> FEATURE:
<223> OTHER INFORMATION: Peptide sequence

<400> SEQUENCE: 16

Arg Ala Leu Ala Val Ala Leu Leu Arg Arg Pro Arg Ala Leu Ala Val
1               5                   10                  15

Ala Leu Leu Arg Arg
            20

<210> SEQ ID NO 17
<211> LENGTH: 21
<212> TYPE: PRT
<213> ORGANISM: Artificial Sequence
<220> FEATURE:
<223> OTHER INFORMATION: Peptide sequence

<400> SEQUENCE: 17

Arg Ala Val Leu Gly Leu Leu Ala Arg Arg Pro Arg Ala Val Leu Gly
1               5                   10                  15

Leu Leu Ala Arg Arg
            20

<210> SEQ ID NO 18
<211> LENGTH: 21
<212> TYPE: PRT
<213> ORGANISM: Artificial Sequence
<220> FEATURE:
<223> OTHER INFORMATION: Peptide sequence

<400> SEQUENCE: 18

Arg Leu Ile Gly Ile Ala Leu Gly Arg Arg Pro Arg Leu Ile Gly Ile
1               5                   10                  15

Ala Leu Gly Arg Arg
            20
```

<210> SEQ ID NO 19
<211> LENGTH: 21
<212> TYPE: PRT
<213> ORGANISM: Artificial Sequence
<220> FEATURE:
<223> OTHER INFORMATION: Peptide sequence

<400> SEQUENCE: 19

Arg Ala Leu Leu Thr Ala Val Leu Arg Arg Pro Arg Ala Leu Leu Thr
1               5                   10                  15

Ala Val Leu Arg Arg
            20

<210> SEQ ID NO 20
<211> LENGTH: 21
<212> TYPE: PRT
<213> ORGANISM: Artificial Sequence
<220> FEATURE:
<223> OTHER INFORMATION: Peptide sequence

<400> SEQUENCE: 20

Arg Gln Leu Val Ala Leu Leu Val Arg Arg Pro Arg Gln Leu Val Ala
1               5                   10                  15

Leu Leu Val Arg Arg
            20

<210> SEQ ID NO 21
<211> LENGTH: 21
<212> TYPE: PRT
<213> ORGANISM: Artificial Sequence
<220> FEATURE:
<223> OTHER INFORMATION: Peptide sequence

<400> SEQUENCE: 21

Arg Ser Ala Val Leu Ala Leu Leu Arg Arg Pro Arg Ser Ala Val Leu
1               5                   10                  15

Ala Leu Leu Arg Arg
            20

<210> SEQ ID NO 22
<211> LENGTH: 21
<212> TYPE: PRT
<213> ORGANISM: Artificial Sequence
<220> FEATURE:
<223> OTHER INFORMATION: Peptide sequence

<400> SEQUENCE: 22

Arg Val Val Thr Val Thr Leu Asn Arg Arg Pro Arg Val Val Thr Val
1               5                   10                  15

Thr Leu Asn Arg Arg
            20

<210> SEQ ID NO 23
<211> LENGTH: 21
<212> TYPE: PRT
<213> ORGANISM: Artificial Sequence
<220> FEATURE:
<223> OTHER INFORMATION: Peptide sequence

<400> SEQUENCE: 23

Arg Ala Val Val Leu Ala Thr Gly Arg Arg Pro Arg Ala Val Val Leu
1               5                   10                  15

Ala Thr Gly Arg Arg

20

<210> SEQ ID NO 24
<211> LENGTH: 21
<212> TYPE: PRT
<213> ORGANISM: Artificial Sequence
<220> FEATURE:
<223> OTHER INFORMATION: Peptide sequence

<400> SEQUENCE: 24

Arg Leu Leu Leu Ile Val Leu Gly Arg Arg Pro Arg Leu Leu Leu Ile
1               5                   10                  15

Val Leu Gly Arg Arg
            20

<210> SEQ ID NO 25
<211> LENGTH: 21
<212> TYPE: PRT
<213> ORGANISM: Artificial Sequence
<220> FEATURE:
<223> OTHER INFORMATION: Peptide sequence

<400> SEQUENCE: 25

Arg Ala Leu Ala Val Ala Ile Gly Arg Arg Pro Arg Ala Leu Ala Val
1               5                   10                  15

Ala Ile Gly Arg Arg
            20

<210> SEQ ID NO 26
<211> LENGTH: 21
<212> TYPE: PRT
<213> ORGANISM: Artificial Sequence
<220> FEATURE:
<223> OTHER INFORMATION: Peptide sequence

<400> SEQUENCE: 26

Arg Ala Leu Leu Ile Thr Leu Leu Arg Arg Pro Arg Ala Leu Leu Ile
1               5                   10                  15

Thr Leu Leu Arg Arg
            20

<210> SEQ ID NO 27
<211> LENGTH: 21
<212> TYPE: PRT
<213> ORGANISM: Artificial Sequence
<220> FEATURE:
<223> OTHER INFORMATION: Peptide sequence

<400> SEQUENCE: 27

Arg Gly Leu Leu Leu Ala Leu Gln Arg Arg Pro Arg Gly Leu Leu Leu
1               5                   10                  15

Ala Leu Gln Arg Arg
            20

<210> SEQ ID NO 28
<211> LENGTH: 21
<212> TYPE: PRT
<213> ORGANISM: Artificial Sequence
<220> FEATURE:
<223> OTHER INFORMATION: Peptide sequence

<400> SEQUENCE: 28

Arg Ile Val Thr Val Thr Leu Asn Arg Arg Pro Arg Ile Val Thr Val
1               5                   10                  15

```
Thr Leu Asn Arg Arg
        20

<210> SEQ ID NO 29
<211> LENGTH: 21
<212> TYPE: PRT
<213> ORGANISM: Artificial Sequence
<220> FEATURE:
<223> OTHER INFORMATION: Peptide sequence

<400> SEQUENCE: 29

Arg Leu Phe Val Gly Leu Ala Leu Arg Arg Pro Arg Leu Phe Val Gly
1               5                   10                  15

Leu Ala Leu Arg Arg
        20

<210> SEQ ID NO 30
<211> LENGTH: 21
<212> TYPE: PRT
<213> ORGANISM: Artificial Sequence
<220> FEATURE:
<223> OTHER INFORMATION: Peptide sequence

<400> SEQUENCE: 30

Arg Val Leu Gly Leu Ala Ala Leu Arg Arg Pro Arg Val Leu Gly Leu
1               5                   10                  15

Ala Ala Leu Arg Arg
        20

<210> SEQ ID NO 31
<211> LENGTH: 21
<212> TYPE: PRT
<213> ORGANISM: Artificial Sequence
<220> FEATURE:
<223> OTHER INFORMATION: Peptide sequence

<400> SEQUENCE: 31

Arg Val Val Gly Leu Leu Ala Gly Arg Arg Pro Arg Val Val Gly Leu
1               5                   10                  15

Leu Ala Gly Arg Arg
        20

<210> SEQ ID NO 32
<211> LENGTH: 21
<212> TYPE: PRT
<213> ORGANISM: Artificial Sequence
<220> FEATURE:
<223> OTHER INFORMATION: Peptide sequence

<400> SEQUENCE: 32

Arg Ala Thr Val Leu Ala Leu Leu Arg Arg Pro Arg Ala Thr Val Leu
1               5                   10                  15

Ala Leu Leu Arg Arg
        20

<210> SEQ ID NO 33
<211> LENGTH: 21
<212> TYPE: PRT
<213> ORGANISM: Artificial Sequence
<220> FEATURE:
<223> OTHER INFORMATION: Peptide sequence

<400> SEQUENCE: 33

Arg Ala Val Leu Val Ala Ile Gly Arg Arg Pro Arg Ala Val Leu Val
1               5                   10                  15
```

```
Ala Ile Gly Arg Arg
            20

<210> SEQ ID NO 34
<211> LENGTH: 21
<212> TYPE: PRT
<213> ORGANISM: Artificial Sequence
<220> FEATURE:
<223> OTHER INFORMATION: Peptide sequence

<400> SEQUENCE: 34

Arg Gly Leu Leu Val Thr Leu Ala Arg Arg Pro Arg Gly Leu Leu Val
1               5                   10                  15

Thr Leu Ala Arg Arg
            20

<210> SEQ ID NO 35
<211> LENGTH: 21
<212> TYPE: PRT
<213> ORGANISM: Artificial Sequence
<220> FEATURE:
<223> OTHER INFORMATION: Peptide sequence

<400> SEQUENCE: 35

Arg Leu Phe Val Ile Leu Ala Leu Arg Arg Pro Arg Leu Phe Val Ile
1               5                   10                  15

Leu Ala Leu Arg Arg
            20

<210> SEQ ID NO 36
<211> LENGTH: 21
<212> TYPE: PRT
<213> ORGANISM: Artificial Sequence
<220> FEATURE:
<223> OTHER INFORMATION: Peptide sequence

<400> SEQUENCE: 36

Arg Leu Gly Ile Ala Val Ala Leu Arg Arg Pro Arg Leu Gly Ile Ala
1               5                   10                  15

Val Ala Leu Arg Arg
            20

<210> SEQ ID NO 37
<211> LENGTH: 21
<212> TYPE: PRT
<213> ORGANISM: Artificial Sequence
<220> FEATURE:
<223> OTHER INFORMATION: Peptide sequence

<400> SEQUENCE: 37

Arg Leu Leu Leu Leu Val Asn Leu Arg Arg Pro Arg Leu Leu Leu Leu
1               5                   10                  15

Val Asn Leu Arg Arg
            20

<210> SEQ ID NO 38
<211> LENGTH: 21
<212> TYPE: PRT
<213> ORGANISM: Artificial Sequence
<220> FEATURE:
<223> OTHER INFORMATION: Peptide sequence

<400> SEQUENCE: 38

Arg Thr Val Thr Val Ala Leu Gly Arg Arg Pro Arg Thr Val Thr Val
```

```
1               5                   10                  15

Ala Leu Gly Arg Arg
            20

<210> SEQ ID NO 39
<211> LENGTH: 21
<212> TYPE: PRT
<213> ORGANISM: Artificial Sequence
<220> FEATURE:
<223> OTHER INFORMATION: Peptide sequence

<400> SEQUENCE: 39

Arg Val Gly Val Ile Val Gly Ala Arg Arg Pro Arg Val Gly Val Ile
1               5                   10                  15

Val Gly Ala Arg Arg
            20

<210> SEQ ID NO 40
<211> LENGTH: 21
<212> TYPE: PRT
<213> ORGANISM: Artificial Sequence
<220> FEATURE:
<223> OTHER INFORMATION: Peptide sequence

<400> SEQUENCE: 40

Arg Val Val Val Ala Ile Ala Leu Arg Arg Pro Arg Val Val Val Ala
1               5                   10                  15

Ile Ala Leu Arg Arg
            20

<210> SEQ ID NO 41
<211> LENGTH: 21
<212> TYPE: PRT
<213> ORGANISM: Artificial Sequence
<220> FEATURE:
<223> OTHER INFORMATION: Peptide sequence

<400> SEQUENCE: 41

Arg Ala Gly Leu Leu Ser Leu Val Arg Arg Pro Arg Ala Gly Leu Leu
1               5                   10                  15

Ser Leu Val Arg Arg
            20

<210> SEQ ID NO 42
<211> LENGTH: 21
<212> TYPE: PRT
<213> ORGANISM: Artificial Sequence
<220> FEATURE:
<223> OTHER INFORMATION: Peptide sequence

<400> SEQUENCE: 42

Arg Ala Gly Leu Leu Ser Leu Val Arg Arg Pro Arg Ala Gly Leu Leu
1               5                   10                  15

Ser Leu Val Arg Arg
            20

<210> SEQ ID NO 43
<211> LENGTH: 21
<212> TYPE: PRT
<213> ORGANISM: Artificial Sequence
<220> FEATURE:
<223> OTHER INFORMATION: Peptide sequence

<400> SEQUENCE: 43
```

```
Arg Ala Gln Val Leu Ala Leu Leu Arg Arg Pro Arg Ala Gln Val Leu
1               5                   10                  15

Ala Leu Leu Arg Arg
            20

<210> SEQ ID NO 44
<211> LENGTH: 21
<212> TYPE: PRT
<213> ORGANISM: Artificial Sequence
<220> FEATURE:
<223> OTHER INFORMATION: Peptide sequence

<400> SEQUENCE: 44

Arg Ala Val Val Leu Ala Val Asn Arg Arg Pro Arg Ala Val Val Leu
1               5                   10                  15

Ala Val Asn Arg Arg
            20

<210> SEQ ID NO 45
<211> LENGTH: 21
<212> TYPE: PRT
<213> ORGANISM: Artificial Sequence
<220> FEATURE:
<223> OTHER INFORMATION: Peptide sequence

<400> SEQUENCE: 45

Arg Phe Val Ala Gly Phe Ile Gly Arg Arg Pro Arg Phe Val Ala Gly
1               5                   10                  15

Phe Ile Gly Arg Arg
            20

<210> SEQ ID NO 46
<211> LENGTH: 21
<212> TYPE: PRT
<213> ORGANISM: Artificial Sequence
<220> FEATURE:
<223> OTHER INFORMATION: Peptide sequence

<400> SEQUENCE: 46

Arg Leu Ala Ile Ala Leu Ala Gln Arg Arg Pro Arg Leu Ala Ile Ala
1               5                   10                  15

Leu Ala Gln Arg Arg
            20

<210> SEQ ID NO 47
<211> LENGTH: 21
<212> TYPE: PRT
<213> ORGANISM: Artificial Sequence
<220> FEATURE:
<223> OTHER INFORMATION: Peptide sequence

<400> SEQUENCE: 47

Arg Leu Phe Ile Ile Ala Thr Ala Arg Arg Pro Arg Leu Phe Ile Ile
1               5                   10                  15

Ala Thr Ala Arg Arg
            20

<210> SEQ ID NO 48
<211> LENGTH: 21
<212> TYPE: PRT
<213> ORGANISM: Artificial Sequence
<220> FEATURE:
<223> OTHER INFORMATION: Peptide sequence

<400> SEQUENCE: 48
```

```
Arg Leu Ile Val Ala Ala Ile Ala Arg Arg Pro Arg Leu Ile Val Ala
1               5                   10                  15

Ala Ile Ala Arg Arg
            20

<210> SEQ ID NO 49
<211> LENGTH: 21
<212> TYPE: PRT
<213> ORGANISM: Artificial Sequence
<220> FEATURE:
<223> OTHER INFORMATION: Peptide sequence

<400> SEQUENCE: 49

Arg Leu Leu Ala Gly Ile Val Ala Arg Arg Pro Arg Leu Leu Ala Gly
1               5                   10                  15

Ile Val Ala Arg Arg
            20

<210> SEQ ID NO 50
<211> LENGTH: 21
<212> TYPE: PRT
<213> ORGANISM: Artificial Sequence
<220> FEATURE:
<223> OTHER INFORMATION: Peptide sequence

<400> SEQUENCE: 50

Arg Leu Leu Leu Ala Tyr Leu Leu Arg Arg Pro Arg Leu Leu Leu Ala
1               5                   10                  15

Tyr Leu Leu Arg Arg
            20

<210> SEQ ID NO 51
<211> LENGTH: 21
<212> TYPE: PRT
<213> ORGANISM: Artificial Sequence
<220> FEATURE:
<223> OTHER INFORMATION: Peptide sequence

<400> SEQUENCE: 51

Arg Leu Leu Leu Met Leu Ala Gly Arg Arg Pro Arg Leu Leu Leu Met
1               5                   10                  15

Leu Ala Gly Arg Arg
            20

<210> SEQ ID NO 52
<211> LENGTH: 21
<212> TYPE: PRT
<213> ORGANISM: Artificial Sequence
<220> FEATURE:
<223> OTHER INFORMATION: Peptide sequence

<400> SEQUENCE: 52

Arg Leu Leu Thr Leu Leu Asn Leu Arg Arg Pro Arg Leu Leu Thr Leu
1               5                   10                  15

Leu Asn Leu Arg Arg
            20

<210> SEQ ID NO 53
<211> LENGTH: 21
<212> TYPE: PRT
<213> ORGANISM: Artificial Sequence
<220> FEATURE:
<223> OTHER INFORMATION: Peptide sequence
```

```
<400> SEQUENCE: 53

Arg Leu Val Gly Leu Val Leu Gly Arg Arg Pro Arg Leu Val Gly Leu
1               5                   10                  15

Val Leu Gly Arg Arg
            20

<210> SEQ ID NO 54
<211> LENGTH: 21
<212> TYPE: PRT
<213> ORGANISM: Artificial Sequence
<220> FEATURE:
<223> OTHER INFORMATION: Peptide sequence

<400> SEQUENCE: 54

Arg Leu Val Val Thr Ala Ile Ala Arg Arg Pro Arg Leu Val Val Thr
1               5                   10                  15

Ala Ile Ala Arg Arg
            20

<210> SEQ ID NO 55
<211> LENGTH: 21
<212> TYPE: PRT
<213> ORGANISM: Artificial Sequence
<220> FEATURE:
<223> OTHER INFORMATION: Peptide sequence

<400> SEQUENCE: 55

Arg Pro Val Ile Ile Leu Thr Ala Arg Arg Pro Arg Pro Val Ile Ile
1               5                   10                  15

Leu Thr Ala Arg Arg
            20

<210> SEQ ID NO 56
<211> LENGTH: 21
<212> TYPE: PRT
<213> ORGANISM: Artificial Sequence
<220> FEATURE:
<223> OTHER INFORMATION: Peptide sequence

<400> SEQUENCE: 56

Arg Gln Ala Ile Val Ile Thr Gly Arg Arg Pro Arg Gln Ala Ile Val
1               5                   10                  15

Ile Thr Gly Arg Arg
            20

<210> SEQ ID NO 57
<211> LENGTH: 21
<212> TYPE: PRT
<213> ORGANISM: Artificial Sequence
<220> FEATURE:
<223> OTHER INFORMATION: Peptide sequence

<400> SEQUENCE: 57

Arg Thr Val Val Leu Leu Ala Ala Arg Arg Pro Arg Thr Val Val Leu
1               5                   10                  15

Leu Ala Ala Arg Arg
            20

<210> SEQ ID NO 58
<211> LENGTH: 21
<212> TYPE: PRT
<213> ORGANISM: Artificial Sequence
<220> FEATURE:
<223> OTHER INFORMATION: Peptide sequence
```

<400> SEQUENCE: 58

Arg Ala Ala Leu Ile Thr Ala Leu Arg Arg Pro Arg Ala Ala Leu Ile
1               5                   10                  15

Thr Ala Leu Arg Arg
            20

<210> SEQ ID NO 59
<211> LENGTH: 21
<212> TYPE: PRT
<213> ORGANISM: Artificial Sequence
<220> FEATURE:
<223> OTHER INFORMATION: Peptide sequence

<400> SEQUENCE: 59

Arg Ala Ala Leu Leu Ala Tyr Val Arg Arg Pro Arg Ala Ala Leu Leu
1               5                   10                  15

Ala Tyr Val Arg Arg
            20

<210> SEQ ID NO 60
<211> LENGTH: 21
<212> TYPE: PRT
<213> ORGANISM: Artificial Sequence
<220> FEATURE:
<223> OTHER INFORMATION: Peptide sequence

<400> SEQUENCE: 60

Arg Ala Ile Thr Leu Val Leu Thr Arg Arg Pro Arg Ala Ile Thr Leu
1               5                   10                  15

Val Leu Thr Arg Arg
            20

<210> SEQ ID NO 61
<211> LENGTH: 21
<212> TYPE: PRT
<213> ORGANISM: Artificial Sequence
<220> FEATURE:
<223> OTHER INFORMATION: Peptide sequence

<400> SEQUENCE: 61

Arg Ala Leu Val Ser Leu Leu Leu Arg Arg Pro Arg Ala Leu Val Ser
1               5                   10                  15

Leu Leu Leu Arg Arg
            20

<210> SEQ ID NO 62
<211> LENGTH: 21
<212> TYPE: PRT
<213> ORGANISM: Artificial Sequence
<220> FEATURE:
<223> OTHER INFORMATION: Peptide sequence

<400> SEQUENCE: 62

Arg Gly Ile Val Gly Leu Val Gly Arg Arg Pro Arg Gly Ile Val Gly
1               5                   10                  15

Leu Val Gly Arg Arg
            20

<210> SEQ ID NO 63
<211> LENGTH: 21
<212> TYPE: PRT
<213> ORGANISM: Artificial Sequence
<220> FEATURE:

```
<223> OTHER INFORMATION: Peptide sequence

<400> SEQUENCE: 63

Arg Gly Leu Ala Val Gly Val Ile Arg Arg Pro Arg Gly Leu Ala Val
1               5                   10                  15

Gly Val Ile Arg Arg
            20

<210> SEQ ID NO 64
<211> LENGTH: 21
<212> TYPE: PRT
<213> ORGANISM: Artificial Sequence
<220> FEATURE:
<223> OTHER INFORMATION: Peptide sequence

<400> SEQUENCE: 64

Arg Gly Thr Val Leu Leu Val Ser Arg Arg Pro Arg Gly Thr Val Leu
1               5                   10                  15

Leu Val Ser Arg Arg
            20

<210> SEQ ID NO 65
<211> LENGTH: 21
<212> TYPE: PRT
<213> ORGANISM: Artificial Sequence
<220> FEATURE:
<223> OTHER INFORMATION: Peptide sequence

<400> SEQUENCE: 65

Arg Gly Val Ala Leu Val Val Ala Arg Arg Pro Arg Gly Val Ala Leu
1               5                   10                  15

Val Val Ala Arg Arg
            20

<210> SEQ ID NO 66
<211> LENGTH: 21
<212> TYPE: PRT
<213> ORGANISM: Artificial Sequence
<220> FEATURE:
<223> OTHER INFORMATION: Peptide sequence

<400> SEQUENCE: 66

Arg Gly Val Leu Ala Val Phe Ala Arg Arg Pro Arg Gly Val Leu Ala
1               5                   10                  15

Val Phe Ala Arg Arg
            20

<210> SEQ ID NO 67
<211> LENGTH: 21
<212> TYPE: PRT
<213> ORGANISM: Artificial Sequence
<220> FEATURE:
<223> OTHER INFORMATION: Peptide sequence

<400> SEQUENCE: 67

Arg Ile Leu Leu Leu Thr Leu Val Arg Arg Pro Arg Ile Leu Leu Leu
1               5                   10                  15

Thr Leu Val Arg Arg
            20

<210> SEQ ID NO 68
<211> LENGTH: 21
<212> TYPE: PRT
<213> ORGANISM: Artificial Sequence
```

```
<220> FEATURE:
<223> OTHER INFORMATION: Peptide sequence

<400> SEQUENCE: 68

Arg Ile Val Ile Val Gly Gly Arg Arg Pro Arg Ile Val Ile Val
1               5                   10                  15

Gly Gly Gly Arg Arg
            20

<210> SEQ ID NO 69
<211> LENGTH: 21
<212> TYPE: PRT
<213> ORGANISM: Artificial Sequence
<220> FEATURE:
<223> OTHER INFORMATION: Peptide sequence

<400> SEQUENCE: 69

Arg Leu Leu Ala Ile Leu Ala Ser Arg Arg Pro Arg Leu Leu Ala Ile
1               5                   10                  15

Leu Ala Ser Arg Arg
            20

<210> SEQ ID NO 70
<211> LENGTH: 21
<212> TYPE: PRT
<213> ORGANISM: Artificial Sequence
<220> FEATURE:
<223> OTHER INFORMATION: Peptide sequence

<400> SEQUENCE: 70

Arg Leu Leu Ile Ala Val Gly Ala Arg Arg Pro Arg Leu Leu Ile Ala
1               5                   10                  15

Val Gly Ala Arg Arg
            20

<210> SEQ ID NO 71
<211> LENGTH: 21
<212> TYPE: PRT
<213> ORGANISM: Artificial Sequence
<220> FEATURE:
<223> OTHER INFORMATION: Peptide sequence

<400> SEQUENCE: 71

Arg Leu Leu Ile Val Leu Gly Ala Arg Arg Pro Arg Leu Leu Ile Val
1               5                   10                  15

Leu Gly Ala Arg Arg
            20

<210> SEQ ID NO 72
<211> LENGTH: 21
<212> TYPE: PRT
<213> ORGANISM: Artificial Sequence
<220> FEATURE:
<223> OTHER INFORMATION: Peptide sequence

<400> SEQUENCE: 72

Arg Asn Val Val Leu Leu Ala Leu Arg Arg Pro Arg Asn Val Val Leu
1               5                   10                  15

Leu Ala Leu Arg Arg
            20

<210> SEQ ID NO 73
<211> LENGTH: 21
<212> TYPE: PRT
```

```
<213> ORGANISM: Artificial Sequence
<220> FEATURE:
<223> OTHER INFORMATION: Peptide sequence

<400> SEQUENCE: 73

Arg Pro Ala Ile Val Ala Ala Val Arg Pro Arg Pro Ala Ile Val
1               5                   10                  15

Ala Ala Val Arg Arg
            20

<210> SEQ ID NO 74
<211> LENGTH: 21
<212> TYPE: PRT
<213> ORGANISM: Artificial Sequence
<220> FEATURE:
<223> OTHER INFORMATION: Peptide sequence

<400> SEQUENCE: 74

Arg Gln Leu Leu Leu Thr Leu Leu Arg Arg Pro Arg Gln Leu Leu Leu
1               5                   10                  15

Thr Leu Leu Arg Arg
            20

<210> SEQ ID NO 75
<211> LENGTH: 21
<212> TYPE: PRT
<213> ORGANISM: Artificial Sequence
<220> FEATURE:
<223> OTHER INFORMATION: Peptide sequence

<400> SEQUENCE: 75

Arg Ser Ala Ile Ile Gly Ile Ile Arg Arg Pro Arg Ser Ala Ile Ile
1               5                   10                  15

Gly Ile Ile Arg Arg
            20

<210> SEQ ID NO 76
<211> LENGTH: 21
<212> TYPE: PRT
<213> ORGANISM: Artificial Sequence
<220> FEATURE:
<223> OTHER INFORMATION: Peptide sequence

<400> SEQUENCE: 76

Arg Val Ser Leu Val Ala Ile Leu Arg Arg Pro Arg Val Ser Leu Val
1               5                   10                  15

Ala Ile Leu Arg Arg
            20

<210> SEQ ID NO 77
<211> LENGTH: 21
<212> TYPE: PRT
<213> ORGANISM: Artificial Sequence
<220> FEATURE:
<223> OTHER INFORMATION: Peptide sequence

<400> SEQUENCE: 77

Arg Val Val Ala Leu Val Ala Gly Arg Arg Pro Arg Val Val Ala Leu
1               5                   10                  15

Val Ala Gly Arg Arg
            20

<210> SEQ ID NO 78
<211> LENGTH: 21
```

```
<212> TYPE: PRT
<213> ORGANISM: Artificial Sequence
<220> FEATURE:
<223> OTHER INFORMATION: Peptide sequience

<400> SEQUENCE: 78

Arg Leu Arg Leu Ser Leu Leu Val Arg Arg Pro Arg Leu Leu Leu Ser
1               5                   10                  15

Leu Leu Val Arg Arg
            20

<210> SEQ ID NO 79
<211> LENGTH: 21
<212> TYPE: PRT
<213> ORGANISM: Artificial Sequence
<220> FEATURE:
<223> OTHER INFORMATION: Peptide sequence

<400> SEQUENCE: 79

Arg Gly Leu Arg Leu Ala Leu Val Arg Arg Pro Arg Gly Leu Gly Leu
1               5                   10                  15

Ala Leu Val Arg Arg
            20

<210> SEQ ID NO 80
<211> LENGTH: 21
<212> TYPE: PRT
<213> ORGANISM: Artificial Sequence
<220> FEATURE:
<223> OTHER INFORMATION: Peptide sequence

<400> SEQUENCE: 80

Arg Leu Leu Leu Ala Arg Leu Ser Arg Arg Pro Arg Leu Leu Leu Ala
1               5                   10                  15

Leu Leu Ser Arg Arg
            20

<210> SEQ ID NO 81
<211> LENGTH: 21
<212> TYPE: PRT
<213> ORGANISM: Artificial Sequence
<220> FEATURE:
<223> OTHER INFORMATION: Peptide sequence

<400> SEQUENCE: 81

Arg Leu Ala Leu Arg Leu Leu Arg Arg Pro Arg Leu Ala Leu Ala
1               5                   10                  15

Leu Leu Leu Arg Arg
            20

<210> SEQ ID NO 82
<211> LENGTH: 21
<212> TYPE: PRT
<213> ORGANISM: Artificial Sequence
<220> FEATURE:
<223> OTHER INFORMATION: Peptide sequence

<400> SEQUENCE: 82

Arg Ala Leu Arg Thr Thr Leu Leu Arg Arg Pro Arg Ala Leu Leu Thr
1               5                   10                  15

Thr Leu Leu Arg Arg
            20

<210> SEQ ID NO 83
```

```
<211> LENGTH: 21
<212> TYPE: PRT
<213> ORGANISM: Artificial Sequence
<220> FEATURE:
<223> OTHER INFORMATION: Peptide sequence

<400> SEQUENCE: 83

Arg Thr Val Thr Arg Thr Phe Gly Arg Arg Pro Arg Thr Val Thr Val
1               5                   10                  15

Thr Phe Gly Arg Arg
            20

<210> SEQ ID NO 84
<211> LENGTH: 21
<212> TYPE: PRT
<213> ORGANISM: Artificial Sequence
<220> FEATURE:
<223> OTHER INFORMATION: Peptide sequience

<400> SEQUENCE: 84

Arg Thr Val Thr Val Arg Phe Gly Arg Arg Pro Arg Thr Val Thr Val
1               5                   10                  15

Thr Phe Gly Arg Arg
            20

<210> SEQ ID NO 85
<211> LENGTH: 21
<212> TYPE: PRT
<213> ORGANISM: Artificial Sequence
<220> FEATURE:
<223> OTHER INFORMATION: Peptide sequence

<400> SEQUENCE: 85

Arg Ile Arg Ala Leu Leu Leu Leu Arg Arg Pro Arg Ile Gly Ala Leu
1               5                   10                  15

Leu Leu Leu Arg Arg
            20

<210> SEQ ID NO 86
<211> LENGTH: 21
<212> TYPE: PRT
<213> ORGANISM: Artificial Sequence
<220> FEATURE:
<223> OTHER INFORMATION: Peptide sequence

<400> SEQUENCE: 86

Arg Thr Val Thr Val Thr Arg Asn Arg Arg Pro Arg Thr Val Thr Val
1               5                   10                  15

Thr Phe Asn Arg Arg
            20

<210> SEQ ID NO 87
<211> LENGTH: 21
<212> TYPE: PRT
<213> ORGANISM: Artificial Sequence
<220> FEATURE:
<223> OTHER INFORMATION: Peptide sequence

<400> SEQUENCE: 87

Arg Ala Leu Arg Ala Ala Leu Gln Arg Arg Pro Arg Ala Leu Ile Ala
1               5                   10                  15

Ala Leu Gln Arg Arg
            20
```

```
<210> SEQ ID NO 88
<211> LENGTH: 21
<212> TYPE: PRT
<213> ORGANISM: Artificial Sequence
<220> FEATURE:
<223> OTHER INFORMATION: Peptide sequence

<400> SEQUENCE: 88

Arg Val Leu Ala Arg Ala Ala Leu Arg Arg Pro Arg Val Leu Ala Leu
1               5                   10                  15

Ala Ala Leu Arg Arg
            20

<210> SEQ ID NO 89
<211> LENGTH: 21
<212> TYPE: PRT
<213> ORGANISM: Artificial Sequence
<220> FEATURE:
<223> OTHER INFORMATION: Peptide sequence

<400> SEQUENCE: 89

Arg Ala Leu Arg Val Ala Leu Leu Arg Arg Pro Arg Ala Leu Ala Val
1               5                   10                  15

Ala Leu Leu Arg Arg
            20

<210> SEQ ID NO 90
<211> LENGTH: 21
<212> TYPE: PRT
<213> ORGANISM: Artificial Sequence
<220> FEATURE:
<223> OTHER INFORMATION: Peptide sequence

<400> SEQUENCE: 90

Arg Ala Val Arg Gly Leu Leu Ala Arg Arg Pro Arg Ala Val Leu Gly
1               5                   10                  15

Leu Leu Ala Arg Arg
            20

<210> SEQ ID NO 91
<211> LENGTH: 21
<212> TYPE: PRT
<213> ORGANISM: Artificial Sequence
<220> FEATURE:
<223> OTHER INFORMATION: Peptide sequence

<400> SEQUENCE: 91

Arg Gly Leu Leu Ala Arg Leu Ala Arg Arg Pro Arg Gly Leu Leu Ala
1               5                   10                  15

Leu Leu Ala Arg Arg
            20

<210> SEQ ID NO 92
<211> LENGTH: 21
<212> TYPE: PRT
<213> ORGANISM: Artificial Sequence
<220> FEATURE:
<223> OTHER INFORMATION: Peptide sequence

<400> SEQUENCE: 92

Arg Leu Arg Gly Ile Ala Leu Gly Arg Arg Pro Arg Leu Ile Gly Ile
1               5                   10                  15

Ala Leu Gly Arg Arg
            20
```

```
<210> SEQ ID NO 93
<211> LENGTH: 21
<212> TYPE: PRT
<213> ORGANISM: Artificial Sequence
<220> FEATURE:
<223> OTHER INFORMATION: Peptide sequence

<400> SEQUENCE: 93

Arg Ala Leu Leu Thr Ala Arg Leu Arg Arg Pro Arg Ala Leu Leu Thr
1               5                   10                  15

Ala Val Leu Arg Arg
            20

<210> SEQ ID NO 94
<211> LENGTH: 21
<212> TYPE: PRT
<213> ORGANISM: Artificial Sequence
<220> FEATURE:
<223> OTHER INFORMATION: Peptide sequence

<400> SEQUENCE: 94

Arg Gln Leu Val Ala Arg Leu Val Arg Arg Pro Arg Gln Leu Val Ala
1               5                   10                  15

Leu Leu Val Arg Arg
            20

<210> SEQ ID NO 95
<211> LENGTH: 21
<212> TYPE: PRT
<213> ORGANISM: Artificial Sequence
<220> FEATURE:
<223> OTHER INFORMATION: Peptide sequence

<400> SEQUENCE: 95

Arg Ser Ala Arg Leu Ala Leu Leu Arg Arg Pro Arg Ser Ala Val Leu
1               5                   10                  15

Ala Leu Leu Arg Arg
            20

<210> SEQ ID NO 96
<211> LENGTH: 21
<212> TYPE: PRT
<213> ORGANISM: Artificial Sequence
<220> FEATURE:
<223> OTHER INFORMATION: Peptide sequence

<400> SEQUENCE: 96

Arg Val Val Thr Val Arg Leu Asn Arg Arg Pro Arg Val Val Thr Val
1               5                   10                  15

Thr Leu Asn Arg Arg
            20

<210> SEQ ID NO 97
<211> LENGTH: 21
<212> TYPE: PRT
<213> ORGANISM: Artificial Sequence
<220> FEATURE:
<223> OTHER INFORMATION: Peptde sequience

<400> SEQUENCE: 97

Arg Ala Val Arg Leu Ala Thr Gly Arg Arg Pro Arg Ala Val Val Leu
1               5                   10                  15

Ala Thr Gly Arg Arg
            20
```

```
<210> SEQ ID NO 98
<211> LENGTH: 21
<212> TYPE: PRT
<213> ORGANISM: Artificial Sequence
<220> FEATURE:
<223> OTHER INFORMATION: Peptide sequence

<400> SEQUENCE: 98

Arg Leu Arg Leu Ile Val Leu Gly Arg Arg Pro Arg Leu Leu Ile
1               5                   10                  15

Val Leu Gly Arg Arg
            20

<210> SEQ ID NO 99
<211> LENGTH: 21
<212> TYPE: PRT
<213> ORGANISM: Artificial Sequence
<220> FEATURE:
<223> OTHER INFORMATION: Peptide sequence

<400> SEQUENCE: 99

Arg Ala Arg Ala Val Ala Ile Gly Arg Arg Pro Arg Ala Leu Ala Val
1               5                   10                  15

Ala Ile Gly Arg Arg
            20

<210> SEQ ID NO 100
<211> LENGTH: 21
<212> TYPE: PRT
<213> ORGANISM: Artificial Sequence
<220> FEATURE:
<223> OTHER INFORMATION: Peptide sequence

<400> SEQUENCE: 100

Arg Ala Arg Leu Ile Thr Leu Leu Arg Arg Pro Arg Ala Leu Leu Ile
1               5                   10                  15

Thr Leu Leu Arg Arg
            20

<210> SEQ ID NO 101
<211> LENGTH: 21
<212> TYPE: PRT
<213> ORGANISM: Artificial Sequence
<220> FEATURE:
<223> OTHER INFORMATION: Peptide sequence

<400> SEQUENCE: 101

Arg Gly Leu Arg Leu Ala Leu Gln Arg Arg Pro Arg Gly Leu Leu Leu
1               5                   10                  15

Ala Leu Gln Arg Arg
            20

<210> SEQ ID NO 102
<211> LENGTH: 21
<212> TYPE: PRT
<213> ORGANISM: Artificial Sequence
<220> FEATURE:
<223> OTHER INFORMATION: Peptide sequence

<400> SEQUENCE: 102

Arg Leu Leu Arg Ser Leu Leu Val Arg Arg Pro Arg Leu Leu Leu Ser
1               5                   10                  15

Leu Leu Val Arg Arg
```

-continued

```
                    20

<210> SEQ ID NO 103
<211> LENGTH: 21
<212> TYPE: PRT
<213> ORGANISM: Artificial Sequence
<220> FEATURE:
<223> OTHER INFORMATION: Peptide sequence

<400> SEQUENCE: 103

Arg Leu Leu Arg Ser Leu Leu Val Arg Arg Pro Arg Leu Leu Leu Ser
1               5                   10                  15

Leu Leu Val Arg Arg
            20

<210> SEQ ID NO 104
<211> LENGTH: 21
<212> TYPE: PRT
<213> ORGANISM: Artificial Sequence
<220> FEATURE:
<223> OTHER INFORMATION: Peptide sequence

<400> SEQUENCE: 104

Arg Gly Leu Gly Arg Ala Leu Val Arg Arg Pro Arg Gly Leu Gly Leu
1               5                   10                  15

Ala Leu Val Arg Arg
            20

<210> SEQ ID NO 105
<211> LENGTH: 21
<212> TYPE: PRT
<213> ORGANISM: Artificial Sequence
<220> FEATURE:
<223> OTHER INFORMATION: Peptide sequence

<400> SEQUENCE: 105

Arg Leu Leu Leu Ala Leu Arg Ser Arg Arg Pro Arg Leu Leu Leu Ala
1               5                   10                  15

Leu Leu Ser Arg Arg
            20

<210> SEQ ID NO 106
<211> LENGTH: 21
<212> TYPE: PRT
<213> ORGANISM: Artificial Sequence
<220> FEATURE:
<223> OTHER INFORMATION: Peptide sequience

<400> SEQUENCE: 106

Arg Leu Ala Leu Ala Arg Leu Leu Arg Arg Pro Arg Leu Ala Leu Ala
1               5                   10                  15

Leu Leu Leu Arg Arg
            20

<210> SEQ ID NO 107
<211> LENGTH: 21
<212> TYPE: PRT
<213> ORGANISM: Artificial Sequence
<220> FEATURE:
<223> OTHER INFORMATION: Peptide sequence

<400> SEQUENCE: 107

Arg Leu Ala Leu Ala Arg Leu Leu Arg Arg Pro Arg Leu Ala Leu Ala
1               5                   10                  15
```

Leu Leu Leu Arg Arg
            20

<210> SEQ ID NO 108
<211> LENGTH: 21
<212> TYPE: PRT
<213> ORGANISM: Artificial Sequence
<220> FEATURE:
<223> OTHER INFORMATION: Peptide sequence

<400> SEQUENCE: 108

Arg Thr Val Thr Val Thr Arg Gly Arg Arg Pro Arg Thr Val Thr Val
1               5                   10                  15

Thr Phe Gly Arg Arg
            20

<210> SEQ ID NO 109
<211> LENGTH: 21
<212> TYPE: PRT
<213> ORGANISM: Artificial Sequence
<220> FEATURE:
<223> OTHER INFORMATION: Peptide sequence

<400> SEQUENCE: 109

Arg Ile Gly Arg Leu Leu Leu Arg Arg Pro Arg Ile Gly Ala Leu
1               5                   10                  15

Leu Leu Leu Arg Arg
            20

<210> SEQ ID NO 110
<211> LENGTH: 21
<212> TYPE: PRT
<213> ORGANISM: Artificial Sequence
<220> FEATURE:
<223> OTHER INFORMATION: Peptide sequence

<400> SEQUENCE: 110

Arg Thr Val Thr Val Thr Phe Arg Arg Arg Pro Arg Thr Val Thr Val
1               5                   10                  15

Thr Phe Asn Arg Arg
            20

<210> SEQ ID NO 111
<211> LENGTH: 21
<212> TYPE: PRT
<213> ORGANISM: Artificial Sequence
<220> FEATURE:
<223> OTHER INFORMATION: Peptide sequence

<400> SEQUENCE: 111

Arg Ala Leu Ile Arg Ala Leu Gln Arg Arg Pro Arg Ala Leu Ile Ala
1               5                   10                  15

Ala Leu Gln Arg Arg
            20

<210> SEQ ID NO 112
<211> LENGTH: 21
<212> TYPE: PRT
<213> ORGANISM: Artificial Sequence
<220> FEATURE:
<223> OTHER INFORMATION: Peptide sequence

<400> SEQUENCE: 112

Arg Val Leu Ala Leu Arg Ala Leu Arg Arg Pro Arg Val Leu Ala Leu
1               5                   10                  15

```
Ala Ala Leu Arg Arg
            20

<210> SEQ ID NO 113
<211> LENGTH: 21
<212> TYPE: PRT
<213> ORGANISM: Artificial Sequence
<220> FEATURE:
<223> OTHER INFORMATION: Peptide sequence

<400> SEQUENCE: 113

Arg Ala Leu Ala Arg Ala Leu Leu Arg Arg Pro Arg Ala Leu Ala Val
1               5                   10                  15

Ala Leu Leu Arg Arg
            20

<210> SEQ ID NO 114
<211> LENGTH: 21
<212> TYPE: PRT
<213> ORGANISM: Artificial Sequence
<220> FEATURE:
<223> OTHER INFORMATION: Peptide sequence

<400> SEQUENCE: 114

Arg Ala Val Leu Arg Leu Leu Ala Arg Arg Pro Arg Ala Val Leu Gly
1               5                   10                  15

Leu Leu Ala Arg Arg
            20

<210> SEQ ID NO 115
<211> LENGTH: 21
<212> TYPE: PRT
<213> ORGANISM: Artificial Sequence
<220> FEATURE:
<223> OTHER INFORMATION: Peptide sequence

<400> SEQUENCE: 115

Arg Gly Leu Leu Ala Leu Arg Ala Arg Arg Pro Arg Gly Leu Leu Ala
1               5                   10                  15

Leu Leu Ala Arg Arg
            20

<210> SEQ ID NO 116
<211> LENGTH: 21
<212> TYPE: PRT
<213> ORGANISM: Artificial Sequence
<220> FEATURE:
<223> OTHER INFORMATION: Peptide sequence

<400> SEQUENCE: 116

Arg Leu Ile Arg Ile Ala Leu Gly Arg Arg Pro Arg Leu Ile Gly Ile
1               5                   10                  15

Ala Leu Gly Arg Arg
            20

<210> SEQ ID NO 117
<211> LENGTH: 21
<212> TYPE: PRT
<213> ORGANISM: Artificial Sequence
<220> FEATURE:
<223> OTHER INFORMATION: Peptide sequence

<400> SEQUENCE: 117

Arg Ala Leu Leu Thr Ala Val Arg Arg Arg Pro Arg Ala Leu Leu Thr
```

```
1               5                   10                  15

Ala Val Leu Arg Arg
            20

<210> SEQ ID NO 118
<211> LENGTH: 21
<212> TYPE: PRT
<213> ORGANISM: Artificial Sequence
<220> FEATURE:
<223> OTHER INFORMATION: Peptide sequence

<400> SEQUENCE: 118

Arg Gln Leu Val Ala Leu Arg Val Arg Arg Pro Arg Gln Leu Val Ala
1               5                   10                  15

Leu Leu Val Arg Arg
            20

<210> SEQ ID NO 119
<211> LENGTH: 21
<212> TYPE: PRT
<213> ORGANISM: Artificial Sequence
<220> FEATURE:
<223> OTHER INFORMATION: Peptide sequence

<400> SEQUENCE: 119

Arg Ser Ala Val Arg Ala Leu Leu Arg Arg Pro Arg Ser Ala Val Leu
1               5                   10                  15

Ala Leu Leu Arg Arg
            20

<210> SEQ ID NO 120
<211> LENGTH: 21
<212> TYPE: PRT
<213> ORGANISM: Artificial Sequence
<220> FEATURE:
<223> OTHER INFORMATION: Peptide sequence

<400> SEQUENCE: 120

Arg Val Val Thr Val Thr Arg Asn Arg Arg Pro Arg Val Val Thr Val
1               5                   10                  15

Thr Leu Asn Arg Arg
            20

<210> SEQ ID NO 121
<211> LENGTH: 21
<212> TYPE: PRT
<213> ORGANISM: Artificial Sequence
<220> FEATURE:
<223> OTHER INFORMATION: Peptide sequence

<400> SEQUENCE: 121

Arg Ala Val Val Arg Ala Thr Gly Arg Arg Pro Arg Ala Val Val Leu
1               5                   10                  15

Ala Thr Gly Arg Arg
            20

<210> SEQ ID NO 122
<211> LENGTH: 21
<212> TYPE: PRT
<213> ORGANISM: Artificial Sequence
<220> FEATURE:
<223> OTHER INFORMATION: Peptide sequence

<400> SEQUENCE: 122
```

```
Arg Leu Leu Arg Ile Val Leu Gly Arg Arg Pro Arg Leu Leu Leu Ile
1               5                   10                  15

Val Leu Gly Arg Arg
            20

<210> SEQ ID NO 123
<211> LENGTH: 21
<212> TYPE: PRT
<213> ORGANISM: Artificial Sequence
<220> FEATURE:
<223> OTHER INFORMATION: Peptide sequence

<400> SEQUENCE: 123

Arg Ala Leu Arg Val Ala Ile Gly Arg Arg Pro Arg Ala Leu Ala Val
1               5                   10                  15

Ala Ile Gly Arg Arg
            20

<210> SEQ ID NO 124
<211> LENGTH: 21
<212> TYPE: PRT
<213> ORGANISM: Artificial Sequence
<220> FEATURE:
<223> OTHER INFORMATION: Peptide sequence

<400> SEQUENCE: 124

Arg Ala Leu Arg Ile Thr Leu Leu Arg Arg Pro Arg Ala Leu Leu Ile
1               5                   10                  15

Thr Leu Leu Arg Arg
            20

<210> SEQ ID NO 125
<211> LENGTH: 21
<212> TYPE: PRT
<213> ORGANISM: Artificial Sequence
<220> FEATURE:
<223> OTHER INFORMATION: Peptide sequence

<400> SEQUENCE: 125

Arg Gly Leu Leu Arg Ala Leu Gln Arg Arg Pro Arg Gly Leu Leu Leu
1               5                   10                  15

Ala Leu Gln Arg Arg
            20

<210> SEQ ID NO 126
<211> LENGTH: 21
<212> TYPE: PRT
<213> ORGANISM: Artificial Sequence
<220> FEATURE:
<223> OTHER INFORMATION: Peptide sequence

<400> SEQUENCE: 126

Arg Ile Val Thr Arg Thr Leu Asn Arg Arg Pro Arg Ile Val Thr Val
1               5                   10                  15

Thr Leu Asn Arg Arg
            20

<210> SEQ ID NO 127
<211> LENGTH: 7
<212> TYPE: PRT
<213> ORGANISM: Escherichia coli

<400> SEQUENCE: 127

Leu Leu Leu Ser Leu Leu Val
```

```
1               5
```

<210> SEQ ID NO 128
<211> LENGTH: 7
<212> TYPE: PRT
<213> ORGANISM: Escherichia coli

<400> SEQUENCE: 128

```
Gly Leu Gly Leu Ala Leu Val
1               5
```

<210> SEQ ID NO 129
<211> LENGTH: 7
<212> TYPE: PRT
<213> ORGANISM: Escherichia coli

<400> SEQUENCE: 129

```
Leu Leu Leu Ala Leu Leu Ser
1               5
```

<210> SEQ ID NO 130
<211> LENGTH: 7
<212> TYPE: PRT
<213> ORGANISM: Escherichia coli

<400> SEQUENCE: 130

```
Leu Ala Leu Ala Leu Leu Leu
1               5
```

<210> SEQ ID NO 131
<211> LENGTH: 7
<212> TYPE: PRT
<213> ORGANISM: Escherichia coli

<400> SEQUENCE: 131

```
Ala Leu Leu Thr Thr Leu Leu
1               5
```

<210> SEQ ID NO 132
<211> LENGTH: 7
<212> TYPE: PRT
<213> ORGANISM: Escherichia coli

<400> SEQUENCE: 132

```
Thr Val Thr Val Thr Phe Gly
1               5
```

<210> SEQ ID NO 133
<211> LENGTH: 7
<212> TYPE: PRT
<213> ORGANISM: Escherichia coli

<400> SEQUENCE: 133

```
Thr Val Thr Val Thr Phe Gly
1               5
```

<210> SEQ ID NO 134
<211> LENGTH: 7
<212> TYPE: PRT
<213> ORGANISM: Escherichia coli

<400> SEQUENCE: 134

```
Ile Gly Ala Leu Leu Leu Leu
1               5
```

```
<210> SEQ ID NO 135
<211> LENGTH: 7
<212> TYPE: PRT
<213> ORGANISM: Escherichia coli

<400> SEQUENCE: 135

Thr Val Thr Val Thr Phe Asn
1               5

<210> SEQ ID NO 136
<211> LENGTH: 7
<212> TYPE: PRT
<213> ORGANISM: Escherichia coli

<400> SEQUENCE: 136

Ala Leu Ile Ala Ala Leu Gln
1               5

<210> SEQ ID NO 137
<211> LENGTH: 7
<212> TYPE: PRT
<213> ORGANISM: Escherichia coli

<400> SEQUENCE: 137

Val Leu Ala Leu Ala Ala Leu
1               5

<210> SEQ ID NO 138
<211> LENGTH: 7
<212> TYPE: PRT
<213> ORGANISM: Escherichia coli

<400> SEQUENCE: 138

Ala Leu Ala Val Ala Leu Leu
1               5

<210> SEQ ID NO 139
<211> LENGTH: 7
<212> TYPE: PRT
<213> ORGANISM: Escherichia coli

<400> SEQUENCE: 139

Ala Val Leu Gly Leu Leu Ala
1               5

<210> SEQ ID NO 140
<211> LENGTH: 7
<212> TYPE: PRT
<213> ORGANISM: Escherichia coli

<400> SEQUENCE: 140

Gly Leu Leu Ala Leu Leu Ala
1               5

<210> SEQ ID NO 141
<211> LENGTH: 7
<212> TYPE: PRT
<213> ORGANISM: Escherichia coli

<400> SEQUENCE: 141

Leu Ile Gly Ile Ala Leu Gly
1               5

<210> SEQ ID NO 142
```

```
<211> LENGTH: 7
<212> TYPE: PRT
<213> ORGANISM: Escherichia coli

<400> SEQUENCE: 142

Ala Leu Leu Thr Ala Val Leu
1               5

<210> SEQ ID NO 143
<211> LENGTH: 7
<212> TYPE: PRT
<213> ORGANISM: Escherichia coli

<400> SEQUENCE: 143

Gln Leu Val Ala Leu Leu Val
1               5

<210> SEQ ID NO 144
<211> LENGTH: 7
<212> TYPE: PRT
<213> ORGANISM: Escherichia coli

<400> SEQUENCE: 144

Ser Ala Val Leu Ala Leu Leu
1               5

<210> SEQ ID NO 145
<211> LENGTH: 7
<212> TYPE: PRT
<213> ORGANISM: Escherichia coli

<400> SEQUENCE: 145

Val Val Thr Val Thr Leu Asn
1               5

<210> SEQ ID NO 146
<211> LENGTH: 7
<212> TYPE: PRT
<213> ORGANISM: Escherichia coli

<400> SEQUENCE: 146

Ala Val Val Leu Ala Thr Gly
1               5

<210> SEQ ID NO 147
<211> LENGTH: 7
<212> TYPE: PRT
<213> ORGANISM: Escherichia coli

<400> SEQUENCE: 147

Leu Leu Leu Ile Val Leu Gly
1               5

<210> SEQ ID NO 148
<211> LENGTH: 7
<212> TYPE: PRT
<213> ORGANISM: Escherichia coli

<400> SEQUENCE: 148

Ala Leu Ala Val Ala Ile Gly
1               5

<210> SEQ ID NO 149
<211> LENGTH: 7
<212> TYPE: PRT
```

<213> ORGANISM: Escherichia coli

<400> SEQUENCE: 149

Ala Leu Leu Ile Thr Leu Leu
1               5

<210> SEQ ID NO 150
<211> LENGTH: 7
<212> TYPE: PRT
<213> ORGANISM: Escherichia coli

<400> SEQUENCE: 150

Gly Leu Leu Leu Ala Leu Gln
1               5

<210> SEQ ID NO 151
<211> LENGTH: 7
<212> TYPE: PRT
<213> ORGANISM: Escherichia coli

<400> SEQUENCE: 151

Ile Val Thr Val Thr Leu Asn
1               5

<210> SEQ ID NO 152
<211> LENGTH: 7
<212> TYPE: PRT
<213> ORGANISM: Escherichia coli

<400> SEQUENCE: 152

Leu Phe Val Gly Leu Ala Leu
1               5

<210> SEQ ID NO 153
<211> LENGTH: 7
<212> TYPE: PRT
<213> ORGANISM: Escherichia coli

<400> SEQUENCE: 153

Val Leu Gly Leu Ala Ala Leu
1               5

<210> SEQ ID NO 154
<211> LENGTH: 7
<212> TYPE: PRT
<213> ORGANISM: Escherichia coli

<400> SEQUENCE: 154

Val Val Gly Leu Leu Ala Gly
1               5

<210> SEQ ID NO 155
<211> LENGTH: 7
<212> TYPE: PRT
<213> ORGANISM: Escherichia coli

<400> SEQUENCE: 155

Ala Thr Val Leu Ala Leu Leu
1               5

<210> SEQ ID NO 156
<211> LENGTH: 7
<212> TYPE: PRT
<213> ORGANISM: Escherichia coli

<400> SEQUENCE: 156

Ala Val Leu Val Ala Ile Gly
1               5

<210> SEQ ID NO 157
<211> LENGTH: 7
<212> TYPE: PRT
<213> ORGANISM: Escherichia coli

<400> SEQUENCE: 157

Gly Leu Leu Val Thr Leu Ala
1               5

<210> SEQ ID NO 158
<211> LENGTH: 7
<212> TYPE: PRT
<213> ORGANISM: Escherichia coli

<400> SEQUENCE: 158

Leu Phe Val Ile Leu Ala Leu
1               5

<210> SEQ ID NO 159
<211> LENGTH: 7
<212> TYPE: PRT
<213> ORGANISM: Escherichia coli

<400> SEQUENCE: 159

Leu Gly Ile Ala Val Ala Leu
1               5

<210> SEQ ID NO 160
<211> LENGTH: 7
<212> TYPE: PRT
<213> ORGANISM: Escherichia coli

<400> SEQUENCE: 160

Leu Leu Leu Leu Val Asn Leu
1               5

<210> SEQ ID NO 161
<211> LENGTH: 7
<212> TYPE: PRT
<213> ORGANISM: Escherichia coli

<400> SEQUENCE: 161

Thr Val Thr Val Ala Leu Gly
1               5

<210> SEQ ID NO 162
<211> LENGTH: 7
<212> TYPE: PRT
<213> ORGANISM: Escherichia coli

<400> SEQUENCE: 162

Val Gly Val Ile Val Gly Ala
1               5

<210> SEQ ID NO 163
<211> LENGTH: 7
<212> TYPE: PRT
<213> ORGANISM: Escherichia coli

<400> SEQUENCE: 163

```
Val Val Val Ala Ile Ala Leu
1               5

<210> SEQ ID NO 164
<211> LENGTH: 7
<212> TYPE: PRT
<213> ORGANISM: Escherichia coli

<400> SEQUENCE: 164

Ala Gly Leu Leu Ser Leu Val
1               5

<210> SEQ ID NO 165
<211> LENGTH: 7
<212> TYPE: PRT
<213> ORGANISM: Escherichia coli

<400> SEQUENCE: 165

Ala Leu Leu Ile Gln Leu Leu
1               5

<210> SEQ ID NO 166
<211> LENGTH: 7
<212> TYPE: PRT
<213> ORGANISM: Escherichia coli

<400> SEQUENCE: 166

Ala Gln Val Leu Ala Leu Leu
1               5

<210> SEQ ID NO 167
<211> LENGTH: 7
<212> TYPE: PRT
<213> ORGANISM: Escherichia coli

<400> SEQUENCE: 167

Ala Val Val Leu Ala Val Asn
1               5

<210> SEQ ID NO 168
<211> LENGTH: 7
<212> TYPE: PRT
<213> ORGANISM: Escherichia coli

<400> SEQUENCE: 168

Phe Val Ala Gly Phe Ile Gly
1               5

<210> SEQ ID NO 169
<211> LENGTH: 7
<212> TYPE: PRT
<213> ORGANISM: Escherichia coli

<400> SEQUENCE: 169

Leu Ala Ile Ala Leu Ala Gln
1               5

<210> SEQ ID NO 170
<211> LENGTH: 7
<212> TYPE: PRT
<213> ORGANISM: Escherichia coli

<400> SEQUENCE: 170

Leu Phe Ile Ile Ala Thr Ala
1               5
```

```
<210> SEQ ID NO 171
<211> LENGTH: 7
<212> TYPE: PRT
<213> ORGANISM: Escherichia coli

<400> SEQUENCE: 171

Leu Ile Val Ala Ala Ile Ala
1               5

<210> SEQ ID NO 172
<211> LENGTH: 7
<212> TYPE: PRT
<213> ORGANISM: Escherichia coli

<400> SEQUENCE: 172

Leu Leu Ala Gly Ile Val Ala
1               5

<210> SEQ ID NO 173
<211> LENGTH: 7
<212> TYPE: PRT
<213> ORGANISM: Escherichia coli

<400> SEQUENCE: 173

Leu Leu Leu Ala Tyr Leu Leu
1               5

<210> SEQ ID NO 174
<211> LENGTH: 7
<212> TYPE: PRT
<213> ORGANISM: Escherichia coli

<400> SEQUENCE: 174

Leu Leu Leu Met Leu Ala Gly
1               5

<210> SEQ ID NO 175
<211> LENGTH: 7
<212> TYPE: PRT
<213> ORGANISM: Escherichia coli

<400> SEQUENCE: 175

Leu Leu Thr Leu Leu Asn Leu
1               5

<210> SEQ ID NO 176
<211> LENGTH: 7
<212> TYPE: PRT
<213> ORGANISM: Escherichia coli

<400> SEQUENCE: 176

Leu Val Gly Leu Val Leu Gly
1               5

<210> SEQ ID NO 177
<211> LENGTH: 7
<212> TYPE: PRT
<213> ORGANISM: Escherichia coli

<400> SEQUENCE: 177

Leu Val Val Thr Ala Ile Ala
1               5
```

```
<210> SEQ ID NO 178
<211> LENGTH: 7
<212> TYPE: PRT
<213> ORGANISM: Escherichia coli

<400> SEQUENCE: 178

Pro Val Ile Ile Leu Thr Ala
1               5

<210> SEQ ID NO 179
<211> LENGTH: 7
<212> TYPE: PRT
<213> ORGANISM: Escherichia coli

<400> SEQUENCE: 179

Gln Ala Ile Val Ile Thr Gly
1               5

<210> SEQ ID NO 180
<211> LENGTH: 7
<212> TYPE: PRT
<213> ORGANISM: Escherichia coli

<400> SEQUENCE: 180

Thr Val Val Leu Leu Ala Ala
1               5

<210> SEQ ID NO 181
<211> LENGTH: 7
<212> TYPE: PRT
<213> ORGANISM: Escherichia coli

<400> SEQUENCE: 181

Ala Ala Leu Ile Thr Ala Leu
1               5

<210> SEQ ID NO 182
<211> LENGTH: 7
<212> TYPE: PRT
<213> ORGANISM: Escherichia coli

<400> SEQUENCE: 182

Ala Ala Leu Leu Ala Tyr Val
1               5

<210> SEQ ID NO 183
<211> LENGTH: 7
<212> TYPE: PRT
<213> ORGANISM: Escherichia coli

<400> SEQUENCE: 183

Ala Ile Thr Leu Val Leu Thr
1               5

<210> SEQ ID NO 184
<211> LENGTH: 7
<212> TYPE: PRT
<213> ORGANISM: Escherichia coli

<400> SEQUENCE: 184

Ala Leu Val Ser Leu Leu Leu
1               5

<210> SEQ ID NO 185
<211> LENGTH: 7
```

```
<212> TYPE: PRT
<213> ORGANISM: Escherichia coli

<400> SEQUENCE: 185

Gly Ile Val Gly Leu Val Gly
1               5

<210> SEQ ID NO 186
<211> LENGTH: 7
<212> TYPE: PRT
<213> ORGANISM: Escherichia coli

<400> SEQUENCE: 186

Gly Leu Ala Val Gly Val Ile
1               5

<210> SEQ ID NO 187
<211> LENGTH: 7
<212> TYPE: PRT
<213> ORGANISM: Escherichia coli

<400> SEQUENCE: 187

Gly Thr Val Leu Leu Val Ser
1               5

<210> SEQ ID NO 188
<211> LENGTH: 7
<212> TYPE: PRT
<213> ORGANISM: Escherichia coli

<400> SEQUENCE: 188

Gly Val Ala Leu Val Val Ala
1               5

<210> SEQ ID NO 189
<211> LENGTH: 7
<212> TYPE: PRT
<213> ORGANISM: Escherichia coli

<400> SEQUENCE: 189

Gly Val Leu Ala Val Phe Ala
1               5

<210> SEQ ID NO 190
<211> LENGTH: 7
<212> TYPE: PRT
<213> ORGANISM: Escherichia coli

<400> SEQUENCE: 190

Ile Leu Leu Leu Thr Leu Val
1               5

<210> SEQ ID NO 191
<211> LENGTH: 7
<212> TYPE: PRT
<213> ORGANISM: Escherichia coli

<400> SEQUENCE: 191

Ile Val Ile Val Gly Gly Gly
1               5

<210> SEQ ID NO 192
<211> LENGTH: 7
<212> TYPE: PRT
<213> ORGANISM: Escherichia coli
```

<400> SEQUENCE: 192

Leu Cys Leu Leu Leu Ala Leu
1               5

<210> SEQ ID NO 193
<211> LENGTH: 7
<212> TYPE: PRT
<213> ORGANISM: Escherichia coli

<400> SEQUENCE: 193

Leu Leu Ala Ile Leu Ala Ser
1               5

<210> SEQ ID NO 194
<211> LENGTH: 7
<212> TYPE: PRT
<213> ORGANISM: Escherichia coli

<400> SEQUENCE: 194

Leu Leu Ile Ala Val Gly Ala
1               5

<210> SEQ ID NO 195
<211> LENGTH: 7
<212> TYPE: PRT
<213> ORGANISM: Escherichia coli

<400> SEQUENCE: 195

Leu Leu Ile Val Leu Gly Ala
1               5

<210> SEQ ID NO 196
<211> LENGTH: 7
<212> TYPE: PRT
<213> ORGANISM: Escherichia coli

<400> SEQUENCE: 196

Asn Val Val Leu Leu Ala Leu
1               5

<210> SEQ ID NO 197
<211> LENGTH: 7
<212> TYPE: PRT
<213> ORGANISM: Escherichia coli

<400> SEQUENCE: 197

Pro Ala Ile Val Ala Ala Val
1               5

<210> SEQ ID NO 198
<211> LENGTH: 7
<212> TYPE: PRT
<213> ORGANISM: Escherichia coli

<400> SEQUENCE: 198

Gln Leu Leu Leu Thr Leu Leu
1               5

<210> SEQ ID NO 199
<211> LENGTH: 7
<212> TYPE: PRT
<213> ORGANISM: Escherichia coli

<400> SEQUENCE: 199

```
Ser Ala Ile Gly Ile Ile
1               5

<210> SEQ ID NO 200
<211> LENGTH: 7
<212> TYPE: PRT
<213> ORGANISM: Escherichia coli

<400> SEQUENCE: 200

Val Ser Leu Val Ala Ile Leu
1               5

<210> SEQ ID NO 201
<211> LENGTH: 7
<212> TYPE: PRT
<213> ORGANISM: Escherichia coli

<400> SEQUENCE: 201

Val Val Ala Leu Val Ala Gly
1               5

<210> SEQ ID NO 202
<211> LENGTH: 7
<212> TYPE: PRT
<213> ORGANISM: Escherichia coli

<400> SEQUENCE: 202

Gly Leu Gly Leu Ala Leu Ala
1               5

<210> SEQ ID NO 203
<211> LENGTH: 7
<212> TYPE: PRT
<213> ORGANISM: Escherichia coli

<400> SEQUENCE: 203

Gly Leu Gly Leu Ala Ile Val
1               5

<210> SEQ ID NO 204
<211> LENGTH: 7
<212> TYPE: PRT
<213> ORGANISM: Escherichia coli

<400> SEQUENCE: 204

Gly Leu Gly Leu Ser Leu Val
1               5

<210> SEQ ID NO 205
<211> LENGTH: 7
<212> TYPE: PRT
<213> ORGANISM: Escherichia coli

<400> SEQUENCE: 205

Gly Leu Gly Leu Ser Leu Val
1               5

<210> SEQ ID NO 206
<211> LENGTH: 7
<212> TYPE: PRT
<213> ORGANISM: Escherichia coli

<400> SEQUENCE: 206

Gly Leu Ala Leu Ala Leu Val
```

```
1               5
```

<210> SEQ ID NO 207
<211> LENGTH: 7
<212> TYPE: PRT
<213> ORGANISM: Escherichia coli

<400> SEQUENCE: 207

```
Gly Leu Gly Leu Ala Val Val
1               5
```

<210> SEQ ID NO 208
<211> LENGTH: 7
<212> TYPE: PRT
<213> ORGANISM: Escherichia coli

<400> SEQUENCE: 208

```
Gly Leu Pro Leu Ala Leu Val
1               5
```

<210> SEQ ID NO 209
<211> LENGTH: 7
<212> TYPE: PRT
<213> ORGANISM: Escherichia coli

<400> SEQUENCE: 209

```
Gly Val Gly Leu Ala Leu Val
1               5
```

<210> SEQ ID NO 210
<211> LENGTH: 7
<212> TYPE: PRT
<213> ORGANISM: Escherichia coli

<400> SEQUENCE: 210

```
Gly Leu Gly Leu Ala Leu Ser
1               5
```

<210> SEQ ID NO 211
<211> LENGTH: 7
<212> TYPE: PRT
<213> ORGANISM: Escherichia coli

<400> SEQUENCE: 211

```
Gly Leu Leu Leu Ala Leu Val
1               5
```

<210> SEQ ID NO 212
<211> LENGTH: 7
<212> TYPE: PRT
<213> ORGANISM: Escherichia coli

<400> SEQUENCE: 212

```
Gly Leu Gly Leu Ala Leu Gln
1               5
```

<210> SEQ ID NO 213
<211> LENGTH: 7
<212> TYPE: PRT
<213> ORGANISM: Escherichia coli

<400> SEQUENCE: 213

```
Gly Ile Gly Leu Ala Leu Val
1               5
```

<210> SEQ ID NO 214
<211> LENGTH: 7
<212> TYPE: PRT
<213> ORGANISM: Escherichia coli

<400> SEQUENCE: 214

Gly Leu Gly Leu Ala Phe Val
1               5

<210> SEQ ID NO 215
<211> LENGTH: 7
<212> TYPE: PRT
<213> ORGANISM: Escherichia coli

<400> SEQUENCE: 215

Gly Leu Ser Leu Ala Leu Val
1               5

<210> SEQ ID NO 216
<211> LENGTH: 7
<212> TYPE: PRT
<213> ORGANISM: Acinetobacter baumannii

<400> SEQUENCE: 216

Phe Leu Gly Leu Ala Leu Val
1               5

<210> SEQ ID NO 217
<211> LENGTH: 7
<212> TYPE: PRT
<213> ORGANISM: Acinetobacter baumannii

<400> SEQUENCE: 217

Gly Leu Gly Leu Leu Leu Val
1               5

<210> SEQ ID NO 218
<211> LENGTH: 7
<212> TYPE: PRT
<213> ORGANISM: Acinetobacter baumannii

<400> SEQUENCE: 218

Gly Leu Gly Leu Ala Asn Val
1               5

<210> SEQ ID NO 219
<211> LENGTH: 7
<212> TYPE: PRT
<213> ORGANISM: Acinetobacter baumannii

<400> SEQUENCE: 219

Gly Leu Gly Leu Ala Leu Trp
1               5

<210> SEQ ID NO 220
<211> LENGTH: 7
<212> TYPE: PRT
<213> ORGANISM: Acinetobacter baumannii

<400> SEQUENCE: 220

Gly Leu Gly Leu Ala Leu Leu
1               5

<210> SEQ ID NO 221

```
<211> LENGTH: 7
<212> TYPE: PRT
<213> ORGANISM: Acinetobacter baumannii

<400> SEQUENCE: 221

Asp Leu Gly Leu Ala Leu Val
1               5

<210> SEQ ID NO 222
<211> LENGTH: 7
<212> TYPE: PRT
<213> ORGANISM: Acinetobacter baumannii

<400> SEQUENCE: 222

Gly Leu Gly Leu Ala Leu Arg
1               5

<210> SEQ ID NO 223
<211> LENGTH: 7
<212> TYPE: PRT
<213> ORGANISM: Homo sapiens

<400> SEQUENCE: 223

Ile Leu Thr Ile Ile Thr Leu
1               5

<210> SEQ ID NO 224
<211> LENGTH: 28
<212> TYPE: DNA
<213> ORGANISM: Artificial Sequence
<220> FEATURE:
<223> OTHER INFORMATION: Primer

<400> SEQUENCE: 224
atgtcgacat gagcgatctg cataacga                                    28

<210> SEQ ID NO 225
<211> LENGTH: 32
<212> TYPE: DNA
<213> ORGANISM: Artificial Sequence
<220> FEATURE:
<223> OTHER INFORMATION: Primer

<400> SEQUENCE: 225
atgtcgacat ggagcgattt atcgaagaag gc                               32

<210> SEQ ID NO 226
<211> LENGTH: 28
<212> TYPE: DNA
<213> ORGANISM: Artificial Sequence
<220> FEATURE:
<223> OTHER INFORMATION: Primer

<400> SEQUENCE: 226
atcccgggtt aaagatccaa cccagccg                                    28

<210> SEQ ID NO 227
<211> LENGTH: 44
<212> TYPE: DNA
<213> ORGANISM: Artificial Sequence
<220> FEATURE:
<223> OTHER INFORMATION: Primer

<400> SEQUENCE: 227
catatgatgc atcatcacca tcaccacagc gatctgcata acga                  44
```

```
<210> SEQ ID NO 228
<211> LENGTH: 26
<212> TYPE: DNA
<213> ORGANISM: Artificial Sequence
<220> FEATURE:
<223> OTHER INFORMATION: Primer

<400> SEQUENCE: 228
cctaggttaa agatccaacc cagccg                                        26

<210> SEQ ID NO 229
<211> LENGTH: 42
<212> TYPE: DNA
<213> ORGANISM: Artificial Sequence
<220> FEATURE:
<223> OTHER INFORMATION: Primer

<400> SEQUENCE: 229
agaattcggc agcggcagcg gcagcgtgag caagggcgag ga                       42

<210> SEQ ID NO 230
<211> LENGTH: 42
<212> TYPE: DNA
<213> ORGANISM: Artificial Sequence
<220> FEATURE:
<223> OTHER INFORMATION: Primer

<400> SEQUENCE: 230
agaattcggc agcggcagcg gcagcgtgag caagggcgag ga                       42

<210> SEQ ID NO 231
<211> LENGTH: 65
<212> TYPE: DNA
<213> ORGANISM: Artificial Sequence
<220> FEATURE:
<223> OTHER INFORMATION: Primer

<400> SEQUENCE: 231
agatgacgat gttgtcgacg ctgaatttga agaagtcaaa gacaaaaaag gcagcggcag    60
cggca                                                               65

<210> SEQ ID NO 232
<211> LENGTH: 70
<212> TYPE: DNA
<213> ORGANISM: Artificial Sequence
<220> FEATURE:
<223> OTHER INFORMATION: Primer

<400> SEQUENCE: 232
aggaaattcc ccttcgcccg tgtcagtata attacccgtt tatagggcga gtgtaggctg    60
gagctgcttc                                                          70

<210> SEQ ID NO 233
<211> LENGTH: 21
<212> TYPE: PRT
<213> ORGANISM: Artificial Sequence
<220> FEATURE:
<223> OTHER INFORMATION: Peptide sequence

<400> SEQUENCE: 233

Arg Leu Cys Leu Leu Leu Ala Leu Arg Arg Pro Arg Leu Cys Leu Leu
1               5                   10                  15

Leu Ala Leu Arg Arg
            20
```

```
<210> SEQ ID NO 234
<211> LENGTH: 8
<212> TYPE: PRT
<213> ORGANISM: Artificial Sequence
<220> FEATURE:
<223> OTHER INFORMATION: FLAG tag

<400> SEQUENCE: 234

Asp Tyr Lys Asp Asp Asp Asp Lys
1               5

<210> SEQ ID NO 235
<211> LENGTH: 6
<212> TYPE: PRT
<213> ORGANISM: Artificial Sequence
<220> FEATURE:
<223> OTHER INFORMATION: Linker

<400> SEQUENCE: 235

Gly Ser Gly Ser Gly Ser
1               5

<210> SEQ ID NO 236
<211> LENGTH: 8
<212> TYPE: PRT
<213> ORGANISM: Artificial Sequence
<220> FEATURE:
<223> OTHER INFORMATION: FLAG tag

<400> SEQUENCE: 236

Asp Tyr Lys Asp Asp Asp Asp Lys
1               5
```